(12) United States Patent
Dinchuk et al.

(10) Patent No.: US 7,259,000 B2
(45) Date of Patent: Aug. 21, 2007

(54) POLYNUCLEOTIDES ENCODING CHIMERIC CHEMOKINE RECEPTORS

(75) Inventors: Joseph E. Dinchuk, Stockton, NJ (US); Paul Davies, Wilmington, DE (US); Qihong Zhao, Princeton, NJ (US); Percy H. Carter, Princeton, NJ (US); Kimberly A. Solomon, Landenberg, PA (US); Peggy Ann Scherle, Media, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/988,267

(22) Filed: Nov. 12, 2004

(65) Prior Publication Data

US 2005/0123972 A1 Jun. 9, 2005

Related U.S. Application Data

(60) Provisional application No. 60/519,605, filed on Nov. 13, 2003.

(51) Int. Cl.
*C12P 21/02* (2006.01)
*C12N 5/10* (2006.01)
*C12N 15/63* (2006.01)
*C07H 21/04* (2006.01)

(52) U.S. Cl. ............... 435/69.7; 435/325; 435/252.3; 435/254.11; 435/254.2; 435/320.1; 536/23.4

(58) Field of Classification Search ............ None
See application file for complete search history.

(56) References Cited

U.S. PATENT DOCUMENTS 5,707,815 A * 1/1998 Charo et al. ............... 435/7.2
2004/0082616 A1 4/2004 Duncia et al.

OTHER PUBLICATIONS

Lu, et al., "Evolution of HIV-1 coreceptor usage through interactions with distinct CCR5 and CXCR4 domains", PNAS, vol. 94, pp. 6426-6431 (1997).
Choe, et al., "The β-Chemokine Receptors CCR3 and CCR5 Facilitate Infection by Primary HIV-1 Isolates", Cell, vol. 85, pp. 1135-1148 (1996).
NCBI Entrez Accession No. AF545480 (gi:23267189), Rieder, M.J. et al., Sep. 22, 2002.
NCBI Entrez Accession No. D10924 (gi:219868), Nomura, H. et al., Feb. 8, 2003.
NCBI Entrez Accession No. D10925 (gi:219862), Nomura, H. et al., Feb. 8, 2003.
NCBI Entrez Accession No. D29984 (gi:531246), Yamagami, S. et al., Feb. 8, 2003.
NCBI Entrez Accession No. L01639 (gi:189313), Jazin, E.E. et al., Mar. 9, 1994.
NCBI Entrez Accession No. L06797 (gi:414929), Herzog, H. et al., Nov. 10, 1993.
NCBI Entrez Accession No. L08176 (gi:183484), Birkenbach, M. et al., Dec. 31, 1994.
NCBI Entrez Accession No. L09230 (gi:179984), Neote, K. et al., Dec. 31, 1994.
NCBI Entrez Accession No. L10918 (gi:292416), Gao, J.L. et al., Jun. 12, 1993.
NCBI Entrez Accession No. L19591 (gi:559049), Holmes, W.E. et al., Jan. 6, 1995.
NCBI Entrez Accession No. L19592 (gi:559051), Holmes, W.E. et al., Jan. 6, 1995.
NCBI Entrez Accession No. L19593 (gi:559053), Murphy, P.M. et al., Jan. 6, 1995.
NCBI Entrez Accession No. L31581 (gi:468319), Schweickart, V.L. et al., Aug. 10, 1995.
NCBI Entrez Accession No. L31584 (gi:468314), Schweickart, V.L. et al., Feb. 11, 2002.
NCBI Entrez Accession No. L36149 (gi:598154), Heiber, M. et al., Feb. 28, 1995.
NCBI Entrez Accession No. M68932 (gi:186369), Holmes, W.E. et al., Jan. 6, 1995.
NCBI Entrez Accession No. M73969 (gi:186516), Murphy, P.M. et al., Dec. 8, 1995.
NCBI Entrez Accession No. M94582 (gi:186377), Murphy, P.M. et al., Apr. 27, 1993.
NCBI Entrez Accession No. M99293 (gi:292516), Federsppiel, B. et al., Mar. 10, 1994.
NCBI Entrez Accession No. M99412 (gi:576678), Sprenger, H. et al., Apr. 22, 1998.
NCBI Entrez Accession No. U03882 (gi:472555), Charo, I.F. et al., Jun. 22, 1994.
NCBI Entrez Accession No. U03905 (gi:472557), Charo, I.F. et al., Jun. 22, 1994.
NCBI Entrez Accession No. U11869 (gi:511801), Ahuja, S.K. et al., Aug. 23, 2002.
NCBI Entrez Accession No. U11870 (gi:511804), Ahuja, S.K. et al., Mar. 28, 1995.
NCBI Entrez Accession No. U13667 (gi:577414), Marchese, A. et al., Apr. 1, 1995.
NCBI Entrez Accession No. U20350 (gi:665580), Raport, C.J. et al., Mar. 9, 1996.

(Continued)

*Primary Examiner*—Ruixiang Li
(74) *Attorney, Agent, or Firm*—Todd Spalding

(57) ABSTRACT

The present invention relates to a chimeric chemokine receptor comprising two components: a first sequence comprising the N terminus through the last residue of the seven helix TM region of a first chemokine receptor joined with a second sequence comprising the C terminus of a second chemokine receptor extending from the first intracellular residue of the chemokine receptor to the last residue of the chemokine receptor. The chimeric chemokine receptor can be employed in various applications, such as ligand binding and screening assays and signalling assays. The chimeric chemokine receptor can also form a component of a chemokine receptor modulator design program.

6 Claims, 12 Drawing Sheets

OTHER PUBLICATIONS

NCBI Entrez Accession No. U28694 (gi:1199579), Combadiere, C. et al., May 16, 1996.

NCBI Entrez Accession No. U28934 (gi:881599), Combadiere, C. et al., Feb. 9, 1996.

NCBI Entrez Accession No. U32674 (gi:1002740), Marchese, A. et al., Jun. 5, 1996.

NCBI Entrez Accession No. U45982 (gi:1245054), Lautens, L.L. et al., Apr. 2, 1996.

NCBI Entrez Accession No. U45983 (gi:2231165), Tiffany, H.L. et al., Sep. 30, 2002.

NCBI Entrez Accession No. U45984 (gi:2246432), Baba, M. et al., Jul. 9, 1997.

NCBI Entrez Accession No. U49727 (gi:1477560), Ponath, P.D. et al., Oct. 4, 1996.

NCBI Entrez Accession No. U51241 (gi:1480480), Daugherty, B.L. et al., Oct. 9, 1996.

NCBI Entrez Accession No. U54994 (gi:1457945), Raport, C.J. et al., Jul. 25, 1996.

NCBI Entrez Accession No. U57840 (gi:1502408), Combadiere, C. et al., Oct. 18, 1996.

NCBI Entrez Accession No. U60000 (gi:1515434), McCoy, R. et al., Aug. 30, 1996.

NCBI Entrez Accession No. U62556 (gi:1468978), Napolitano, M. et al., Mar. 11, 2002.

NCBI Entrez Accession No. U68032 (gi:1870668), Liao, F. et al., Mar. 6, 1997.

NCBI Entrez Accession No. U73531 (gi:2209287), Liao, F. et al., Jun. 23, 1997.

NCBI Entrez Accession No. U80924 (gi:1773032), Wong, L.M. et al., Jul. 24, 1997.

NCBI Entrez Accession No. X65858 (gi:312046), Mollereau, C. et al., Jun. 25, 1997.

NCBI Entrez Accession No. X68149 (gi:29459), Dobner, T. et al., Nov. 1, 1999.

NCBI Entrez Accession No. X68829 (gi:840783), Barella, L. et al., Oct. 18, 1995.

NCBI Entrez Accession No. X71635 (gi:297099), Loetscher, M. et al., Feb. 15, 1994.

NCBI Entrez Accession No. X84702 (gi:673391), Burgstahler, R. et al., Feb. 6, 1996.

NCBI Entrez Accession No. X85740 (gi:1370103), Power, C.A. et al., Jun. 4, 1996.

NCBI Entrez Accession No. X91492 (gi:1262810), Samson, M. et al., Oct. 4, 1996.

NCBI Entrez Accession No. X95876 (gi:1552845), Loetscher, M. et al., Sep. 9, 2004.

NCBI Entrez Accession No. Y08456 (gi:2465081), Samson, M. et al., Sep. 9, 2004.

NCBI Entrez Accession No. Z79782 (gi:1668735), Zaballos, A. et al., Nov. 13, 1996.

Adachi, T. et al., "The Functional Role of Rho and Rho-Associated Coiled-Coil Forming Protein Kinase in Eotaxin Signaling of Eosinophils", The Journal of Immunology, vol. 167, pp. 4609-4615 (2001).

Alkhatib, G. et al., "Determinants of HIV-1 Coreceptor Function on CC Chemokine Receptor 3", The Journal of Biological Chemistry, vol. 272, No. 33, pp. 20420-20426 (1997).

Baba, M. et al., "Identification of CCR6, the Specific Receptor for a Novel Lymphocyte-directed CC Chemokine LARC", The Journal of Biological Chemistry, vol. 272, No. 23, pp. 14893-14898 (1997).

Baggiolini, M. et al., "Chemokines and leukocyte traffic", Nature, vol. 392, pp. 565-568 (1998).

Baggiolini, M. et al., "Human Chemokines: An Update", Annu. Rev. Immunol., vol. 15, pp. 675-705 (1997).

Castro-Fernández, C. et al., "Regulation of the gonadotropin-releasing hormone receptor (GnRHR) by RGS proteins: role of the GnRHR carboxyl-terminus", Molecular and Cellular Endocrinology, vol. 191, pp. 149-156 (2002).

Charo, I.F. et al., "Molecular cloning and functional expression of two monocyte chemoattractant protein 1 receptors reveals alternative splicing of the carboxyl-terminal tails", Proc. Natl. Acad. Sci. USA, vol. 91, pp. 2752-2756 (1994).

Combadiere, C. et al., "Cloning and Functional Expression of a Human Eosinophil CC Chemokine Receptor", The Journal of Biological Chemistry, vol. 270, No. 27, pp. 16491-16494, 30235 (correction) (1995).

Combadiere, C. et al., "Cloning and functional expression of CC CKR5, a human monocyte CC chemokine receptor selective for MIP-1α, MIP-1β, and RANTES", Journal of Leukocyte Biology, vol. 60, pp. 147-152 (1996).

Combadiere, C. et al., "Identification of $CX_3CR1$: A Chemotactic Receptor for the Human $CX_3C$ Chemokine Fractalkine and a Fusion Coreceptor for HIV-1", The Journal of Biological Chemistry, vol. 273, No. 37, pp. 23799-23804 (1998).

Daugherty, B.L. et al., "Cloning, Expression, and Characterization of the Human Eosinophil Eotaxin Receptor", J. Exp. Med., vol. 183, pp. 2349-2354 (1996).

El-Shazly, A. et al., "Novel Association of the Src Family Kinases, Hck and c-Fgr, with CCR3 Receptor Stimulation: A Possible Mechanism for Eotaxin-Induced Human Eosinophil Chemotaxis", Biochemical and Biophysical Research Communications, vol. 264, No. 1, pp. 163-170 (1999).

Elsner, J. et al., "Eotaxin-2 activates chemotaxis-related events and release of reactive oxygen species via pertussis toxin-sensitive G proteins in human eosinophils", Eur. J. Immunol., vol. 28, pp. 2152-2158 (1998).

Elsner, J. et al., "Human eotaxin represents a potent activator of the respiratory burst of human eosinophils", Eur. J. Immunol., vol. 26, pp. 1919-1925 (1996).

Federsppiel, B. et al., "Molecular Cloning of the cDNA and Chromosomal Localization of the Gene for a Putative Seven-Transmembrane Segment (7-TMS) Receptor Isolated from Human Spleen", Genomics, vol. 16, pp. 707-712 (1993).

Gao, J.-L. et al., "Structure and Functional Expression of the Human Macrophage Inflammatory Protein 1α/RANTES Receptor", The Journal of Experimental Medicine, vol. 177, pp. 1421-1427 (1993).

Gardella, T.J. et al., "Molecular properties of the PTH/PTHrP receptor", Trends in Endocrinology & Metabolism, vol. 12, No. 5, pp. 210-217 (2001).

Goya, I. et al., "Identification of CCR8 as the Specific Receptor for the Human β-Chemokine I-309: Cloning and Molecular Characterization of Murine CCR8 as the Receptor for TCA-3", The Journal of Immunology, vol. 160, pp. 1975-1981 (1998).

Heding, A. et al., "Gonadotropin-releasing Hormone Receptors with Intracellular Carboxyl-terminal Tails Undergo Acute Desensitization of Total Inositol Phosphate Production and Exhibit Accelerated Internalization Kinetics", The Journal of Biological Chemistry, vol. 273, No. 19, pp. 11472-11477 (1998).

Herzog, H. et al., "Molecular Cloning, Characterization, and Localization of the Human Homolog to the Reported Bovine NPY Y3 Receptor: Lack of NPY Binding and Activation", DNA and Cell Biology, vol. 12, No. 6, pp. 465-471 (1993).

Hill, C.M. et al., "The Amino Terminus of Human CCR5 Is Required for Its Function as a Receptor for Diverse Human and Simian Immunodeficiency Virus Envelope Glycoproteins", Virology, vol. 248, pp. 357-371 (1998).

Holmes, W.E. et al., "Structure and Functional Expression of a Human Interleukin-8 Receptor", Science, vol. 253, pp. 1278-1280 (1991).

Homey, B. et al., "Cutting Edge: The Orphan Chemokine Receptor G Protein-Coupled Receptor-2 (GPR-2, CCR10) Binds the Skin-Associated Chemokine CCL27 (CTACK/ALP/ILC)", The Journal of Immunology, vol. 164, pp. 3465-3470 (2000).

Horuk, R., "Chemokine receptors", Cytokine and Growth Factor Reviews, vol. 12, pp. 313-335 (2001).

Horuk, R., "Development and evaluation of pharmacological agents targeting chemokine receptors", Methods, vol. 29, pp. 369-375 (2003).

Horuk, R. et al., "The CC Chemokine I-309 Inhibits CCR8-dependent Infection by Diverse HIV-1 Strains", The Journal of Biological Chemistry, vol. 273, No. 1, pp. 386-391 (1998).

Humbles, A.A. et al., "The murine CCR3 receptor regulates both the role of eosinophils and mast cells in allergin-induced airway inflammation and hyperresponsiveness", Proc. Natl. Acad. Sci., vol. 99, No. 3, pp. 1479-1484 (2002).

Jarmin, D.I. et al., "Cutting Edge: Identification of the Orphan Receptor G-Protein-Coupled Receptor 2 as CCR10, a Specific Receptor for the Chemokine ESkine", The Journal of Immunology, vol. 164, pp. 3460-3464 (2000).

Jazin, E.E. et al., "A proposed bovine neuropeptide Y (NPY) receptor cDNA clone, or its human homologue, confers neither NPY binding sites nor NPY responsiveness on transfected cells", Regulatory Peptides, vol. 47, pp. 247-258 (1993).

Justice, J.P. et al., "Ablation of eosinophils leads to a reduction of allergin-induced pulmonary pathology", Am. J. Physiol. Lung Cell Mol. Physiol., vol. 284, pp. L169-L178 (2003).

Kampen, G.T. et al., "Eotaxin induces degranulation and chemotaxis of eosinophils through the activation of ERK2 and p38 mitogen-activated protein kinases", Blood, vol. 95, No. 6, pp. 1911-1917 (2000).

Legler, D.F. et al., "B Cell-attracting Chemokine 1, a Human CXC Chemokine Expressed in Lymphoid Tissues, Selectively Attracts B Lymphocytes via BLR1/CXCR5", J. Exp. Med., vol. 187, No. 4, pp. 655-660 (1998).

Ling, K. et al., "Five-transmembrane domains appear sufficient for a G protein-coupled receptor: Functional five-transmembrane domain chemokine receptors", Proc. Natl. Acad. Sci. USA, vol. 96, pp. 7922-7927 (1999).

Loetscher, M. et al., "Chemokine Receptor Specific for IP10 and Mig: Structure, Function, and Expression in Activated T-Lymphocytes", J. Exp. Med., vol. 184, pp. 963-969 (1996).

Loetscher, M. et al., "Cloning of a Human Seven-transmembrane Domain Receptor, LESTR, That Is Highly Expressed in Leukocytes", The Journal of Biological Chemistry, vol. 269, No. 1, pp. 232-237 (1994).

Lundahl, J. et al., "Eotaxin Increases the Expression of CD11b/CD18 and Ahesion Properties in IL5, but Not fMLP-Prestimulated Human Peripheral Blood Eosinophils", Inflammation, vol. 22, No. 2, pp. 123-135 (1998).

Ma, W. et al., "CCR3 is essential for skin eosinophilia and airway hyperresponsiveness in a murine model of allergic skin inflammation", The Journal of Clinical Investigation, vol. 109, No. 5, pp. 621-628 (2002).

Marchese, A. et al., "Cloning and Chromosomal Mapping of Three Novel Genes, GPR9, GPR10, and GPR14, Encoding Receptors Related to Interleukin 8, Neuropeptide Y, and Somatostatin Receptors", Genomics, vol. 29, pp. 335-344 (1995).

Matloubian, M. et al., "A transmembrane CXC chemokine is a ligand for HIV-coreceptor Bonzo", Nature Immunology, vol. 1, No. 4, pp. 298-304 (2000).

Monteclaro, F.S. et al., "The Amino-terminal Domain of CCR2 Is Both Necessary and Sufficient for High Affinity Binding of Monocyte Chemoattractant Protein 1: Receptor Activation by a Pseudo-Tethered Ligand", The Journal of Biological Chemistry, vol. 272, No. 37, pp. 23186-23190 (1997).

Murphy, P.M. et al., "Cloning of Complementary DNA Encoding a Functional Human Interleukin-8 Receptor", Science, vol. 253, pp. 1280-1283 (1991).

Nagasawa, T. et al., "Defects of B-cell lymphopoiesis and bone-marrow myelopoiesis in mice lacking the CXC chemokine PBSF/SDF-1", Nature, vol. 382, pp. 635-638 (1996).

Neote, K. et al., "Molecular Cloning, Functional Expression, and Signaling Characteristics of a C-C Chemokine Receptor", Cell, vol. 72, pp. 415-425 (1993).

Nomura, H. et al., "Molecular cloning of cDNAs encoding a LD78 receptor and putative leukocyte chemotactic peptide receptors", International Immunology, vol. 5, No. 10, pp. 1239-1249 (1993).

Onuffer, J.J. et al., "Chemokines, chemokine receptors and small-molecular antagonists: recent developments", Trends in Pharmacological Sciences, vol. 23, No. 10, pp. 459-467 (2002).

Pease, J.E. et al., "The N-terminal Extracellular Segments of the Chemokine Receptors CCR1 and CCR3 Are Determinants for MIP-1α and Eotaxin Binding, Respectively, but a Second Domain Is Essential for Efficient Receptor Activation", The Journal of Biological Chemistry, vol. 273, No. 32, pp. 19972-19976 (1998).

Peiper, S.C. et al., "Chimeric Chemokine Receptors for Analysis of Structure-Function Relationships", Methods in Enzymology, vol. 288, pp. 56-70 (1997).

Ponath, P.D. et al., "Cloning of the Human Eosinophil Chemoattractant, Eotaxin", J. Clin. Invest., vol. 97, No. 3, pp. 604-612 (1996).

Power, C.A. et al., "Molecular Cloning and Functional Expression of a Novel CC Chemokine Receptor cDNA from a Human Basophilic Cell Line", The Journal of Biological Chemistry, vol. 270, No. 33, pp. 19495-19500 (1995).

Rollins, B.J., "Chemokines", Blood, vol. 90, No. 3, pp. 909-928 (1997).

Roos, R.S. et al., "Identification of CCR8, the Receptor for the Human CC Chemokine I-309", The Journal of Biological Chemistry, vol. 272, No. 28, pp. 17251-17254 (1997).

Roth, S.J. et al., "C-C chemokines, but not the C-X-C chemokines interleukin-8 and interferon-γ inducible protein-10, stimulate transendothelial chemotaxis of T lymphocytes", Eur. J. Immunol., vol. 25, pp. 3482-3488 (1995).

Rucker, J. et al., "Regions in β-Chemokine Receptors CCR5 and CCR2b That Determine HIV-1 Cofactor Specificity", Cell, vol. 87, pp. 437-446 (1996).

Sallusto, F. et al., "Selective Expression of the Eotaxin Receptor CCR3 by Human T Helper 2 Cells", Science, vol. 277, pp. 2005-2007 (1997).

Samson, M. et al., "Molecular Cloning and Functional Expression of a New Human CC-Chemokine Receptor Gene", Biochemistry, vol. 35, No. 11, pp. 3362-3367 (1996).

Scherle, P.A. et al., "Inhibition of MAP Kinase Prevents Cytokine and Prostaglandin $E_2$ Production in Lipopolysaccharide-Stimulated Monocytes", The Journal of Immunology, vol. 161, pp. 5681-5686 (1998).

Sol, N. et al., "The Rhesus Macaque CCR3 Chemokine Receptor Is a Cell Entry Cofactor for HIV-2, but Not for HIV-1", Virology, vol. 240, pp. 213-220 (1998).

Tachimoto, H. et al., "Eotaxin-2 Alters Eosinophil Integrin Function via Mitogen-Activated Protein Kinases", Am. J. Respir. Cell Mol. Biol., vol. 26, pp. 645-649 (2002).

Taha, R.A. et al., "Evidence for increased expression of eotaxin and monocyte chemotactic protein-4 in atopic dermatitis", J. Allergy Clin. Immunol., vol. 105, No. 5, pp. 1002-1007 (2000).

Taub, D.D. et al., "Preferential Migration of Activated CD4[+] and CD8[+] T Cells in Response to MIP-1α and MIP-1β", Science, vol. 260, pp. 355-358 (1993).

Tenscher, K. et al., "Recombinant Human Eotaxin Induces Oxygen Radical Production, $Ca^{2+}$-Mobilization, Actin Reorganization, and CD11b Upregulation in Human Eosinophils Via a Pertussis Toxin-Sensitive Heterotrimeric Guanine Nucleotide-Binding Protein", Blood, vol. 88, No. 8, pp. 3195-3199 (1996).

Tiffany, H.L. et al., "Identification of CCR8: A Human Monocyte and Thymus Receptor for the CC Chemokine I-309", The Journal of Experimental Medicine, vol. 186, No. 1, pp. 165-170 (1997).

Trejo, J. et al., "Termination of signaling by protease-activated receptor-1 is linked to lysosomal sorting", Proc. Natl. Acad. Sci. USA, vol. 95, pp. 13698-13702 (1998).

Trejo, J. et al., "The Cytoplasmic Tails of Protease-activated Receptor-1 and Substance P Receptor Specify Sorting to Lysosomes versus Recycling", The Journal of Biological Chemistry, vol. 274, No. 4, pp. 2216-2224 (1999).

Uguccioni, M. et al., "High Expression of the Chemokine Receptor CCR3 in Human Blood Basophils", J. Clin. Invest., vol. 100, No. 5, pp. 1137-1143 (1997).

Vaidehi, N. et al., "Prediction of structure and function of G protein-coupled receptors", Proc. Natl. Acad. Sci., vol. 99, No. 20, pp. 12622-12627 (2002).

Woo, C.-H. et al., "Eotaxin induces migration of RBL-2H3 mast cells via a Rac-ERK-dependent pathway", Biochemical and Biophysical Research Communications, vol. 298, pp. 392-397 (2002).

Yawalkar, N. et al., "Enhanced Expression of Eotaxin and CCR3 in Atopic Dermatitis", J. Invest. Dermatol., vol. 113, No. 1, pp. 43-48 (1999).

Ying, S. et al., "C-C Chemokines in Allergin-Induced Late-Phase Cutaneous Responses in Atopic Subjects: Association of Eotaxin with Early 6-Hour Eosinophils, and of Eotaxin-2 and Monocyte Chemoattractant Protein-4 with the Later 24-Hour Tissue Eosinophilia, and Relationship to Basophils and Other C-C Chemokines (Monocyte Chemoattractant Protein-3 and RANTES)", The Journal of Immunology, vol. 163, pp. 3976-3984 (1999).

Yoshida, R. et al., "Molecular Cloning of a Novel Human CC Chemokine EBl1-ligand Chemokine That Is a Specific Functional Ligand for EBl1, CCR7", The Journal of Biological Chemistry, vol. 272, No. 21, pp. 13803-13809 (1997).

Yoshida, T. et al., "Identification of a Single C Motif-1/Lymphotactin Receptor XCR1", The Journal of Biological Chemistry, vol. 273, No. 26, pp. 16551-16554 (1998).

Yoshie, O. et al., "Chemokines in Immunity", Advances in Immunology, vol. 78, pp. 57-110 (2001).

Zaballos, A. et al., "Cutting Edge: Identification of the Orphan Chemokine Receptor GPR-9-6 as CCR9, the Receptor for the Chemokine TECK", The Journal of Immunology, vol. 162, pp. 5671-5675 (1999).

Zimmermann, N. et al., "CC Chemokine Receptor-3 Undergoes Prolonged Ligand-induced Internalization", The Journal of Biological Chemistry, vol. 274, No. 18, pp. 12611-12618 (1999).

* cited by examiner

FIG. 2B

```
                                              Start ORF of Preprotrypsin
            HindIII cloning site                    ↓           ┌Start ORF of human CCR3
agagctcgtttagtgaaccgtcagaatta  tcaccatgt  gcacttctgatcctagctcttgttggagc
tgcagttgctgactacaaagacgatgacgacaagctt atg acaacctcactagatacagttgagacctttg
gtaccacatcctactatgatgacgtgggcctgctctgtgaaaaagctgataccagagcactgatggccag
tttgtgccccgctgtactccctggtgttcactgtgggcctcttgggcaatgtggtggtggtgatgatcct
cataaaatacaggaggctccgaattatgaccaacatctacctgctcaacctggccatttcggacctgctct
tcctcgtcacccttccattctggatccactatgtcaggggcataactgggttttggccatggcatgtgt
aagctcctctcagggttttatcacacaggcttgtacagcgagatcttttcataatcctgctgacaatcga
caggtacctggccattgtccatgctgtgtttgcccttcgagcccggactgtcacttttggtgtcatcacca
gcatcgtcacctggggcctggcagtgctagcagctcttcctgaatttatcttctatgagactgaagagttg
tttgaagagactctttgcagtgctctttacccagaggatacagtatatagctggaggcatttccacactct
gagaatgaccatcttctgtctcgttctccctctgctcgttatggccatctgctacacaggaatcatcaaaa
cgctgctgaggtgccccagtaaaaaaaagtacaaggccatccggctcatttttgtcatcatggcggtgttt
ttcatttctggacaccctacaatgtggctatccttctctcttcctatcaatccatcttatttggaaatga
ctgtgagcggagcaagcatctggacctggtcatgctggtgacagaggtgatcgcctactccactgctgca
tgaacccggtgatctacgcctttgttggagagaggttccggaagtacctgcgccacttcttccacaggcac
ttgctcatgcacctgggcagatacatcccattccttcctagtgagaagctggaaagaaccagctctgtctc
tccatccacagcagagccggaactctctattgtgttt tag ctaga
                                        ↑    ↖XbaI cloning site
                                   Stop codon of human CCR3
```

Peptide Sequence Comparisons of Human CCR3 with CCR3/2 and CCR2 isoform b

```
                *         20         *         40         *         60         *
huCCR32   : ~~~~~~~~~~MTTSLDTVETFGTTSYD-DVGLLICEKADTRALMAQPVPPLYSIVFTVGLLIGNVVVVMILIKYRRLRIMT :  69
huCCR3    : ~~~~~~~~~~MTTSLDTVETFGTTSYD-DVGLLICEKADTRALMAQPVPPLYSIVFTVGLLIGNVVVVMILIKYRRLRIMT :  69
CCR2RisoB : MLSTSRSRFIRNTNESGEE---VTTFFDYDYGAPCHKFDVKQIGAQLLPPLYSIVFIFGFVGNMIVVLILINQKKLKCLT :  77

*        100         *        120         *        140         *
huCCR32   : NIYLLNLAISDLLFLVTLPFWIHYVRGHNWVFGHGMCKLLSGFYHTGLYSEIFFIILLTIDRYLAIVHAVFALRARTVT : 148
huCCR3    : NIYLLNLAISDLLFLVTLPFWIHYVRGHNWVFGHGMCKLLSGFYHTGLYSEIFFIILLTIDRYLAIVHAVFALRARTVT : 148
CCR2RisoB : DIYLLNLAISDLLFLITLPLWAHSA-ANEWVFGNAMCKLFTGLYHIGYFGGIFFIILLTIDRYLAIVHAVFALKARTVT : 155

*        180         *        200         *        220         *
huCCR32   : FGVITSIVTWGLAVIAALPEFIFYETEELFEETLCSALYPEDTVYSWRHFHTLRMTIFCIVLPLLVMAICYTGIIKTLL : 227
huCCR3    : FGVITSIVTWGLAVIAALPEFIFYETEELFEETLCSALYPEDTVYSWRHFHTLRMTIFCIVLPLLVMAICYTGIIKTLL : 227
CCR2RisoB : FGVVTSVITWLVAVFASVPGLLIFTKCQKEDSVYVCGPYFPR----GWNNFHTIMRNILGLVLPLLIMVICYSGILKTLL : 230

*        260         *        280         *        300         *
huCCR32   : RCPS-KKKYKAIRLIFVIMAVFFIFWTPYNVALLLSSYQSILFGNDCERSKHLDLVMLVTEVIAYSHCCMNPVIYAFVG : 305
huCCR3    : RCPS-KKKYKAIRLIFVIMAVFFIFWTPYNVALLLSSYQSILFGNDCERSKHLDLVMLVTEVIAYSHCCMNPVIYAFVG : 305
CCR2RisoB : RCRNEKKRHRAVRVIFTIMIVYFLFWTPYNIVILLNTFQEFFGLSNCESTSQLDQATQVTETLGMTHCCINPIIYAFVG : 309

CCR3/2 splice
                *        340         *        360
huCCR32   : ERFRKYLSVFFRKHITKRFCKQCPVFYRETVDGVTSTNTPSTGEQEVSAGL* : 356
huCCR3    : ERFRKYLRHFFHRHLLMHLGRYIPFLPSEKLER-TSSVSPSTAEPELSIVF* : 355
CCR2RisoB : EKFRRYLSVFFRKHITKRFCKQCPVFYRETVDGVTSTNTPSTGEQEVSAGL~ : 360
```

FIG. 3B

Titration of eotaxin on human eosinophils

Lane 1–7: eotaxin (nM): 0,3,10,30,100,300 and 1000

Titration of eotaxin on CHO/huCCR3-2

Lane 1–7: eotaxin (nM): 0,3,10,30,100,300 and 1000

```
CCR23   :  ATGCTGTCCACATCTCGTTCTCGGTTTATCAGAAATACCAACGACAGCGGTCAAGAAGTCACCACCTTTTTCAT :   75
huCR2B  :  ATGCTGTCCACATCTCGTTCTCGGTTTATCAGAAATACCAACGACAGCGGTCAAGAAGTCACCACCTTTTTCAT :   75
                  20        *        40        *        60        *

CCR23   :  TATGATTACGGTGCTCCCTGTCATAAATTTGACGTGAAGCAAATTGGGGCCCAACTCCTGCCTCCGCTCTACTCG :  150
huCR2B  :  TATGATTACGGTGCTCCCTGTCATAAATTTGACGTGAAGCAAATTGGGGCCCAACTCCTGCCTCCGCTCTACTCG :  150
                 80        *       100        *       120        *       140

CCR23   :  CTGGTGTTCATCTTTGGTTTTGTGGGCAACATGCTGGTCTCCTCATCTTAATAAACTGCAAAAAGCTGAAGTGC :  225
huCR2B  :  CTGGTGTTCATCTTTGGTTTTGTGGGCAACATGCTGGTCTCCTCATCTTAATAAACTGCAAAAAGCTGAAGTGC :  225
                         160        *       180        *       200        *       220

CCR23   :  TTCACTGACATTTACCTGCTCAACCTGGCCATCTCTGATCTCTGCTTTTTCTTATTACTCTCCCATTGTGGGCTCAC :  300
huCR2B  :  TTCACTGACATTTACCTGCTCAACCTGGCCATCTCTGATCTCTGCTTTTTCTTATTACTCTCCCATTGTGGGCTCAC :  300
               240        *       260        *       280        *       300

CCR23   :  TCTGCTGCAAATGAGTGGGTCTTTGGCAATGTGCAATTGTCCAAATTATTCACAGAGGCTGTATCACATCGTTATTT :  375
huCR2B  :  TCTGCTGCAAATGAGTGGGTCTTTGGCAATGTGCAATTGTCCAAATTATTCACAGAGGCTGTATCACATCGTTATTT :  375
                      320        *       340        *       360        *

CCR23   :  GGCGGAATCTTCTTCATCATGGTGGTCACAATGCATACAATACGTGGGTATTGTCCATGGTGTGTTGGTTTAAAA :  450
huCR2B  :  GGCGGAATCTTCTTCATCATGGTGGTCACAATGCATACAATACGTGGGTATTGTCCATGGTGTGTTGGTTTAAAA :  450
                380        *       400        *       420        *       440

CCR23   :  GCCAGGAGGGTCACCTTTGGGGTGGTGGTCACAAGTGTCATCACCTGGTCATCACCTGTTGGTGGCTGTGTTGCTTCTGTCCCAGCA :  525
huCR2B  :  GCCAGGAGGGTCACCTTTGGGGTGGTGGTCACAAGTGTCATCACCTGGTCATCACCTGTTGGTGGCTGTGTTGCTTCTGTCCCAGCA :  525
                       460        *       480        *       500        *       520
```

```
CCR23   : MLSTSRSRFIRNTNESGFFVTTFFDYDYGAFCHEFIVKQIGAQLLFPLYSLVFIFGFVGNMIVVLILINCEKLKCLTD   : 78
huCR2B  : MLSTSRSRFIRNTNESGFFVTTFFDYDYGAFCHEFIVKQIGAQLLFPLYSLVFIFGFVGNMIVVLILINCEKLKCLTD   : 78

CCR23   : IYLLNIAISDLLFLITLFIVAHEAANEPVPGNAMCKLFTGLYHIGYFGGIFFILLTILRYIAIVEAVFAIEARTVTF   : 156
huCR2B  : IYLLNIAISDLLFLITLFIVAHEAANEPVPGNAMCKLFTGLYHIGYFGGIFFILLTILRYIAIVEAVFAIEARTVTF   : 156

CCR23   : GNVTEVITWLVAVFAEVFGIIFTKCQKEDENVNCGPYFPRGWNNFHTIMRNILGIVLFLLINVICYSGILETLLRCRN   : 234
huCR2B  : GNVTEVITWLVAVFAEVFGIIFTKCQKEDENVNCGPYFPRGWNNFHTIMRNILGIVLFLLINVICYSGILETLLRCRN   : 234

CCR23   : EKKRHFFVRVIFTINIVYFLFWTPYNIVILLNTFQEFFGLSNCESTSQLDQATGVTFTLGMTHCCINPIIYAFVGEKF   : 312
huCR2B  : EKKRHFFVRVIFTINIVYFLFWTPYNIVILLNTFQEFFGLSNCESTSQLDQATGVTFTLGMTHCCINPIIYAFVGEKF   : 312

CCR23   : RRYLRHFFHRHLIMHLGRYIPFLPSEKLER-TSSVSPSTAEPELSIVF*    : 359
huCR2B  : RRYLSVFFRKHITKRFCKQCPVEYRETMDGVTSTNTPSTGEQEVSAGL~    : 360

Sequences merged at middle of Y residue, aa
315 of 359
```

FIG. 8B

SEQUENCE LISTING

<160> NUMBER OF SEQ ID NOS: 25

<210> SEQ ID NO 1
<211> LENGTH: 10073
<212> TYPE: DNA
<213> ORGANISM: Homo sapiens

<400> SEQUENCE: 1

| | | | | | |
|---|---|---|---|---|---|
| gtttatgaaa | ttacagggct | ggagacaaag | atcacaatgt | gaagacaaaa | ttggagagcg | 60 |
| gtcctaatca | gccagagcaa | aatttctggc | tcttgctctt | ccccatcctg | ggttgaatca | 120 |
| taggaacagg | tggcaagatg | ccagggtcag | gagattccag | aagtggcagc | aagctcagtg | 180 |
| ttaccaggtc | agggatgacc | tgtcttatta | ttgaaatctc | agagatatgc | tccaattccg | 240 |
| gcccagagac | acattgagag | acaactgggg | aacttgctat | gttcctgaac | aggcaatgag | 300 |
| ctgtcttcca | agaaaaaacc | tgagaccctt | caagtctcag | gtcttactta | gcacatatac | 360 |
| caggtcttac | acaggacaca | tggttacaac | tgactgaaat | ctgggctggg | tgtaggagct | 420 |
| cacacctgta | atcccagccc | ttcaggaggc | tgaggcaggc | agattgcctg | agcccaggag | 480 |
| ttcgagacca | gcccgggcaa | catgacaaaa | ccccatctct | acaaaaaata | gtcaggcatg | 540 |
| gtggcatgca | cctgtagtct | cagctacttg | ggaggctgag | atgagaggat | tgcttgaggt | 600 |
| tgagactgca | gtgaagcatg | atcatgccac | cgcactccag | cctaggcaac | agagcaagat | 660 |
| cttgtcgcaa | aagaaagcaa | aaacacaaca | taacacaaca | acaacaacaa | caacaacaac | 720 |
| agcaaaaaag | ccaacttctt | gaaatctgga | aggacacct | ggactgccct | gagcatttga | 780 |
| ttgttgttgg | ctctagcagt | ggatgcatcc | ttcaacctct | ggcactctgc | agggctcaga | 840 |
| ctgttctgtt | ctgtttgtta | cctgtggagt | gcctgccaga | ccctgctcta | gctgctttag | 900 |
| gtccatttac | cctcatagac | ccccagtctt | gttattcata | tttcatattt | gggaaatgga | 960 |
| aacttagaaa | cttgccaagt | ccacagcatg | agatcctgcc | tccggtgtct | gctggattcc | 1020 |
| agaaagtgcc | aggggccaac | ttagatgaca | ccatgttctc | tgcacaatct | taggaatgct | 1080 |
| cctagtctga | tgtccccatt | gcaaaattta | cattatcttt | taacaaaacg | tctttccaag | 1140 |
| gagggcatt | taaataact | gaggttcttc | ttgctaagga | agttcctgac | acaagagata | 1200 |
| atttagcatt | tccttttcat | taaaaagttt | gaaatcctgt | aatttgtgat | aatgtggatg | 1260 |
| aacctagagg | atgttaagtg | aaataagcca | cacacagata | gacaaatacc | acgtgatctc | 1320 |
| actcttatgt | ggaattttt | tttaaataag | ttgcttagcc | gggcatgatg | gcacacacct | 1380 |
| gtaatcctag | ctactcagga | ggctgaggtg | ggaggatggc | ttgaactcag | aaggtggagg | 1440 |
| ttgcagtgag | ctgagactgt | gccagtgcac | tccggtctgg | gtgacagaat | gaaacccaat | 1500 |
| ttaaaaaaaa | aaaaaagtt | gctatcttag | aaaaagacag | tagagcagtg | gttaccagag | 1560 |
| actggggagg | aaagagagga | ggtgagaatg | ggcagcagtt | gatcaacggg | tacaaagtta | 1620 |
| ccatgagata | ggagaaacaa | gtgctggtgc | tctgctccaa | gtagggtgac | ggtagttaat | 1680 |
| aatgaattct | gtatatataa | atagctagaa | gagagggttt | tcaatatcat | tattatttca | 1740 |
| aaagaaatga | taaatgtttc | agaggatgga | tatgtaatta | ccctgatttg | atcattgcac | 1800 |
| aatgtataca | tgtagcaaaa | catcacattg | tgtcccataa | atatatacaa | ttattatgtg | 1860 |
| aattaaataa | aaaaaatt | taaagtctta | tctaaatgaa | atttctaacc | agattctgaa | 1920 |
| tccatgatac | cactgaaacc | agcacacatg | atcgcagtaa | aacctcatta | tacttcctcc | 1980 |
| actatcacca | ataccctta | ttctctggaa | catgaaacat | tctgttgtgc | tcatatcatg | 2040 |

-continued

| | |
|---|---|
| caaattatca ctagtaggag agcagagagt ggaaatgttc caggtataaa gacccacaag | 2100 |
| ataaagaagc tcagagtcgt tagaaacagg agcagatgta cagggtttgc ctgactcaca | 2160 |
| ctcaaggttg cataagcaag atttcaaaat taatcctatt ctggagacct caacccaatg | 2220 |
| tacaatgttc ctgactggaa agaagaact atattttct gatttttttt tttcaaatct | 2280 |
| ttaccattag ttgccctgta tctccgcctt cactttctgc aggaaacttt atttcctact | 2340 |
| tctgcatacc aagtttctac ctctagatct gtttggttca gttgctgaga agcctgacat | 2400 |
| accaggactg cctgagacaa gccacaagct ggtgagttgt aggcatttt tccattactt | 2460 |
| tctgattcat aggctcaacg cacctcaaag ctggaaatgc cgggtctggg tacaccctgg | 2520 |
| ggaactgcaa agcctgcaca cttgggggga atgatcaaga tgagaggcag gggtggggat | 2580 |
| ggcatgtgca ccaggagatg ttagagaaac cctgaggaag agcagcgtgc agcaggtgat | 2640 |
| gggggagagt gggcagcaag cgaggccagg acagccactc tgctcagtca ccagtccaca | 2700 |
| cacccagggg ctcactctgc ccctctgagc acccaaggac gttaaagagc tggaactgtt | 2760 |
| agtctaaata taggaccatc caagctctga accaaaatgt gtcccttgcc tcaactcagg | 2820 |
| agatccacag aggcagaagt aaggaattta ttttctgaaa gatagatttc tatcagttct | 2880 |
| gggtgacatg ttctgacact tgaaatgaca cctaggacag cacatttcag gcatcttgct | 2940 |
| cattgttcac tgtagtagaa gctacatgct agccagttgt aaaaatgaaa ttaagtaatg | 3000 |
| tgtgcacagc atttaacata gcatctgagc ttcaggagca ctcaattaat gaccacagtt | 3060 |
| gtgattcttt aggcagatgc atttttttcc aactttgatc agaggtctta tttagcttct | 3120 |
| ccagatttca agaatctggc tcagtgatat gaaatacaag acttgtgaaa agtgtcaatt | 3180 |
| gcaagagaaa tggaaggata aagtatacag gtgggtggaa agaaaattca cagtcactgc | 3240 |
| cagaaaaaa attcttgaga atcaagtcct gatgatgtta gggcttatag ttcttattat | 3300 |
| aaaagagtttt atgtactcat tcagtgaaca tttattggtg cctcctttag ccaggtacta | 3360 |
| tcataagagc tgaaaataga agcataatcc agtccttgat cttgaggaac atgctgtgtg | 3420 |
| tagcagataa cataataagt gcttatctag atgcatgcag tgttatgtga taagagtaat | 3480 |
| atgacagagg atacagatta ggcttcacag agaagggga tttgagcagg aggtattgaa | 3540 |
| gggtgaatag aagctcacca atcatttgg gcagaggggc aaggacctgc aaaaccactg | 3600 |
| aagcatgaag gaaatggtga gtttagggaa aatgaagaga agatggctgt gactgaagca | 3660 |
| caggatttgg gattggagaa gggactggag gtgaggctga aaagaggcaa actcagaaaa | 3720 |
| gatgttgtgc tgggcagtct ggacattatc tttgaagccc accacatata agtcataggg | 3780 |
| ctactggagg ttttaagcta agagtgacta ttcaatttca acttaagaga gataggttg | 3840 |
| agagggaaca tggcttgaga tgagccatga gcaaaggaaa gactacaaca aagccaggag | 3900 |
| tgaggagtgt gtgaagcaag aaagtgacag ttgaaagcag tgcagagggg atgaatctga | 3960 |
| gaggcatcta tgaggtggaa ctcaaatgac atgataataa tacagggcat ttctctgtgt | 4020 |
| cagatgctgt cctaagtcct tactccattg atcttcacag caactcagca tagttaatat | 4080 |
| tttatgcata agaaatcgg cacttgaagg agtaattggc cccagattac actgcctata | 4140 |
| aggattcaaa tccaggtttg tttggctcca aaaactggct cctaattttc agaaggagaa | 4200 |
| gcgacccagg gcaatgccca attttgcttc ttaggcaatg gaggaatcca caatcggaag | 4260 |
| gagttttcag cagtgcccca tttggggtgg gttgaatttg aggtccctgc atgatacccA | 4320 |
| cttttgctcac ttcagtgcct aaaactgagt atggttcata gtaggtgttc aataagtgtt | 4380 |

```
gatgcagtga atacatgcat ggggagatat gcatcaggca atgggaaatt caactctaag    4440
gcttagggga aagctggagc ttgaagacag agctttagaa aacagtagca tagaagggag    4500
taggaaccat gagtttagac aatacaattc aggaagaact ttgtagcaag gataaagagg    4560
caaaaaatta aagaggtgag agctaagtgt ggtgcctggg gaatcttaag gtgtgggcac    4620
ggggaggaga tgccagcaaa gaacatgaat aaaaagcggt agcacagccc ctcccatctg    4680
gaagccaaaa agaattgtaa atggaggaag ttagcagaag gatcaaatac ttgaagaggg    4740
tggaattgga ataaaaccag gcatttgaa aaattgggtt gtcactgcaa tcttaacaag    4800
agaagttttg gcaggatgat ggaggcagaa agctgagaga atcatcagtt agaacgtttt    4860
tgacttcaga gaacagaaaa tgcagttcat aatggcttta aaacaggggc ttgttttttct    4920 cccagcaatt tgagaggcca aggcgggtgc atcaggaggt caagagaccg agaccatcct    4980
ggccaacatg gtgaatcccc atctctacta aaaatacaaa aattagcggg gcatggtggt    5040
gcacgcctat agtcccatct actcaggagg ctgaggcagg agaatcactt gaacccagga    5100
ggtggaggtt gcagtgagct gagatcatgg ccactgcact atagcctgga gacacagcga    5160
gactccgtct ccaaaaaaaa aaaaaagaa ggcagaaggt gaatagttca agggtgggtt    5220
taggactcag tgataatagg attctgcctg gcttctcatg gttctctagg tcttccattc    5280
atggcaccat gccctcacta ggcatgctgc cagagcagga ggggcaggtg gagggttctc    5340
ttgtgtctgt cttatcaggg aagaagagct ttctcagaag ccccccagcag actcccttt    5400 catattatgg tccagcaatg agtcacagac ctatgcacca cctgcaaagg agccagagaa    5460
aacaaacgcc cagcgctttt agcctgaaaa tgagaatctg gtttgctggg aagataaag    5520 ggtgtcggaa aatggctgtt gggtaaatca ttgatgtctg ccactaggaa tgaaaggcaa    5580
atcaggaact ggcacacatg ctttcaggga gatggctgca agggagaggg caaagactgg    5640
gaagttgctt atgtggtgcc agactatttg gaagatcatg gattgcggtg tttgtgttgt    5700
gtggtcatca ttttgttctt tgtttacaga acagagaaag tggattgaac aaggacgcat    5760
ttccccagta catccacaac atgctgtcca catctcgttc tcggtttatc agaaatacca    5820
acgagagcgg tgaagaagtc accaccttt ttgattatga ttacggtgct ccctgtcata    5880
aatttgacgt gaagcaaatt ggggcccaac tcctgcctcc gctctactcg ctggtgttca    5940
tctttggttt tgtgggcaac atgctggtcg tcctcatctt aataaactgc aaaaagctga    6000
agtgcttgac tgacatttac ctgctcaacc tggccatctc tgatctgctt tttcttatta    6060
ctctcccatt gtgggctcac tctgctgcaa atgagtgggt ctttgggaat gcaatgtgca    6120
aattattcac agggctgtat cacatcggtt attttggcgg aatcttcttc atcatcctcc    6180
tgacaatcga tagatacctg gctattgtcc atgctgtgtt tgctttaaaa gccaggacgg    6240
tcacctttgg ggtggtgaca agtgtgatca cctggttggt ggctgtgttt gcttctgtcc    6300
caggaatcat ctttactaaa tgccagaaag aagattctgt ttatgtctgt ggcccttatt    6360
ttccacgagg atggaataat ttccacacaa taatgaggaa catttgggg ctggtcctgc    6420 cgctgctcat catggtcatc tgctactcgg gaatcctgaa aacctgctt cggtgtcgaa    6480 acgagaagaa gaggcatagg gcagtgagag tcatcttcac catcatgatt gtttactttc    6540
tcttctggac tccctataat attgtcattc tcctgaacac cttccaggaa ttcttcggcc    6600
tgagtaactg tgaaagcacc agtcaactgg accaagccac gcaggtgaca gagactcttg    6660
ggatgactca ctgctgcatc aatcccatca tctatgcctt cgttggggag aagttcagaa    6720
ggtatctctc ggtgttcttc cgaaagcaca tcaccaagcg cttctgcaaa caatgtccag    6780
```

```
ttttctacag ggagacagtg gatggagtga cttcaacaaa cacgccttcc actggggagc    6840
aggaagtctc ggctggttta taaaacgagg agcagtttga ttgttgttta taagggaga    6900 taacaatctg tatataacaa caaacttcaa gggtttgttg aacaatagaa acctgtaaag    6960
caggtgccca ggaacctcag ggctgtgtgt actaatacag actatgtcac ccaatgcata    7020
tccaacatgt gctcagggaa taatccagaa aaactgtggg tagagacttt gactctccag    7080
aaagctcatc tcagctcctg aaaaatgcct cattaccttg tgctaatcct cttttctag    7140 tcttcataat ttcttcactc aatctctgat tctgtcaatg tcttgaaatc aagggccagc    7200
tggaggtgaa gaagagaatg tgacaggcac agatgaatgg gagtgaggga tagtggggtc    7260
agggctgaga ggagaaggag ggagacatga gcatggctga gcctggacaa agacaaaggt    7320
gagcaaaggg ctcacgcatt cagccaggag atgatactgg tccttagccc catctgccac    7380
gtgtatttaa ccttgaaggg ttcaccaggt cagggagagt ttgggaactg caataacctg    7440
ggagttttgg tggagtccga tgattctctt ttgcataagt gcatgacata ttttgctttt    7500
attacagttt atctatggca cccatgcacc ttacatttga aatctatgaa atatcatgct    7560
ccattgttca gatgcttctt aggccacatc ccctgtcta aaaattcaga aaatttttgt    7620 ttataaaga tgcattatct atgatatgct aatatatgta tatgcaatat atataggctc    7680
ttgcttgatc tctccaggag gtagtgatta tgagaagggg gtggagaatg atgagttcct    7740
tcaccaggag caaaggacgg ggatcgtgtg gaaccactgc agaactattt ccgaaatcaa    7800
ctaagtggag agagccagga aggctgcatc agaacccagt aaagcttctt gtctggatct    7860
gagctggttt gttttgtgct tgcttttccc tgccttgcca ctcccctcac tcttctcttt    7920
tccccacagc cttttcaca tagctcttgg ctgtaggatt gccccactcc aaaaaccagt    7980
gtgtggaggt ccaggagtga gaccaggaaa gaatgtgaaa gtgactacac aaggactcct    8040
cgatggtcgt ggaaaaggaa agtcaattgg cagagcccct gaagccagtc ttcaggacaa    8100
agaaggagcc tagagacaga aatgacagat ctctgctttg gaaatcacac gtctggcttc    8160
acagatgtgt gattcacagt gtgaatcttg gtgtctacgt taccaggcag gaaggctgag    8220
aggagagaga ctccagctgg gttggaaaac agtattttcc aaactacctt ccagttcctc    8280 attttttgaat acaggcatag agttcagact tttttttaaat agtaaaaata aaattaaagc    8340
tgaaaactgc aacttgtaaa tgtggtaaag agttagtttg agttactatc atgtcaaacg    8400
tgaaaatgct gtattagtca cagagataat tctagctttg agcttaagaa ttttgagcag    8460
gtggtatgtt tgggagactg ctgagtcaac ccaatagttg ttgattggca ggagttggaa    8520
gtgtgtgatc tgtgggcaca ttagcctatg tgcatgcagc atctaagtaa tgatgtcgtt    8580
tgaatcacag tatacgctcc atcgctgtca tctcagctgg atctccattc tctcaggctt    8640
gctgccaaaa gccttttgtg ttttgttttg tatcattatg aagtcatgcg tttaatcaca    8700
ttcgagtgtt tcagtgcttc gcagatgtcc ttgatgctca tattgttccc tattttgcca    8760
gtgggaactc ctaaatcaag ttggcttcta atcaaagctt ttaaaccta ttggtaaaga    8820 atggaaggtg gagaagctcc ctgaagtaag caaagacttt cctcttagtc gagccaagtt    8880
aagaatgttc ttatgttgcc cagtgtgttt ctgatctgat gcaagcaaga aacactgggc    8940
ttctagaacc aggcaacttg ggaactagac tcccaagctg gactatggct ctactttcag    9000 gcccacatggc taaagaaggt ttcagaaaga agtggggaca gagcagaact ttcaccttca    9060
tatatttgta tgatcctaat gaatgcataa aatgttaagt tgatggtgat gaaatgtaaa    9120
```

-continued

```
tactgttttt aacaactatg atttggaaaa taaatcaatg ctataactat gttgataaaa    9180
gatttaaaaa caactggctg ttttttttaca ctgtggtgtg aagattgtg ttgtgttcac     9240 aacttttcac ttcttcccct gtgtgattac acacacctgc ccttgtggtg tgacttgcag    9300
tgcgccctac aggccacaca accccatgcc ctccaccact ggctctgctg ctggaatgtg    9360
agcagaagtg acatctgcct catccaagca gagcctcttg ctcagccaca ggaaggccca    9420
ttccagatca cacccgtcag cccgtgcgcc ctggtgaatg agaagacaca gggagctgca    9480
gccacatata acatgagcaa gaagtctgtg tttgctgtga taagccactg agttttaggg    9540
gttgtttgtt aagaagcaca aaaaccgatt aagacatgtg gtatatagtg acttcatata    9600
tagaatctgg aaaactatcc atttattttc aatcatggaa ttcaatatga caagcatccc    9660
ggagggtcta cctatgccag actgggttgg aaacagaaag acagatgtta atgccagtgt    9720
cctttacacc tccaagtcca gggccagctg tggagtggga ggggtagaga aggtcctgtg    9780
cacagtcaca gtgcgctgtg cagagcagga acagaggcat ctgtgaaaag tgctgagagc    9840
ctggaggaca gagtgactaa tgcaatgaca gtcttgcatc ataggaataa cagccacagc    9900
aggattttat tgctgccaaa gaaactgcca tttaaaaatt gccagccatc cgggaggctg    9960
aggcaggaga atggcatgaa tccaggaggc ggagcttgca gtgagccgag atcgggccac   10020
tgcactccag cctgggcaac agagccagac tccatctcaa aaaaaaaaaa aaa          10073
```

<210> SEQ ID NO 2
<211> LENGTH: 374
<212> TYPE: PRT
<213> ORGANISM: Homo sapiens

<400> SEQUENCE: 2

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205
```

```
Leu Gly Leu Val Leu Pro Leu Ile Met Val Ile Cys Tyr Ser Gly
    210                 215                 220
Ile Leu Lys Thr Leu Leu Arg Cys Arg Asn Glu Lys Lys Arg His Arg
225                 230                 235                 240
Ala Val Arg Val Ile Phe Thr Ile Met Ile Val Tyr Phe Leu Phe Trp
                245                 250                 255
Thr Pro Tyr Asn Ile Val Ile Leu Leu Asn Thr Phe Gln Glu Phe Phe
            260                 265                 270
Gly Leu Ser Asn Cys Glu Ser Thr Ser Gln Leu Asp Gln Ala Thr Gln
        275                 280                 285
Val Thr Glu Thr Leu Gly Met Thr His Cys Cys Ile Asn Pro Ile Ile
    290                 295                 300
Tyr Ala Phe Val Gly Glu Lys Phe Arg Ser Leu Phe His Ile Ala Leu
305                 310                 315                 320
Gly Cys Arg Ile Ala Pro Leu Gln Lys Pro Val Cys Gly Gly Pro Gly
                325                 330                 335
Val Arg Pro Gly Lys Asn Val Lys Val Thr Thr Gln Gly Leu Leu Asp
            340                 345                 350
Gly Arg Gly Lys Gly Lys Ser Ile Gly Arg Ala Pro Glu Ala Ser Leu
        355                 360                 365
Gln Asp Lys Glu Gly Ala
    370

<210> SEQ ID NO 3
<211> LENGTH: 1979
<212> TYPE: DNA
<213> ORGANISM: Homo sapiens

<400> SEQUENCE: 3
caggactgcc tgagacaagc cacaagctga acagagaaag tggattgaac aaggacgcat      60
ttccccagta catccacaac atgctgtcca catctcgttc tcggtttatc agaaatacca     120
acgagagcgg tgaagaagtc accacctttt ttgattatga ttacggtgct ccctgtcata     180
aatttgacgt gaagcaaatt ggggcccaac tcctgcctcc gctctactcg ctggtgttca     240
tctttggttt tgtgggcaac atgctggtcg tcctcatctt aataaactgc aaaaagctga     300
agtgcttgac tgacatttac ctgctcaacc tggccatctc tgatctgctt tttcttatta     360
ctctcccatt gtgggctcac tctgctgcaa atgagtgggt ctttgggaat gcaatgtgca     420
aattattcac agggctgtat cacatcggtt attttggcgg aatcttcttc atcatcctcc     480
tgacaatcga tagatacctg gctattgtcc atgctgtgtt tgctttaaaa gccaggacgg     540
tcacctttgg ggtggtgaca agtgtgatca cctggttggt ggctgtgttt gcttctgtcc     600
caggaatcat ctttactaaa tgccagaaag aagattctgt ttatgtctgt ggcccttatt     660
ttccacgagg atgaataat ttccacacaa taatgaggaa catttggggg ctggtcctgc     720
cgctgctcat catggtcatc tgctactcgg gaatcctgaa aaccctgctt cggtgtcgaa     780
acgagaagaa gaggcatagg gcagtgagag tcatcttcac catcatgatt gtttactttc     840
tcttctggac tccctataac attgtcattc tcctgaacac cttccaggaa ttcttcggcc     900
tgagtaactg tgaaagcacc agtcaactgg accagccac gcaggtgaca gagactcttg     960
ggatgactca ctgctgcatc aatcccatca tctatgcctt cgttgggag aagttcagaa    1020
ggtatctctc ggtgttcttc gaaagcaca tcaccaagcg cttctgcaaa caatgtccag    1080
ttttctacag ggagacagtg gatggagtga cttcaacaaa cacgccttcc actggggagc    1140
```

-continued

```
aggaagtctc ggctggttta taaaacgagg agcagtttga ttgttgttta taagggaga    1200 taacaatctg tatataacaa caaacttcaa gggtttgttg aacaatagaa acctgtaaag    1260
caggtgccca ggaacctcag ggctgtgtgt actaatacag actatgtcac ccaatgcata    1320
tccaacatgt gctcagggaa taatccagaa aaactgtggg tagagacttt gactctccag    1380
aaagctcatc tcagctcctg aaaaatgcct cattaccttg tgctaatcct cttttctag    1440 tcttcataat ttcttcactc aatctctgat tctgtcaatg tcttgaaatc aagggccagc    1500
tggaggtgaa gaagagaatg tgacaggcac agatgaatgg gagtgaggga tagtggggtc    1560
agggctgaga ggagaaggag ggagacatga gcatggctga gcctggacaa agacaaaggt    1620
gagcaaaggg ctcacgcatt cagccaggag atgatactgg tccttagccc catctgccac    1680
gtgtatttaa ccttgaaggg ttcaccaggt caggagagt ttgggaactg caataacctg    1740
ggagttttgg tggagtccga tgattctctt ttgcataagt gcatgacata tttttgcttt    1800
attacagttt atctatggca cccatgcacc ttacatttga aatctatgaa atatcatgct    1860
ccattgttca gatgcttctt aggccacatc ccctgtcta aaaattcaga aattttgt       1920 ttataaaaga tgcattatct atgatatgct aatatatgta tatgcaatat aaaatttag    1979
```

<210> SEQ ID NO 4
<211> LENGTH: 360
<212> TYPE: PRT
<213> ORGANISM: Homo sapiens

<400> SEQUENCE: 4

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
    210                 215                 220

Ile Leu Lys Thr Leu Leu Arg Cys Arg Asn Glu Lys Lys Arg His Arg
```

|     | 225 |     |     |     | 230 |     |     |     |     | 235 |     |     |     |     | 240 |
| --- | --- | --- | --- | --- | --- | --- | --- | --- | --- | --- | --- | --- | --- | --- | --- |

Ala Val Arg Val Ile Phe Thr Ile Met Ile Val Tyr Phe Leu Phe Trp
                      245                          250                          255

Thr Pro Tyr Asn Ile Val Ile Leu Leu Asn Thr Phe Gln Glu Phe Phe
           260                        265                      270

Gly Leu Ser Asn Cys Glu Ser Thr Ser Gln Leu Asp Gln Ala Thr Gln
          275                        280                      285

Val Thr Glu Thr Leu Gly Met Thr His Cys Cys Ile Asn Pro Ile Ile
    290                        295                      300

Tyr Ala Phe Val Gly Glu Lys Phe Arg Arg Tyr Leu Ser Val Phe Phe
305                      310                      315                      320

Arg Lys His Ile Thr Lys Arg Phe Cys Lys Gln Cys Pro Val Phe Tyr
                    325                      330                      335

Arg Glu Thr Val Asp Gly Val Thr Ser Thr Asn Thr Pro Ser Thr Gly
          340                        345                      350

Glu Gln Glu Val Ser Ala Gly Leu
          355                        360

<210> SEQ ID NO 5
<211> LENGTH: 1201
<212> TYPE: DNA
<213> ORGANISM: Homo sapiens

<400> SEQUENCE: 5

| | | | | |
|---|---|---|---|---|
| tttttcttct | tctatcacag | ggagaagtga | aatgacaacc | tcactagata cagttgagac | 60 |
| ctttggtacc | acatcctact | atgatgacgt | gggcctgctc | tgtgaaaaag ctgataccag | 120 |
| agcactgatg | gcccagtttg | tgccccgct | gtactccctg | tgttcactg tgggcctctt | 180 |
| gggcaatgtg | gtggtggtga | tgatcctcat | aaaatacagg | aggctccgaa ttatgaccaa | 240 |
| catctacctg | ctcaacctgg | ccatttcgga | cctgctcttc | ctcgtcaccc ttccattctg | 300 |
| gatccactat | gtcagggggc | ataactgggt | ttttggccat | ggcatgtgta agctcctctc | 360 |
| agggttttat | cacacaggct | tgtacagcga | gatcttttc | ataatcctgc tgacaatcga | 420 |
| caggtacctg | gccattgtcc | atgctgtgtt | tgcccttcga | gcccggactg tcacttttgg | 480 |
| tgtcatcacc | agcatcgtca | cctgggggcct | ggcagtgcta | gcagctcttc ctgaatttat | 540 |
| cttctatgag | actgaagagt | tgtttgaaga | gactctttgc | agtgctcttt acccagagga | 600 |
| tacagtatat | agctggaggc | atttccacac | tctgagaatg | accatcttct gtctcgttct | 660 |
| ccctctgctc | gttatggcca | tctgctacac | aggaatcatc | aaaacgctgc tgaggtgccc | 720 |
| cagtaaaaaa | aagtacaagg | ccatccggct | cattttttgtc | atcatggcgg tgttttcat | 780 |
| tttctggaca | ccctacaatg | tggctatcct | tctctcttcc | tatcaatcca tcttatttgg | 840 |
| aaatgactgt | gagcggagca | agcatctgga | cctggtcatg | ctggtgacag aggtgatcgc | 900 |
| ctactcccac | tgctgcatga | acccggtgat | ctacgccttt | gttggagaga ggttccggaa | 960 |
| gtacctgcgc | cacttcttcc | acaggcactt | gctcatgcac | ctgggcagat acatcccatt | 1020 |
| ccttcctagt | gagaagctgg | aaagaaccag | ctctgtctct | ccatccacag cagagccgga | 1080 |
| actctctatt | gtgttttagg | tcagatgcag | aaaattgcct | aaagaggaag gaccaaggag | 1140 |
| atgaagcaaa | cacattaagc | cttccacact | cacctctaaa | acagtccttc aaacttccag | 1200 |
| t | | | | | 1201 |

<210> SEQ ID NO 6
<211> LENGTH: 355

<212> TYPE: PRT
<213> ORGANISM: Homo sapiens

<400> SEQUENCE: 6

```
Met Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
                20                  25                  30

Met Ala Gln Phe Val Pro Pro Leu Tyr Ser Leu Val Phe Thr Val Gly
                35                  40                  45

Leu Leu Gly Asn Val Val Val Met Ile Leu Ile Lys Tyr Arg Arg
50                  55                  60

Leu Arg Ile Met Thr Asn Ile Tyr Leu Leu Asn Leu Ala Ile Ser Asp
65                  70                  75                  80

Leu Leu Phe Leu Val Thr Leu Pro Phe Trp Ile His Tyr Val Arg Gly
                85                  90                  95

His Asn Trp Val Phe Gly His Gly Met Cys Lys Leu Leu Ser Gly Phe
                100                 105                 110

Tyr His Thr Gly Leu Tyr Ser Glu Ile Phe Phe Ile Ile Leu Leu Thr
                115                 120                 125

Ile Asp Arg Tyr Leu Ala Ile Val His Ala Val Phe Ala Leu Arg Ala
130                 135                 140

Arg Thr Val Thr Phe Gly Val Ile Thr Ser Ile Val Thr Trp Gly Leu
145                 150                 155                 160

Ala Val Leu Ala Ala Leu Pro Glu Phe Ile Phe Tyr Glu Thr Glu Glu
                165                 170                 175

Leu Phe Glu Glu Thr Leu Cys Ser Ala Leu Tyr Pro Glu Asp Thr Val
                180                 185                 190

Tyr Ser Trp Arg His Phe His Thr Leu Arg Met Thr Ile Phe Cys Leu
                195                 200                 205

Val Leu Pro Leu Leu Val Met Ala Ile Cys Tyr Thr Gly Ile Ile Lys
                210                 215                 220

Thr Leu Leu Arg Cys Pro Ser Lys Lys Lys Tyr Lys Ala Ile Arg Leu
225                 230                 235                 240

Ile Phe Val Ile Met Ala Val Phe Phe Ile Phe Trp Thr Pro Tyr Asn
                245                 250                 255

Val Ala Ile Leu Leu Ser Ser Tyr Gln Ser Ile Leu Phe Gly Asn Asp
                260                 265                 270

Cys Glu Arg Ser Lys His Leu Asp Leu Val Met Leu Val Thr Glu Val
                275                 280                 285

Ile Ala Tyr Ser His Cys Cys Met Asn Pro Val Ile Tyr Ala Phe Val
                290                 295                 300

Gly Glu Arg Phe Arg Lys Tyr Leu Arg His Phe Phe His Arg His Leu
305                 310                 315                 320

Leu Met His Leu Gly Arg Tyr Ile Pro Phe Leu Pro Ser Glu Lys Leu
                325                 330                 335

Glu Arg Thr Ser Ser Val Ser Pro Ser Thr Ala Glu Pro Glu Leu Ser
                340                 345                 350

Ile Val Phe
        355
```

<210> SEQ ID NO 7
<211> LENGTH: 29
<212> TYPE: DNA
<213> ORGANISM: Artificial

```
<220> FEATURE:
<223> OTHER INFORMATION: Synthesized Primer

<400> SEQUENCE: 7
cggaattcat gacaacctca ctagataca                                29

<210> SEQ ID NO 8
<211> LENGTH: 18
<212> TYPE: DNA
<213> ORGANISM: Artificial
<220> FEATURE:
<223> OTHER INFORMATION: Synthesized Primer

<400> SEQUENCE: 8
ggacaatggc cacctacc                                            18

<210> SEQ ID NO 9
<211> LENGTH: 19
<212> TYPE: DNA
<213> ORGANISM: Artificial
<220> FEATURE:
<223> OTHER INFORMATION: Synthesized Primer

<400> SEQUENCE: 9
gcatgtgtaa gctcctctc                                           19

<210> SEQ ID NO 10
<211> LENGTH: 30
<212> TYPE: DNA
<213> ORGANISM: Artificial
<220> FEATURE:
<223> OTHER INFORMATION: Synthesized Primer

<400> SEQUENCE: 10
gctctagact aaaacacaat agagagttcc                               30

<210> SEQ ID NO 11
<211> LENGTH: 30
<212> TYPE: DNA
<213> ORGANISM: Artificial
<220> FEATURE:
<223> OTHER INFORMATION: Synthesized Primer

<400> SEQUENCE: 11
cggggtacca tgctgtccac atctcgttct                               30

<210> SEQ ID NO 12
<211> LENGTH: 31
<212> TYPE: DNA
<213> ORGANISM: Artificial
<220> FEATURE:
<223> OTHER INFORMATION: Synthesized Primer

<400> SEQUENCE: 12
cggggtacct cctcgtttta taaaaccagc c                             31

<210> SEQ ID NO 13
<211> LENGTH: 30
<212> TYPE: DNA
<213> ORGANISM: Artificial
<220> FEATURE:
<223> OTHER INFORMATION: Synthesized Primer

<400> SEQUENCE: 13
cccaaagctt atgacaacct cactagatac                               30
```

<210> SEQ ID NO 14
<211> LENGTH: 27
<212> TYPE: DNA
<213> ORGANISM: Artificial
<220> FEATURE:
<223> OTHER INFORMATION: Synthesized Primer

<400> SEQUENCE: 14
gcaatatttc cggaacctct ctccaac                               27

<210> SEQ ID NO 15
<211> LENGTH: 28
<212> TYPE: DNA
<213> ORGANISM: Artificial
<220> FEATURE:
<223> OTHER INFORMATION: Synthesized Primer

<400> SEQUENCE: 15
gggatatctc tcggtgttct tccgaaag                              28

<210> SEQ ID NO 16
<211> LENGTH: 23
<212> TYPE: DNA
<213> ORGANISM: Artificial
<220> FEATURE:
<223> OTHER INFORMATION: Synthesized Primer

<400> SEQUENCE: 16
cgggatcctc tagattataa acc                                   23

<210> SEQ ID NO 17
<211> LENGTH: 26
<212> TYPE: DNA
<213> ORGANISM: Artificial
<220> FEATURE:
<223> OTHER INFORMATION: Synthesized Primer

<400> SEQUENCE: 17
cccaagctta tgctgtccac atctcg                                26

<210> SEQ ID NO 18
<211> LENGTH: 28
<212> TYPE: DNA
<213> ORGANISM: Artificial
<220> FEATURE:
<223> OTHER INFORMATION: Synthesized Primer

<400> SEQUENCE: 18
ccgatatctt ctgaacttct ccccaacg                              28

<210> SEQ ID NO 19
<211> LENGTH: 28
<212> TYPE: DNA
<213> ORGANISM: Artificial
<220> FEATURE:
<223> OTHER INFORMATION: Synthesized Primer

<400> SEQUENCE: 19
cgaatatttg cgccacttct tccacagg                              28

<210> SEQ ID NO 20
<211> LENGTH: 23
<212> TYPE: DNA
<213> ORGANISM: Artificial
<220> FEATURE:
<223> OTHER INFORMATION: Synthesized Primer

<400> SEQUENCE: 20
cgggatcctc tagactaaaa cac    23

<210> SEQ ID NO 21
<211> LENGTH: 1071
<212> TYPE: DNA
<213> ORGANISM: Artificial
<220> FEATURE:
<223> OTHER INFORMATION: Constructed 3/2 Chimera
<220> FEATURE:
<221> NAME/KEY: CDS
<222> LOCATION: (1)..(1071)

<400> SEQUENCE: 21

| | | | | | | | | | | | | | | | | |
|---|---|---|---|---|---|---|---|---|---|---|---|---|---|---|---|---|
| atg | aca | acc | tca | cta | gat | aca | gtt | gag | acc | ttt | ggt | acc | aca | tcc | tac | 48 |
| Met | Thr | Thr | Ser | Leu | Asp | Thr | Val | Glu | Thr | Phe | Gly | Thr | Thr | Ser | Tyr | |
| 1 | | | | 5 | | | | | 10 | | | | | 15 | | |
| tat | gat | gac | gtg | ggc | ctg | ctc | tgt | gaa | aaa | gct | gat | acc | aga | gca | ctg | 96 |
| Tyr | Asp | Asp | Val | Gly | Leu | Leu | Cys | Glu | Lys | Ala | Asp | Thr | Arg | Ala | Leu | |
| | | | 20 | | | | | 25 | | | | | 30 | | | |
| atg | gcc | cag | ttt | gtg | ccc | ccg | ctg | tac | tcc | ctg | gtg | ttc | act | gtg | ggc | 144 |
| Met | Ala | Gln | Phe | Val | Pro | Pro | Leu | Tyr | Ser | Leu | Val | Phe | Thr | Val | Gly | |
| | | 35 | | | | | 40 | | | | | 45 | | | | |
| ctc | ttg | ggc | aat | gtg | gtg | gtg | gtg | atg | atc | ctc | ata | aaa | tac | agg | agg | 192 |
| Leu | Leu | Gly | Asn | Val | Val | Val | Val | Met | Ile | Leu | Ile | Lys | Tyr | Arg | Arg | |
| 50 | | | | | 55 | | | | | 60 | | | | | | |
| ctc | cga | att | atg | acc | aac | atc | tac | ctg | ctc | aac | ctg | gcc | att | tcg | gac | 240 |
| Leu | Arg | Ile | Met | Thr | Asn | Ile | Tyr | Leu | Leu | Asn | Leu | Ala | Ile | Ser | Asp | |
| 65 | | | | | 70 | | | | | 75 | | | | | 80 | |
| ctg | ctc | ttc | ctc | gtc | acc | ctt | cca | ttc | tgg | atc | cac | tat | gtc | agg | ggg | 288 |
| Leu | Leu | Phe | Leu | Val | Thr | Leu | Pro | Phe | Trp | Ile | His | Tyr | Val | Arg | Gly | |
| | | | | 85 | | | | | 90 | | | | | 95 | | |
| cat | aac | tgg | gtt | ttt | ggc | cat | ggc | atg | tgt | aag | ctc | ctc | tca | ggg | ttt | 336 |
| His | Asn | Trp | Val | Phe | Gly | His | Gly | Met | Cys | Lys | Leu | Leu | Ser | Gly | Phe | |
| | | | 100 | | | | | 105 | | | | | 110 | | | |
| tat | cac | aca | ggc | ttg | tac | agc | gag | atc | ttt | ttc | ata | atc | ctg | ctg | aca | 384 |
| Tyr | His | Thr | Gly | Leu | Tyr | Ser | Glu | Ile | Phe | Phe | Ile | Ile | Leu | Leu | Thr | |
| | | 115 | | | | | 120 | | | | | 125 | | | | |
| atc | gac | agg | tac | ctg | gcc | att | gtc | cat | gct | gtg | ttt | gcc | ctt | cga | gcc | 432 |
| Ile | Asp | Arg | Tyr | Leu | Ala | Ile | Val | His | Ala | Val | Phe | Ala | Leu | Arg | Ala | |
| 130 | | | | | 135 | | | | | 140 | | | | | | |
| cgg | act | gtc | act | ttt | ggt | gtc | atc | acc | agc | atc | gtc | acc | tgg | ggc | ctg | 480 |
| Arg | Thr | Val | Thr | Phe | Gly | Val | Ile | Thr | Ser | Ile | Val | Thr | Trp | Gly | Leu | |
| 145 | | | | | 150 | | | | | 155 | | | | | 160 | |
| gca | gtg | cta | gca | gct | ctt | cct | gaa | ttt | atc | ttc | tat | gag | act | gaa | gag | 528 |
| Ala | Val | Leu | Ala | Ala | Leu | Pro | Glu | Phe | Ile | Phe | Tyr | Glu | Thr | Glu | Glu | |
| | | | | 165 | | | | | 170 | | | | | 175 | | |
| ttg | ttt | gaa | gag | act | ctt | tgc | agt | gct | ctt | tac | cca | gag | gat | aca | gta | 576 |
| Leu | Phe | Glu | Glu | Thr | Leu | Cys | Ser | Ala | Leu | Tyr | Pro | Glu | Asp | Thr | Val | |
| | | | | 180 | | | | | 185 | | | | | 190 | | |
| tat | agc | tgg | agg | cat | ttc | cac | act | ctg | aga | atg | acc | atc | ttc | tgt | ctc | 624 |
| Tyr | Ser | Trp | Arg | His | Phe | His | Thr | Leu | Arg | Met | Thr | Ile | Phe | Cys | Leu | |
| | | 195 | | | | | 200 | | | | | 205 | | | | |
| gtt | ctc | cct | ctg | ctc | gtt | atg | gcc | atc | tgc | tac | aca | gga | atc | atc | aaa | 672 |
| Val | Leu | Pro | Leu | Leu | Val | Met | Ala | Ile | Cys | Tyr | Thr | Gly | Ile | Ile | Lys | |
| | | 210 | | | | | 215 | | | | | 220 | | | | |
| acg | ctg | ctg | agg | tgc | ccc | agt | aaa | aaa | aag | tac | aag | gcc | atc | cgg | ctc | 720 |
| Thr | Leu | Leu | Arg | Cys | Pro | Ser | Lys | Lys | Lys | Tyr | Lys | Ala | Ile | Arg | Leu | |
| 225 | | | | | 230 | | | | | 235 | | | | | 240 | |
| att | ttt | gtc | atc | atg | gcg | gtg | ttt | ttc | att | ttc | tgg | aca | ccc | tac | aat | 768 |

-continued

```
Ile Phe Val Ile Met Ala Val Phe Phe Ile Phe Trp Thr Pro Tyr Asn
                245                 250                 255
gtg gct atc ctt ctc tct tcc tat caa tcc atc tta ttt gga aat gac      816
Val Ala Ile Leu Leu Ser Ser Tyr Gln Ser Ile Leu Phe Gly Asn Asp
            260                 265                 270
tgt gag cgg agc aag cat ctg gac ctg gtc atg ctg gtg aca gag gtg      864
Cys Glu Arg Ser Lys His Leu Asp Leu Val Met Leu Val Thr Glu Val
        275                 280                 285
atc gcc tac tcc cac tgc tgc atg aac ccg gtg atc tac gcc ttt gtt      912
Ile Ala Tyr Ser His Cys Cys Met Asn Pro Val Ile Tyr Ala Phe Val
    290                 295                 300
gga gag agg ttc cgg aaa tat ctc tcg gtg ttc ttc cga aag cac atc      960
Gly Glu Arg Phe Arg Lys Tyr Leu Ser Val Phe Phe Arg Lys His Ile
305                 310                 315                 320
acc aag cgc ttc tgc aaa caa tgt cca gtt ttc tac agg gag aca gtg     1008
Thr Lys Arg Phe Cys Lys Gln Cys Pro Val Phe Tyr Arg Glu Thr Val
                325                 330                 335
gat gga gtg act tca aca aac acg cct tcc act ggg gag cag gaa gtc     1056
Asp Gly Val Thr Ser Thr Asn Thr Pro Ser Thr Gly Glu Gln Glu Val
            340                 345                 350
tcg gct ggt tta taa                                                  1071
Ser Ala Gly Leu
        355
```

<210> SEQ ID NO 22
<211> LENGTH: 356
<212> TYPE: PRT
<213> ORGANISM: Artificial
<220> FEATURE:
<223> OTHER INFORMATION: Synthetic Construct

<400> SEQUENCE: 22

```
Met Thr Thr Ser Leu Asp Thr Val Glu Thr Phe Gly Thr Thr Ser Tyr
1               5                   10                  15
Tyr Asp Asp Val Gly Leu Leu Cys Glu Lys Ala Asp Thr Arg Ala Leu
            20                  25                  30
Met Ala Gln Phe Val Pro Pro Leu Tyr Ser Leu Val Phe Thr Val Gly
        35                  40                  45
Leu Leu Gly Asn Val Val Val Met Ile Leu Ile Lys Tyr Arg Arg
    50                  55                  60
Leu Arg Ile Met Thr Asn Ile Tyr Leu Leu Asn Leu Ala Ile Ser Asp
65                  70                  75                  80
Leu Leu Phe Leu Val Thr Leu Pro Phe Trp Ile His Tyr Val Arg Gly
                85                  90                  95
His Asn Trp Val Phe Gly His Gly Met Cys Lys Leu Leu Ser Gly Phe
            100                 105                 110
Tyr His Thr Gly Leu Tyr Ser Glu Ile Phe Phe Ile Ile Leu Leu Thr
        115                 120                 125
Ile Asp Arg Tyr Leu Ala Ile Val His Ala Val Phe Ala Leu Arg Ala
    130                 135                 140
Arg Thr Val Thr Phe Gly Val Ile Thr Ser Ile Val Thr Trp Gly Leu
145                 150                 155                 160
Ala Val Leu Ala Ala Leu Pro Glu Phe Ile Phe Tyr Glu Thr Glu Glu
                165                 170                 175
Leu Phe Glu Glu Thr Leu Cys Ser Ala Leu Tyr Pro Glu Asp Thr Val
            180                 185                 190
Tyr Ser Trp Arg His Phe His Thr Leu Arg Met Thr Ile Phe Cys Leu
        195                 200                 205
```

```
Val Leu Pro Leu Leu Val Met Ala Ile Cys Tyr Thr Gly Ile Ile Lys
        210                 215                 220

Thr Leu Arg Cys Pro Ser Lys Lys Tyr Lys Ala Ile Arg Leu
225                 230                 235                 240

Ile Phe Val Ile Met Ala Val Phe Phe Ile Phe Trp Thr Pro Tyr Asn
                    245                 250                 255

Val Ala Ile Leu Leu Ser Ser Tyr Gln Ser Ile Leu Phe Gly Asn Asp
            260                 265                 270

Cys Glu Arg Ser Lys His Leu Asp Leu Val Met Leu Val Thr Glu Val
            275                 280                 285

Ile Ala Tyr Ser His Cys Cys Met Asn Pro Val Ile Tyr Ala Phe Val
        290                 295                 300

Gly Glu Arg Phe Arg Lys Tyr Leu Ser Val Phe Phe Arg Lys His Ile
305                 310                 315                 320

Thr Lys Arg Phe Cys Lys Gln Cys Pro Val Phe Tyr Arg Glu Thr Val
                    325                 330                 335

Asp Gly Val Thr Ser Thr Asn Thr Pro Ser Thr Gly Glu Gln Glu Val
            340                 345                 350

Ser Ala Gly Leu
        355

<210> SEQ ID NO 23
<211> LENGTH: 1080
<212> TYPE: DNA
<213> ORGANISM: Artificial
<220> FEATURE:
<223> OTHER INFORMATION: Constructed 2/3 Chimera
<220> FEATURE:
<221> NAME/KEY: CDS
<222> LOCATION: (1)..(1080)

<400> SEQUENCE: 23 atg ctg tcc aca tct cgt tct cgg ttt atc aga aat acc aac gag agc     48
Met Leu Ser Thr Ser Arg Ser Arg Phe Ile Arg Asn Thr Asn Glu Ser
1               5                   10                  15 ggt gaa gaa gtc acc acc ttt ttt gat tat gat tac ggt gct ccc tgt    96
Gly Glu Glu Val Thr Thr Phe Phe Asp Tyr Asp Tyr Gly Ala Pro Cys
            20                  25                  30 cat aaa ttt gac gtg aag caa att ggg gcc caa ctc ctg cct ccg ctc   144
His Lys Phe Asp Val Lys Gln Ile Gly Ala Gln Leu Leu Pro Pro Leu
        35                  40                  45 tac tcg ctg gtg ttc atc ttt ggt ttt gtg ggc aac atg ctg gtc gtc   192
Tyr Ser Leu Val Phe Ile Phe Gly Phe Val Gly Asn Met Leu Val Val
    50                  55                  60 ctc atc tta ata aac tgc aaa aag ctg aag tgc ttg act gac att tac   240
Leu Ile Leu Ile Asn Cys Lys Lys Leu Lys Cys Leu Thr Asp Ile Tyr
65                  70                  75                  80 ctg ctc aac ctg gcc atc tct gat ctg ctt ttt ctt att act ctc cca   288
Leu Leu Asn Leu Ala Ile Ser Asp Leu Leu Phe Leu Ile Thr Leu Pro
                    85                  90                  95 ttg tgg gct cac tct gct gca aat gag tgg gtc ttt ggg aat gca atg   336
Leu Trp Ala His Ser Ala Ala Asn Glu Trp Val Phe Gly Asn Ala Met
            100                 105                 110 tgc aaa tta ttc aca ggg ctg tat cac atc ggt tat ttt ggc gga atc   384
Cys Lys Leu Phe Thr Gly Leu Tyr His Ile Gly Tyr Phe Gly Gly Ile
        115                 120                 125 ttc ttc atc atc ctc ctg aca atc gat aga tac ctg gct att gtc cat   432
Phe Phe Ile Ile Leu Leu Thr Ile Asp Arg Tyr Leu Ala Ile Val His
    130                 135                 140
```

```
gct gtg ttt gct tta aaa gcc agg acg gtc acc ttt ggg gtg gtg aca       480
Ala Val Phe Ala Leu Lys Ala Arg Thr Val Thr Phe Gly Val Val Thr
145                 150                 155                 160 agt gtg atc acc tgg ttg gtg gct gtg ttt gct tct gtc cca gga atc       528
Ser Val Ile Thr Trp Leu Val Ala Val Phe Ala Ser Val Pro Gly Ile
            165                 170                 175 atc ttt act aaa tgc cag aaa gaa gat tct gtt tat gtc tgt ggc cct       576
Ile Phe Thr Lys Cys Gln Lys Glu Asp Ser Val Tyr Val Cys Gly Pro
        180                 185                 190 tat ttt cca cga gga tgg aat aat ttc cac aca ata atg agg aac att       624
Tyr Phe Pro Arg Gly Trp Asn Asn Phe His Thr Ile Met Arg Asn Ile
    195                 200                 205 ttg ggg ctg gtc ctg ccg ctc ctc atc atg gtc atc tgc tac tcg gga       672
Leu Gly Leu Val Leu Pro Leu Leu Ile Met Val Ile Cys Tyr Ser Gly
210                 215                 220 atc ctg aaa acc ctg ctt cgg tgt cga aac gag aag aag agg cat agg       720
Ile Leu Lys Thr Leu Leu Arg Cys Arg Asn Glu Lys Lys Arg His Arg
225                 230                 235                 240 gca gtg aga gtc atc ttc acc atc atg att gtt tac ttt ctc ttc tgg       768
Ala Val Arg Val Ile Phe Thr Ile Met Ile Val Tyr Phe Leu Phe Trp
            245                 250                 255 act ccc tat aac att gtc att ctc ctg aac acc ttc cag gaa ttc ttc       816
Thr Pro Tyr Asn Ile Val Ile Leu Leu Asn Thr Phe Gln Glu Phe Phe
        260                 265                 270 ggc ctg agt aac tgt gaa agc acc agt caa ctg gac caa gcc acg cag       864
Gly Leu Ser Asn Cys Glu Ser Thr Ser Gln Leu Asp Gln Ala Thr Gln
    275                 280                 285 gtg aca gag act ctt ggg atg act cac tgc tgc atc aat ccc atc atc       912
Val Thr Glu Thr Leu Gly Met Thr His Cys Cys Ile Asn Pro Ile Ile
290                 295                 300 tat gcc ttc gtt ggg gag aag ttc aga agg tat ttg cgc cac ttc ttc       960
Tyr Ala Phe Val Gly Glu Lys Phe Arg Arg Tyr Leu Arg His Phe Phe
305                 310                 315                 320 cac agg cac ttg ctc atg cac ctg ggc aga tac atc cca ttc ctt cct      1008
His Arg His Leu Leu Met His Leu Gly Arg Tyr Ile Pro Phe Leu Pro
            325                 330                 335 agt gag aag ctg gaa aga acc agc tct gtc tct cca tcc aca gca gag      1056
Ser Glu Lys Leu Glu Arg Thr Ser Ser Val Ser Pro Ser Thr Ala Glu
        340                 345                 350 ccg gaa ctc tct att gtg ttt tag                                      1080
Pro Glu Leu Ser Ile Val Phe
            355

<210> SEQ ID NO 24
<211> LENGTH: 359
<212> TYPE: PRT
<213> ORGANISM: Artificial
<220> FEATURE:
<223> OTHER INFORMATION: Synthetic Construct

<400> SEQUENCE: 24

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60
```

-continued

```
Leu Ile Leu Ile Asn Cys Lys Lys Leu Lys Cys Leu Thr Asp Ile Tyr
 65                  70                  75                  80

Leu Leu Asn Leu Ala Ile Ser Asp Leu Leu Phe Leu Ile Thr Leu Pro
                 85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
            195                 200                 205

Leu Gly Leu Val Leu Pro Leu Leu Ile Met Val Ile Cys Tyr Ser Gly
210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
            275                 280                 285

Val Thr Glu Thr Leu Gly Met Thr His Cys Cys Ile Asn Pro Ile Ile
290                 295                 300

Tyr Ala Phe Val Gly Glu Lys Phe Arg Arg Tyr Leu Arg His Phe Phe
305                 310                 315                 320

His Arg His Leu Leu Met His Leu Gly Arg Tyr Ile Pro Phe Leu Pro
                325                 330                 335

Ser Glu Lys Leu Glu Arg Thr Ser Ser Val Ser Pro Ser Thr Ala Glu
            340                 345                 350

Pro Glu Leu Ser Ile Val Phe
            355

<210> SEQ ID NO 25
<211> LENGTH: 9
<212> TYPE: DNA
<213> ORGANISM: Artificial
<220> FEATURE:
<223> OTHER INFORMATION: Synthesized nucleic acid sequence

<400> SEQUENCE: 25 aagcttatg                                                          9
```

POLYNUCLEOTIDES ENCODING CHIMERIC CHEMOKINE RECEPTORS

CROSS-REFERENCE TO RELATED APPLICATIONS

This application claims benefit to U.S. provisional patent application Ser. No. 60/519,605 filed on Nov. 13, 2003. The entire teachings of the referenced application are incorporated herein by reference.

FIELD OF THE INVENTION

The present invention generally relates to chimeric proteins and more particularly to a chimeric chemokine receptor polypeptide comprising a region from a CCR2 chemokine receptor joined to a region from a CCR3 chemokine receptor. The fusion can be ordered with a CCR2 region at the N terminus of the chimeric protein and a CCR3 region joined to the CCR2 region and forming the C terminus of the chimeric. Alternatively, the fusion can be ordered with a CCR3 region at the N terminus of the chimeric protein and a CCR2 region joined to the CCR3 region and forming the C terminus of the chimeric. The chimeric can be employed in a variety of applications, such as ligand binding assays, signalling assays, and assays for compounds that inhibit binding of a chemokine (e.g., eotaxin) to its cognate receptor (e.g., CCR3).

Amino Acid Abbreviations

| Single-Letter Code | Three-Letter Code | Name |
|---|---|---|
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

Functionally Equivalent Codons

| Amino Acid | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Methionine | Met | M | AUG |
| Asparagine | Asn | N | AAC AAU |
| Proline | Pro | P | CCA CCC CCG CCU |
| Glutamine | Gln | Q | CAA CAG |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |
| Leucine | Leu | L | UUA UUG CUA CUC CUG CUU |
| Arginine | Arg | R | AGA AGG CGA CGC CGG CGU |
| Serine | Ser | S | ACG AGU UCA UCC UCG UCU |

BACKGROUND OF THE INVENTION

G-protein-coupled receptors (GPCRs) are the most widely targeted proteins for therapeutic purposes. Structurally, this class of proteins comprises an extracellular N terminal region and an intracellular C terminal region, which are joined by a transmembrane (TM) region comprising seven alpha-helical domains that traverse the cellular membrane bilayer.

The function of each domain (the N terminus and the C terminus) of the GPCRs has been elucidated. Each of the domains of a GPCR has a distinct function. More particularly, GPCRs retain all of their known ligand binding regions within the extracellular regions and TM domains 2 through 7 (e.g., Ling et al., (1999) Proc. Natl. Acad. Sci. U.S.A. 96:7922-7927; Gardella & Juppner, (2001) Trends Endocrin. Metab. 12(5):210-217; Vaidehi et al., (2002) Proc. Natl. Acad. Sci. U.S.A. 99:12622-12627), while the intracellular regions regulate the cell signalling and receptor internalization functions (Trejo et al., (1998) Proc. Natl. Acad. Sci. U.S.A. 95:13698-13702; Heding et al., (1998) J. Biol. Chem. 273(19):11472-11477; Trejo &. Coughlin, (1999) J. Biol. Chem. 274(4):2216-2224; Castro-Fernandez & Conn, (2002) Mol. Cell. Endocrinol. 191:149-156). G-protein coupled receptors, including chemokine receptors, have a wide range of specificities in terms of the signals they receive and those they transduce. As described further herein, these observations have been applied to the present invention in the form of chemokine receptor chimeras that retain ligand binding ability as well as G-protein-mediated signalling activity.

The chemokine receptor family of G-protein coupled receptors represents the largest group of peptide-binding GPCRs described to date (Onuffer & Horuk, (2002) Trends Pharmacol. Sci. 23(10):459-467). In this capacity, the bound peptides are chemokines for the chemokine receptor (the GPCR) (see, e.g., Yoshie et al., (2001) Adv. Immunol. 78:57). Chemokines are about 4 to about 14 kDa in size and comprise four conserved cysteine residues. They are broadly grouped into two groups: a major group comprising the CC and CXC subgroups in which two cysteines are adjacent or separated by one residue, and a minor group comprising the C and CXXXC subgroups in which the second cysteine is absent or is separated from the first cysteine by three residues (see, e.g., Horuk, (2003) Methods 29:369-375; Horuk, (2001) Cytokine Growth Factor Rev. 12:313-335). The classification scheme depends on the number and position of the first two conserved cysteine residues (Horuk, (2003) Methods 29:369-375).

At least 18 chemokine receptors have been identified, including 10 CC-type chemokine receptors (CCR1 (Neote et al., (1993) *Cell* 72:415-425; Gao et al., (1993) *J. Exp. Med.* 177:1421-1427), CCR2 (Charo et al., (1994) *Proc. Natl. Acad. Sci. U.S.A.* 91:2752-56), CCR3 (Combadiere et al., (1995) *J. Biol. Chem.* 270:16491-16494; Combadiere et al., (1995) *J. Biol. Chem.* 270:30235; Daugherty et al., (1996) *J. Exp. Med.* 183:2349-2354; Ponath et al., (1996) *J. Clin. Invest.* 97:604-612), CCR4 (Power et al., (1995) *J. Biol. Chem.* 270:19495-19500), CCR5 (Samson et al., (1996) *Biochem.* 35:3362-3367; Combadiere et al., (1996) *J. Leukocyte Biol.* 60:147-152), CCR6 (Baba et al., (1997) *J. Biol. Chem.* 272:14893-14898), CCR7 (Yoshida et al., (1997) *J. Biol. Chem.* 272:13803-13809), CCR8 (Tiffany et al., (1997) *J. Exp. Med.* 186:165-170; Roos et al., (1997) *J. Biol. Chem.* 272:17251-17254; Horuk et al., (1998) *J. Biol. Chem.* 273: 386-391; Goya et al., (1998) *J. Immunol.* 160:1975-1981), CCR9 (Zaballos et al., (1999) *J. Immunol.* 162:5671-5675), CCR10 (Homey et al., (2000) *J. Immunol.* 164:3465-3470; Jarmin et al., (2000) *J. Immunol.* 164:3460-3464)) and 8 of the CXC, CXXXC and XC types (CXCR1 (Holmes et al., (1991) *Science* 253:1278-1280), CXCR2 (Murphy & Tiffany, (1991) *Science* 253:1280-1283), CXCR3 (Marchese et al., (1995) *Genomics* 29:335-344; Loetscher et al., (1996) *J. Exp. Med.* 184:963-969), CXCR4 (Nomura et al., (1993) *Int. Immunol.* 5:1239-1249; Federspiel et al., (1993) *Genomics* 16:707-712; Jazin et al., (1993) *Regul. Pep.* 47:247-258; Herzog et al., (1993) *DNA Cell Biol.* 12:465-471; Loetscher et al., (1993) *J. Biol. Chem.* 269:232-237), CXCR5 (Legler et al., (1998) *J. Exp. Med.* 187:655-660), CXCR6 (Matloubian et al., (2000) *Nature Immunol.* 1:298-304), CXXXCR1 (Combadiere et al., (1998) *J. Biol. Chem.* 273:23799-23804) and XCR1 (Yoshida et al., (1998) J. Biol. Chem. 273:16551-16554)). See, e.g., Horuk, (2001) *Cytokine Growth Factor Rev.* 12:313-335 for a review of chemokine receptors.

The nucleic acid sequences encoding the known chemokine receptors (which can be employed in the present invention and are incorporated herein by reference) are publicly available from the GenBank database and have the following accession numbers:

| Table of GenBank Accessions | |
|---|---|
| CCR1 | L10918, L09230, D10925 |
| CCR2 | U03905, U80924, D29984, U03882, U80924 |
| CCR3 | U28694, U51241, U49727 |
| CCR4 | X85740 |
| CCR5 | U54994, X91492, U57840 |
| CCR6 | U60000, U45984, U68032, Z79782 |
| CCR7 | X84702, L31581, L31584, L08176 |
| CCR8 | U45983, Z79782, U62556, Y08456 |
| CCR9 | U45982 |
| CCR10 | U13667 |
| CXCR1 | L19591, U11870, X65858, L19592, M68932 |
| CXCR2 | L19593, M94582, U11869, M73969, M99412 |
| CXCR3 | X95876, U32674 |
| CXCR4 | X71635, D10924, M99293, L01639, L06797 |
| CXCR5 | X68149, X68829 |
| CXCR6 | U73531 |
| CX3CR1 | U20350, U28934 |
| XCR1 | L36149 |

A function of the chemokine receptor/chemokine combination is to attract and activate cells involved in a variety of immune responses (see, e.g., Yoshie et al., (2001) *Adv. Immunol.* 78:57; Rollins, (1997) Blood 90:909; Baggiolini, (1998) *Nature* 392:565; Nagasawa et al., (1996) *Nature* 382:635). Depending on the cellular distribution and patterns of expression/production of these pairs of proteins, the coordination of extremely complex biological, notably immunological, phenomena can be accomplished (Horuk, (2001) *Cytokine Growth Factor Rev.* 12:313-335; Baggiolini, (1998) *Nature* 392:565-68). Because multiple chemokine receptors are often expressed in a single cell type, and because many chemokine receptors are capable of binding multiple chemokines, the complexity of possible interactions is enormous.

The only known receptor for the chemokine eotaxin is CCR3; however, CCR3, (the eotaxin receptor) is also capable of binding other chemokines including eotaxin-2, RANTES, MCP-2, MCP-3 and MCP-4 (see, e.g., Horuk, (2001) *Cytokine Growth Factor Rev.* 12:313-335; Baggiolini, (1998) *Nature* 392:565-68). In the case of CCR3 and its peptide ligand, eotaxin, the distribution and expression patterns of these two proteins suggest a role in an inflammatory process related to asthma (Baggiolini et al., (1997) *Annu. Rev. Immunol.* 15:675-705) and to contact dermatitis (Taha et al., (2000) *J. Allergy Clin. Immunol.* 105:1002-1007; Yawalkar et al., (1999) *J. Invest. Dermatol.* 113:43-48; Ying et al., (1999) *J. Immunol.* 163:3976-3984). In one example of such a process, following functional binding, CCR3 ligands stimulate calcium flux, actin reorganization, integrin upregulation, receptor internalization, activation of signal transduction pathways and cell migration (Adachi et al., (2001) *J. Immunol.* 167:4609-4615; El-Shazly et al., (1999) *Biochem. Biophys. Res. Comm.* 264(1):163-170; Elsner et al., (1996) *Eur. J. Immunol.* 26:1919-1925; Elsner et al., (1998) *Eur. J. Immunol.* 28:2152-2158; Kampen et al., (2000) *Blood* 95:1911-1917; Lundahl et al., (1998) *Inflammation* 22:123-135; Tachimoto et al., (2002) *Am. J. Respir. Cell Mol. Biol.* 26: 645-649; Tenscher et al., (1996) *Blood* 88: 3195-3199; Woo et al., (2000) *Biochem. Biophys. Res. Comm.* 298: 392-397; Zimmerman et al., (1999) *J. Biol. Chem.* 274: 12611-12618). The eotaxin receptor is known to be restricted in expression primarily to eosinophils, T-helper cells of the $T_H2$ variety (Sallusto et al., (1997) *Science* 277:2005-2007), basophils (Uguccioni et al., (1997) *J. Clin. Invest.* 100:1137-43), mast cells, platelets, dendritic cells and based upon worked described herein, also monocytes. For the most part these cell types are known to be associated with a variety of acute and chronic allergic reactions including resistance to certain parasitic infections.

Continuing, it is known that anti-CCR3 antibody administered to mice by both intraperitoneal, and intra-nasal routes abrogates the eosinophil recruitment into the lung following intra-nasal allergen challenge (Justice et al., (2003) *Am. J. Physiol. Lung Cell Mol. Physiol.* 284:L169-L178). The antibody also eliminates airway hyper-responsiveness to methacholine challenge. CCR3 knockout mice exhibit markedly reduced eosinophil recruitment to the lung and skin following allergen challenge (Humbles et al., (2002) *Proc. Natl. Acad. Sci. U.S.A.* 99(3): 1479-84; Ma et al., (2002) *J. Clin. Invest.* 109(5):621-28). The effect on airway hyper-responsiveness, however, depends on the route of antigen sensitization. Mice sensitized by intraperitoneal injection show a slightly enhanced hyper-responsiveness (Humbles et al., (2002) *Proc. Natl. Acad. Sci. U.S.A.* 99(3): 1479-84), whereas those sensitized by epi-cutaneous application of antigen show a near-complete reduction of hyper-responsiveness.

CCR2 exists in two isoforms, CCR2A and CCR2B (Charo et al., (1994) *Proc. Natl. Acad. Sci. U.S.A.* 91:2752-56). In contrast to CCR3, which is primarily expressed in eosinophils, CCR2 (also referred to as MCP-1R) is predominantly expressed in the monocyte/macrophage lineage and its primary peptide ligand, MCP-1, is thought to act to recruit monocytes to sites of inflammation (Taub et al., (1993) *Science* 260:355; Roth et al., (1995) *Eur. J. Immunol.* 25:3482). In addition to MCP-1(α nd β), chemokine ligands known to interact with CCR2 include MCP-2, MCP-3, MCP-4 and MCP-5. Expression of CCR2 has also been described on basophils, NK cells, memory T cells, eosinophils and dendritic cells. Following functional binding, CCR2 ligands stimulate calcium flux, actin reorganization, integrin upregulation, receptor internalization, activation of signal transduction pathways and cell migration. Based upon the cellular distribution and activity of CCR2 and its ligands, therapeutic potential of CCR2 inhibitors may exist for chronic inflammatory conditions, such as atherosclerosis, rheumatoid arthritis and multiple sclerosis.

In the case of CCR2A (GenBank Accession No. AF545480), it is predicted that residues 1-42 of SEQ ID NO:2 comprise the N terminal region, that residues 310-374 of SEQ ID NO:2 comprise the C terminal region and that residues 43-309 of SEQ ID NO:2 comprise the TM region. In the case of CCR2B (GenBank Accession No. U03905), it is predicted that residues 1-42 of SEQ ID NO:4 comprise the N terminal region, that residues 310-360 of SEQ ID NO:4 comprise the C terminal region and that residues 43-309 of SEQ ID NO:4 comprise the TM region. With respect to CCR3 (GenBank Accession No. U28694), it is predicted that residues 1-34 of SEQ ID NO:6 comprise the N terminal region, that residues 306-355 of SEQ ID NO:6 comprise the C terminal region and that residues 35-305 of SEQ ID NO:6 comprise the TM region. The TM region creates extensive intracellular and extracellular loops of protein that confer specific biological reactivity and function. GPCRs are capable of responding to a wide variety of stimuli including light, odorants, ions, lipids, peptides and globular proteins.

The present invention relates to chimeric chemokine receptors. Several particular chimeric chemokine receptors have previously been generated. For example, Peiper et al. report the generation of (1) a chimera comprising the N terminal region of DARC, which was joined with the remaining portion of CCR1; and (2) a chimera comprising the N terminal region of CCR1, which was joined with the remaining portion of DARC (Peiper et al., (1997) *Method Enzymol.* 288:57-71). The chimeras of Peiper et al., however, only incorporated the extracellular N terminal region of CCR1 and DARC. Further, Alkhatib et al. (Alkhatib et al., (1997) *J. Biol. Chem.* 33:20420-26) and Pease et al. (Pease et al., (1998) *J. Biol. Chem.* 273(32):19972-76) prepared various CCR1/CCR3 chimeras. The chimeras of Alkhatib and Pease, however, also include only the extracellular N terminus of a CCR1 or CCR3 receptor joined with the remainder of a CCR3 or CCR1 receptor, respectively. Hill et al. prepared chimeras comprising the N terminal domain of CCR1, CCR2 and CXCR4 and the remaining portion of CCR5, but again, these chimeras did not incorporate a contiguous N terminus/seven TM helix element (Hill et al., (1998) *Virol.* 248:357-71). Similarly, Rucker et al. prepared CCR2B/CCR5 chimeras (Rucker et al., (1996) *Cell* 87:437-46), but these chimeras did not incorporate an intact N terminus/seven TM helix element from a single receptor. Chimeras comprising non-chemokine receptor components have also been prepared (CCR2/CD8; Monteclaro & Charo, (1997) *J. Biol. Chem.* 272(37):23186-90) as well as chimeras formed between orthologs of the same protein (human/macaque CCR3; Sol et al., (1998) *Virol.* 240:213-20), but neither of these chimeras incorporated an intact N terminus/seven TM helix element from a single receptor.

Although at least the above described chimeric receptors have been generated, these chimeras do not comprise a contiguous N terminus/seven TM helix element in general, nor do they comprise a region of a CCR3 receptor joined with a region of a CCR2 receptor in particular. Therefore these chimeras do not fully exhibit the properties of both of the CCRs that were used to construct the chimera (i.e., the properties of the N terminal and TM region of a first CCR, such as CCR3 and the intracellular C terminus of a second CCR, such as CCR2). Notably, these previously-generated chimeras do not include the TM region of the N terminal component of the chimera.

An impetus for generating the chimeric receptors of the present invention was the need for a receptor capable of high-affinity binding to the cognate ligand while retaining at least some of the downstream signalling capabilities associated with the native receptor. Such a chimera could be employed in a screening assay to identify chemokines that bind to a chemokine receptor and/or induce signalling. Prior to the present invention, such a chimeric receptor was lacking in the art.

Thus, what is needed is a chimeric chemokine receptor comprising the N-terminus through at least the last residue of the seventh transmembrane region of a first CCR (e.g., CCR3 or CCR2) joined to all or a portion of the C-terminus of a second CCR (e.g., CCR2 or CCR3, respectively). Such a receptor would facilitate a number of different assays, such as more accurate chemokine ligand binding, and signalling assays than can be achieved by employing the chimeras known in the art. Further, by modifying just the cytoplasmic tail of a chemokine receptor it may also be possible to generate alternative signalling pathways upon binding of the cognate ligand. These alternative pathways might prove to be easier to describe and/or quantify than those pathways associated with the wild-type receptor. The chimeric chemokine receptor would also be useful in modulator design efforts. The present invention solves these and other problems.

SUMMARY OF THE INVENTION

The present invention relates to an isolated chimeric chemokine receptor. In one embodiment the chimeric chemokine receptor comprises: (a) a first polypeptide segment comprising a contiguous amino acid sequence extending from the first residue of the N terminus of a first chemokine receptor to at least the last residue of the seventh transmembrane helix of the first chemokine receptor; and (b) a second polypeptide segment joined to the first polypeptide sequence, the second polypeptide sequence comprising a contiguous amino acid sequence comprising all or a portion of the C terminus of a second chemokine receptor.

In another embodiment, the first chemokine receptor is selected from the group consisting of a receptor that binds a chemokine of the form C, a chemokine of the form CC, a chemokine of the form CX, and a chemokine of the form CXXXC. In another embodiment, the first chemokine receptor is selected from the group consisting CCR1, CCR2, CCR3, CCR4, CCR5, CCR6, CCR7, CCR8, CCR9, CCR10, CXCR1, CXCR2, CXCR3, CXCR4, CXCR5, CXCR6, CXXXCR1 and XCR1. In a further embodiment, the second chemokine receptor is selected from the group consisting of a receptor that binds a chemokine of the form C, a chemokine of the form CC, a chemokine of the form CX, and a chemokine of the form CXXXC. In yet another embodiment, the second chemokine receptor is selected from the group consisting CCR1, CCR2, CCR3, CCR4, CCR5, CCR6, CCR7, CCR8, CCR9, CCR10, CXCR1, CXCR2, CXCR3, CXCR4, CXCR5, CXCR6, CXXXCR1 and XCR1. In yet another embodiment, the first chemokine receptor is CCR3 and the second chemokine receptor is CCR2, and in a still further embodiment, the CCR2 is CCR2 isoform A. In various embodiments, the CCR2 is CCR2 isoform B, the first chemokine receptor is CCR2 and the second chemokine receptor is CCR3, the CCR2 is CCR2 isoform A and/or the CCR2 is CCR2 isoform B. In still additional embodiments, the first polypeptide sequence comprises residues 1-310 of SEQ ID NO:6 and the second polypeptide sequence comprises residues 316-360 of SEQ ID NO:4. In a further embodiment, the first polypeptide sequence comprises residues 1-314 of SEQ ID NO:4 and the second polypeptide sequence comprises residues 312-355 of SEQ ID NO:6. In other aspects, the present invention relates to an isolated polynucleotide encoding the chimeric chemokine receptor of claim 1, a host cell comprising the polynucleotide, an isolated polynucleotide that is complementary to the polynucleotide, and a DNA vector comprising the polynucleotide of claim 14.

The present invention also relates to a method for producing a chimeric chemokine receptor. In one embodiment the method comprises: (a) growing a host cell in a suitable nutrient medium to produce the chimeric chemokine receptor; and (b) isolating the chimeric chemokine receptor from the cell or medium. In another embodiment, the chimeric chemokine receptor comprises the amino acid sequence set forth in SEQ ID NO:22. In some embodiments of the method, an isolated polynucleotide encoding the chimeric chemokine receptor is disclosed. In an embodiment, the polynucleotide sequence is that set forth in SEQ ID NO:21. A host cell comprising the polynucleotide, an isolated polynucleotide that is complementary to the polynucleotide, and a DNA vector comprising the polynucleotide constitute additional embodiments of the method.

Also disclosed is a method for producing a chimeric chemokine receptor. In one embodiment the method comprises (a) growing a host cell in a suitable nutrient medium to produce a chimeric chemokine receptor; and (b) isolating the chimeric chemokine receptor from the cell or medium. In some embodiments of the method the polypeptide comprises the amino acid sequence set forth in SEQ ID NO:24. Also disclosed is an isolated polynucleotide encoding the chimeric chemokine receptor. In an embodiment, the polynucleotide sequence is that set forth in SEQ ID NO:23. In other embodiments, the invention relates to a host cell comprising the polynucleotide and an isolated polynucleotide that is complementary to the polynucleotide. A DNA vector comprising the polynucleotide is also disclosed.

In another aspect, the present invention relates to a method of identifying a compound that binds to a chemokine receptor. In one embodiment, the method comprises: (a) contacting a test compound with a chimeric chemokine receptor poylpeptide comprising: a first polypeptide segment comprising a contiguous amino acid sequence extending from the first residue of the N terminus of a first chemokine receptor to at least the last residue of the seventh transmembrane helix of the first chemokine receptor; and (i) a first polypeptide segment comprising a contiguous amino acid sequence extending from the first residue of the N terminus of a first chemokine receptor to at least the last residue of the seventh transmembrane helix of the first chemokine receptor; and (ii) a second polypeptide segment joined to the first polypeptide sequence, the second polypeptide sequence comprising a contiguous amino acid sequence comprising all or a portion of the C terminus of a second chemokine receptor; and (b) determining if the test compound bound to the chimeric chemokine receptor. In one embodiment of the method, the test compound is labeled. In another embodiment, the label is selected from the group consisting of a radiolabel and an enzyme. In yet a further embodiment, the method is carried out in the presence of a ligand that is known to bind to the chimeric chemokine receptor.

The present invention also relates to a method of identifying a degree to which a compound induces intracellular signalling. In one embodiment the method comprises: (a) determining a reference level of intracellular signalling in the absence of a test compound; (b) contacting the test compound with a chimeric chemokine receptor poylpeptide comprising: (i) a first polypeptide segment comprising a contiguous amino acid sequence extending from the first residue of the N terminus of a first chemokine receptor to at least the last residue of the seventh transmembrane helix of the first chemokine receptor; and (ii) a second polypeptide segment joined to the first polypeptide sequence, the second polypeptide sequence comprising a contiguous amino acid sequence comprising all or a portion of the C terminus of a second chemokine receptor; (c) determining a level to which the test compound induces intracellular signalling; and (d) comparing the reference level of intracellular signalling with the level of intracellular signalling in the presence of the test compound, whereby a degree to which a compound induces intracellular signalling is identified. In a further embodiment, the signalling activity is a transient increase in the concentration of cytosolic free calcium. In another embodiment, the signalling activity is GTP hydrolysis.

Accordingly, it is an object of the present invention to provide a chimera comprising (a) a first polypeptide segment comprising a contiguous amino acid sequence extending from the first residue of the N terminus of a first chemokine receptor to at least the last residue of the seventh transmembrane helix of the first chemokine receptor; and (b) a second polypeptide segment joined to the first polypeptide sequence, the second polypeptide sequence comprising a contiguous amino acid sequence comprising all or a portion of the C terminus of a second chemokine receptor. This object is achieved in whole or in part by the present invention.

An object of the invention having been stated hereinabove, other objects will be evident as the description proceeds, when taken in connection with the accompanying Drawings and Examples as described hereinbelow.

BRIEF DESCRIPTION OF THE DRAWINGS

FIG. 2B is nucleotide sequence highlighting the open reading frame of human CCR3, beginning at the FLAG PreProTrypsin signal sequence.

FIG. 3B is an alignment of the amino acid sequences of human CCR2B (SEQ ID NO:4), CCR3 (SEQ ID NO:6) and the CCR3/2 chimera (SEQ ID NO:22).

FIG. 8A is an alignment of a nucleic acid encoding a CCR2/3 chimera (SEQ ID NO:23) with a nucleic acid encoding human CCR2B (SEQ ID NO:3).

FIG. 8B is an alignment of the amino acid sequence of a CCR2/3 chimera (SEQ ID NO:24) with the amino acid sequence of a human CCR2B (SEQ ID NO:4).

DETAILED DESCRIPTION OF THE INVENTION

Figure 1:
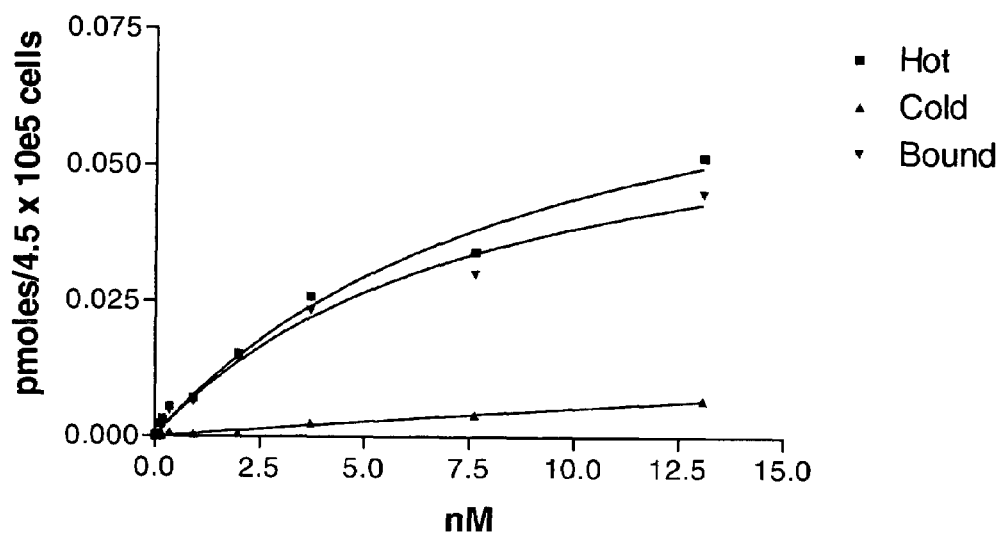
FIG. 1 is a plot depicting the results of a human eotaxin binding analysis of CCR3/2 expressing clone 5.5 cells.

In one aspect, the present invention relates to an isolated chimeric chemokine receptor. In an embodiment the chimeric chemokine receptor comprises: (a) a first polypeptide segment comprising a contiguous amino acid sequence extending from the first residue of the N terminus of a first chemokine receptor to at least the last residue of the seventh transmembrane helix of the first chemokine receptor; and (b) a second polypeptide segment joined to the first polypeptide sequence, the second polypeptide sequence comprising a contiguous amino acid sequence comprising all or a portion of the C terminus of a second chemokine receptor. In a further embodiment, the first polypeptide sequence is derived from a CCR2 polypeptide (e.g., CCR2A or CCR2B) and the second sequence is derived from a CCR3 polypeptide. In another embodiment, the first polypeptide sequence is derived from a CCR3 polypeptide and the second sequence is derived from a CCR2 polypeptide (e.g., CCR2A or CCR2B). An impetus for generating such a chimeric receptor was the need for a receptor capable of binding with high-affinity to its cognate ligand while retaining at least some of the downstream signalling capabilities associated with the full-length receptor. Such a chimera could be employed in a screening assay to identify chemokines that bind to a chemokine receptor and/or induce signalling. Prior to the present invention, such a chimeric receptor was lacking in the art.

I. Definitions

All scientific and technical terms used in this application have meanings commonly used in the art unless otherwise specified. As used in the present disclosure, the following words or phrases have the meanings specified.

Following long-standing patent law convention, the terms "a" and "an" mean "one or more" when used in this application, including the claims.

As used herein, the term "about," when referring to a value or to an amount of mass, weight, time, volume, concentration or percentage is meant to encompass variations of ±20% or less (e.g., ±15%, ±10%, ±7%, ±5%, ±4%, ±3%, ±2%, ±1%, or ±0.1%) from the specified amount, as such variations are appropriate.

As used herein, the terms "amino acid," "amino acid residue" and "residue" are used interchangeably and mean any of the twenty naturally occurring amino acids. An amino acid is formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino (N) terminus of a polypeptide. COOH refers to the free carboxy group present at the carboxy terminus of a polypeptide. In keeping with standard polypeptide nomenclature, abbreviations for amino acid residues are shown in tabular form presented herein above.

It is noted that the amino acid residue sequences represented herein by formulae have a left-to-right orientation, in the conventional direction of amino (N) terminus to carboxy (C) terminus. In addition, the phrases "amino acid" and "amino acid residue" are broadly defined to include modified and unusual amino acids.

Furthermore, it is noted that a dash at the beginning or end of an amino acid residue sequence indicates a peptide bond to a further sequence of one or more amino acid residues, a covalent bond to an amino-terminal group, such as $NH_2$, to an acetyl group or to a carboxy-terminal group, such as COOH.

As used herein, the term "antibody" means polyclonal, monoclonal, antibody fragments and antibody derivatives. The term encompasses antibodies prepared by recombinant techniques, such as chimeric or humanized antibodies, as well as single chain or bispecific antibodies.

As used herein, the terms "antigen" and "epitope," which are well understood in the art, mean all or a portion of a macromolecule that is specifically recognized by a component of the immune system, e.g., an antibody or a T-cell antigen receptor. An epitope is a region of an antigen. As used herein, the term "antigen" encompasses antigenic epitopes, e.g., fragments of an antigen that are antigenic epitopes.

As used herein, the terms "associate" and "bind," and grammatical derivations thereof, are used interchangeably and mean a condition of proximity between or amongst molecules, structural elements, chemical compounds or chemical entities. An association can be non-covalent (i.e., reversible), wherein the juxtaposition is energetically favored by hydrogen bonding or van der Waals or electrostatic interactions, or it can be covalent (i.e., irreversible). Thus in the present disclosure, when it is stated that a ligand "associates" with or "binds" to a protein, it is meant that the ligand interacts with the protein via covalent or non-covalent interactions. In one embodiment the ligand can be an antigen or epitope and the protein can be an antibody.

In a related aspect, the term "associates specifically," and grammatical derivations thereof, means an interaction between a first moiety (e.g., a modulator, such as a chemokine, or an antibody) and a second moiety (e.g., a CCR3/CCR2 chimera) that occurs preferentially to an interaction between the first or second moiety and any other moieties present. By way of example, an antibody is presented with a variety of different antigens, but only binds to a particular antigen. In this example, the antibody "specifically associates" with the particular antigen.

As used herein, the terms "CCR2 gene" and "recombinant CCR2 gene" mean a nucleic acid molecule comprising an open reading frame encoding a CCR2 polypeptide of the present invention, including exon and, optionally, intron sequences. The term encompasses all known or discovered forms of a CCR2 gene, including those encoding isoforms such as, but not limited to, CCR2A and CCR2B.

As used herein, the terms "CCR3 gene" and "recombinant CCR3 gene" mean a nucleic acid molecule comprising an open reading frame encoding a CCR3 polypeptide of the present invention, including both exon and, optionally, intron sequences. The term encompasses all known or discovered forms of a CCR3 gene, including those encoding isoforms.

As used herein, the terms "CCR2 gene product", "CCR2 protein", "CCR2 polypeptide", "CCR2 polypeptide gene product," "CCR2 peptide," "CCR3 gene product", "CCR3 protein", "CCR3 polypeptide", "CCR3 polypeptide gene product" and "CCR3 peptide" are used interchangeably and mean polypeptides and fragments thereof having amino acid sequences that are substantially identical (as defined herein) to the corresponding wild-type amino acid sequence derived from an organism of interest (e.g., a human) and that are biologically active in that they comprise all or a part of the amino acid sequence of a wild-type CCR2 or CCR3 polypeptide (e.g., SEQ ID NOs:2, 4 and/or 6), cross-react with antibodies raised against a CCR2 or CCR3 polypeptide bind a chemokine and/or mediate intracellular signalling. Such biological activity can also include immunogenicity.

In embodiments of the present invention, a wild-type CCR2 or CCR3 polypeptide is encoded by a nucleic sequence of denoted by a GenBank Accession Number presented in the Table of GenBank Accessions provided herein above. Thus, the term "wild-type" can refer to one isoform of a given polypeptide As used herein, the term "chemokine receptor" means a polypeptide that is able to bind a chemokine and/or mediate intracellular signalling. A non-limiting list of representative chemokine receptors includes CCR1, CCR2, CCR3, CCR4, CCR5, CCR6, CCR7, CCR8, CCR9, CXCR1, CXCR2, CXCR3, CXCR4, CXCR5, CXCR6, CXXXCR1 and XCR1.

As used herein, the terms "chimeric protein" and "fusion protein" are used interchangeably and mean a fusion comprising a first molecule (e.g., a region or domain of a CCR2 polypeptide or a CCR3 polypeptide) and an amino acid sequence of second polypeptide molecule (e.g., a region or domain of a CCR2 or CCR3 polypeptide). In one embodiment, a chimeric protein of the present invention comprises a region of a CCR2 polypeptide joined to a region of a CCR3 polypeptide. A chimeric or fusion protein can be expressed from a single chimeric gene encoding the chimeric protein.

As used herein the term "complementary" means a nucleic acid sequence that is base paired, or is capable of base-pairing, according to the standard Watson-Crick complementarity rules. These rules generally hold that guanine pairs with cytosine (G:C) and adenine pairs with either thymine (A:T) in the case of DNA, or adenine pairs with uracil (A:U) in the case of RNA.

As used herein, the term "detecting" means confirming the presence of a target entity by observing the occurrence of a detectable signal, such as a radiologic, fluorescent, colorimetric, etc. signal that will appear exclusively in the presence of the target entity.

As used herein, the terms "isolated" and "purified" are used interchangeably and refer to material (e.g., a nucleic acid or a polypeptide) removed from its original environment (e.g., the natural environment, if the material is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide and/or protein sequences of the present invention; such sequences are specifically excluded from the scope of the present invention.

As used herein, the term "ligand" means any molecule that is known or suspected to associate with another molecule. The term "ligand" encompasses inhibitors, activators, agonists, antagonists, natural substrates and analogs of natural substrates. A ligand can comprise, for example, a nucleic acid sequence, an amino acid sequence (e.g. a peptide and/or polypeptide) or a small molecule.

As used herein the term "modulate," and grammatical derivations thereof, refer to an increase, decrease, or other alteration of any and/or all chemical and/or biological activities or properties mediated by a given DNA sequence, RNA sequence, polypeptide, peptide or molecule. The definition of "modulator" as used herein encompasses agonists, antagonists or inverse agonists of a particular activity or protein. The term "modulate" therefore refers to both upregulation (i.e., activation or stimulation) and downregulation (i.e. inhibition or suppression) of a response by any mode of action. In one embodiment, a modulator modulates chemokine receptor (e.g., GPCR)-mediated signalling activity.

As used herein, the terms "organism", "subject" and "patient" are used interchangeably and mean any organism referenced herein, including prokaryotes, though the terms preferably refer to eukaryotic organisms, notably mammals (e.g., mice, rats, dogs and pigs), and most preferably to humans. The methods of the present invention are particularly preferable for use in the context of warm-blooded vertebrates.

As used herein, the terms "polypeptide segment" "polypeptide portion" and "polypeptide region" are used interchangeably and mean an amino acid sequence that is at least one amino acid shorter than a reference sequence, but retains the sequential order of amino acids in the reference sequence. For example, a polypeptide segment of a CCR2A polypeptide means an amino acid sequence comprising at most 373 amino acids in length (one residue less than the 374 residues shown in SEQ ID NO:2). In another example, a polypeptide segment of a CCR2B polypeptide means an amino acid sequence comprising at most 359 amino acids in length (one residue less than the 360 residues shown in SEQ ID NO:4). In a further example, a polypeptide fragment of a CCR3 polypeptide comprises at most 354 amino acids in length (one residue less than the 355 residues shown in SEQ ID NO:6).

As used herein, the terms "segment" "portion" and "region" are used interchangeably and mean shorter sequences derived from a larger polypeptide or polynucleotide. In some embodiments, a shorter or longer sequence derived from a CCR2 or CCR3 polypeptide retains a biological activity of a full length CCR2 or CCR3 polypeptide, for example (a) the ability to mediate signalling, and/or (b) the ability to bind a chemokine. In other embodiments, a segment can be specifically recognized by an antibody.

As used herein, the terms "protein", "polypeptide" and "peptide" are used interchangeably and mean any polymer comprising any of the 20 protein amino acids, regardless of its size. Although "protein" is often used in reference to relatively large polypeptides, and "peptide" is often used in reference to small polypeptides, usage of these terms in the art overlaps and varies. Therefore, term "polypeptide" as used herein refers to peptides, polypeptides and proteins, unless otherwise noted. Further, the terms "protein", "polypeptide" and "peptide" are used interchangeably herein.

A polypeptide of the present invention can comprise amino acids joined to each other by peptide bonds or modified peptide bonds, i.e., peptide isosteres, and can contain amino acids other than the 20 gene-encoded amino acids. A polypeptide can be modified by either natural processes, such as by post-translational processing, or by chemical modification techniques which are known in the art. Such modifications will be known to those of ordinary skill in the art. Modifications can occur anywhere in a polypeptide, including the peptide backbone, the amino acid side-chains and the amino or carboxyl termini. The same type of modification can be present in the same or varying degrees at several sites in a given polypeptide.

A given polypeptide can contain many types of modifications. A polypeptide can be branched, for example, as a result of ubiquitination, or a polypeptide can be cyclic, with or without branching. Cyclic, branched, and branched cyclic polypeptides can result from posttranslation natural processes or can be made by synthetic methods. Representative modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, e.g., Creighton, *Proteins—Structure And Molecular Properties*, 2$^{nd}$ ed., W. H. Freeman and Company, New York, N.Y., USA (1993); *Posttranslational Covalent Modification Of Proteins*, (Johnson, ed.), Academic Press, New York, N.Y., USA, pp. 1-12 (1983); Seifter et al., (1990) *Method Enzymol.* 182:626-646; and Rattan et al., (1992) *Ann. N.Y. Acad. Sci.* 663:48-62, incorporated herein by reference).

As used herein, the terms "signalling" and "intracellular signalling" are used interchangeably. In one aspect the terms mean the transmission of information regarding the binding of a ligand with the extracellular region of a receptor of the present invention, including both chimeric receptors and full length wild-type receptors, to the interior of a cell. In another aspect, the terms mean one or more events that occur within a cell that indicate a given event has occurred, such as ligand binding by the extracellular segment of a receptor. The one or more events can form elements of a cascade-type pathway.

As used herein, the term "substantially identical" means at least about 70% sequence identity between two amino acid or nucleotide sequences. Polypeptides that are substantially identical to a chemokine receptor polypeptide (or a fragment thereof), such as a CCR2A (SEQ ID NO:2), CCR2B (SEQ ID NO:4) or a CCR3 polypeptide (SEQ ID NO:6), can have between about 70% and about 80%, preferably between about 81% to about 90% or even more preferably between about 91% and about 99% sequence identity with the corresponding sequence of a wild-type CCR2 or CCR3 protein, or fragment thereof. Sequence identity is calculated based on a reference sequence, which can be a subset of a larger sequence. When a reference sequence is a polypeptide sequence, the reference sequence can be at least about 6 amino acids long or more usually at least about 10 amino acids long, and can extend to the complete sequence that is being compared. When a reference is a nucleotide sequence, the reference sequence can also be at least about 18 residues in length or at least about 30 residues in length. Algorithms for sequence analysis are known in the art, such as BLAST, described in Altschul et al., (1990) *J. Mol. Biol.* 215: 403-10, and others described herein.

As used herein, the term "vector" means a replicon, such as plasmid, phage or cosmid, with which another DNA segment may be associated so as to bring about the replication of the associated segment.

II. Chimeric Chemokine Receptors of the Present Invention

Throughout the present disclosure, the following nomenclature has been adopted: when referring to a chimera, the notation from left to right follows the N to C terminus of the chimera. For example, the notation "CCR3/2" indicates that the N terminus of the chimera is derived from CCR3, while the C terminus is derived from CCR2. Analogously, the notation "CCR2/3" indicates that the N terminus of the chimera is derived from CCR2, while the C terminus is derived from CCR3.

II.A. Chimeric CCR3/2 Receptor

By combining a segment comprising the first residue of the N-terminus through at least the last residue of the seventh TM-spanning region of CCR3 with all or a portion of the cytoplasmic tail of CCR2, for example from the first intracellular non-TM residue to the last residue of the C terminus, most if not all of the ligand binding properties of such a CCR3/2 chimera will not differ significantly from those of intact wild-type CCR3. Similarly, the signalling properties of the CCR3/2 chimera will not significantly differ from those of the intact wild-type CCR2. The generation of a chimeric receptor with minimal changes to the N terminal/TM region and the C terminal cytoplasmic tail that demonstrates both adequate ligand binding ability and functional signalling capability is the first step in this process.

The importance of preserving a correct seventh TM domain to maintain receptor binding characteristics is demonstrated by a GPCR that ends at the seventh TM domain and has no cytoplasmic tail, namely mammalian gonadotropin-releasing hormone receptor. The mammalian gonadotropin-releasing hormone receptor (GnRHR) is the only known GPCR in which the C-terminal tail is absent (see, e.g., Eidne et al., (1992) *Mol. Cell. Endocrinol.* 90:R5-R9) and yet continues to bind ligand and to signal appropriately (see, e.g., Heding et al., (1998) *J. Biol. Chem.* 273(19): 11472-11477). In 1999, Flanagan et al. reported that minor changes introduced into the seventh TM domain of a mammalian GnRHR had dramatic effects upon receptor expression and G-protein coupling (Flanagan et al., (1999) *J. Biol. Chem.* 274(41):28880-86). In another study, Brothers et al. demonstrated that residues within the seventh TM domain of mammalian GnRHR are important for ligand binding as well (Brothers et al., (2002) *Mol. Cell. Endocrinol.* 190:19-27).

In contrast to the importance of maintaining the correct seventh TM domain, the addition of a C-terminal tail from other GPCRs to the mammalian GnRHR does not alter its ligand binding properties, but the addition does change how the receptor responds to ligand either in terms of the receptor internalization rates or signalling response (Willars et al., (1999) *J. Biol. Chem.* 274(42) 30146-53; Heding et al., (1998) *J. Biol. Chem.* 273(19):11472-77). It is not possible, however, to add any C-terminus to a "tail-less" GPCR without introducing the potential to disrupt expression of the receptor of interest, since merely changing the stop codon by changing the frame of the protein just upstream of the native stop codon can result in a non-expressed receptor (Heding et al., (1998) *J. Biol. Chem.* 273(19):11472-77).

Bearing the above in mind, an approach to producing a functional chimeric chemokine receptor would avoid changes to the seventh transmembrane region and utilize a conservative substitution for the C-terminus so as to minimize any changes in receptor internalization and signalling. The chimeric receptors of the present invention, therefore, incorporate no changes to the seventh transmembrane region of CCR3, while introducing a conservative substitution into the C-terminus by replacing the C-terminus of one chemokine receptor (e.g., CCR3 or CCR2) with that of another (e.g., CCR2 or CCR3, respectively). In this regard, it is predicted that replacing the C-terminus of CCR2 or CCR3 with that of another chemokine receptor would yield a functional receptor with regard to signalling, with little if any change in ligand binding characteristics.

In one embodiment of a chimera of the present invention, such a chimera was formed, namely a CCR3/2 chimera. This chimera comprises the N-terminus through the last residue of the seventh TM-spanning region of CCR3 (GenBank Accession No. U28694), namely residues 1-310, which is joined with the intracellular cytoplasmic tail of CCR2 isoform B, namely residues 315-360, in order to form a 356 residue chimera. Eighty-seven percent of the amino acid sequence of the chimera is derived from CCR3, while 13% of the chimera is derived from CCR2 isoform B. Similarly, 87% of the nucleic acid sequence of the chimera is derived from CCR3, while 13% of the chimera is derived from CCR2 isoform B. The CCR3/2 chimera shares 55% amino acid identity with CCR2 isoform A (GenBank Accession No. AF545480) and 62% identity with CCR2 isoform B (GenBank Accession No. U03905). The overall homology between the nucleic acid sequence of the human CCR3/2 chimera open reading frame and human CCR2 isoform A open reading frame is approximately 60%. Additionally, the overall homology between the open reading frames of the human CCR3/2 chimera and human CCR2 isoform B is approximately 68%.

A CCR3/2 chimera of the present invention can be employed in a variety of roles. In one example, this chimera can be employed to explore the biology of chemokine (i.e., eotaxin) stimulation of receptors and to discern the ligand binding characteristics of a particular receptor while avoiding the use of the native downstream signalling apparatus of the cognate receptor (i.e., CCR3). In another example, such a chimera can be employed in screening one or more test compounds that may inhibit binding of eotaxin to likely binding sites on the CCR3 region of the chimeric molecule. Such inhibitory compounds could be useful in the prevention and/or treatment of conditions that may result from overstimulation of the cognate receptor (i.e., CCR3), such as rhinitis and/or asthma.

Another advantage of the CCR3/2 chimera is that it can be employed in recombinant non-eosinophil system.

As described herein, a chimeric chemokine receptor of the present invention comprises not only the extracellular N terminal region of a receptor, but also the complete transmembrane region. More particularly, a chemokine receptor of the present invention comprises all seven TM helices. No other chimera known to the present inventors incorporates this complete region. As discussed herein above, most known chemokine chimeras incorporate only the extracellular N terminal region and do not incorporate the full seven helix TM region.

As shown in FIG. 1, a CCR3/2 chimera of the present invention exhibited eotaxin binding. The binding observed was very similar to that exhibited by the wild-type intact receptor in eosinophils. This observation exemplifies an advantage of the chimeras of the present invention, namely that the chimeras of the present invention can be studied, and candidate modulators identified, in a non-eosinophil system.

Further, in binding studies Compound 1 was observed to compete with eotaxin for binding to the CCR3 extracellular fragment (see Example 6). The results of this set of experiments indicate that such a chimera could be employed in a screening procedure designed to identify inhibitors of eotaxin binding.

II.B. Chimeric CCR2/CCR3 Polypeptide

The same approach presented above regarding the formation of a CCR3/2 chimera was employed to form a CCR2/3 chimera. More specifically, the N terminus through the last residue of the seventh TM-spanning region of CCR2 was joined with the cytoplasmic tail of CCR3. As exemplified herein, a CCR2/CCR3 chimera can be formed by employing the methods that were employed to construct a CCR3/CCR2 chimera of the present invention. Based on the binding study results presented herein for a CCR3/2 chimera (see FIG. 1 and Example 6), it is expected that most if not all of the ligand binding properties of the CCR2/3 chimera will not differ from that of intact wild-type CCR2.

Like the CCR3/2 chimera, a CCR2/3 chimera can be employed to identify inhibitors of CCR2 cognate ligands, in various screening operations and to study the biology of receptor binding.

II.C. Other Chimeric Chemokine Receptors

The present invention is not limited to the particular embodiments disclosed. To the contrary, it is contemplated that any pair of chemokine receptors could be employed in the generation of a binary chimeric. A binary chimera of the present invention generally comprises at least the contiguous extracellular and transmembrane region, which will be derived from one chemokine receptor. Joined to this region is all or a portion of the intracellular region derived from a second chemokine receptor. As in the case of a CCR2/CCR3, a chimeric chemokine receptor can be formed by employing the methods exemplified herein for the construction of a CCR3/2 chimeric chemokine receptor.

Binary chimeras comprising a contiguous sequence comprising at least the extracellular and TM sequence derived from one chemokine receptor are preferred for the reasons presented herein. For example, the ligand binding profile of a binary chimera of the present invention is similar to that of the wild type receptor from which the N terminus of the chimera is derived (see FIG. 1). Additionally, the signalling profile is similar to that of the wild type receptor from which the C terminus of the chimera is derived. Thus the chimeras of the present invention can be useful in screening for modulators of receptor binding and receptor-mediated signalling. These chimeras additionally feature the advantage that they are recombinant and can be expressed in an eosinophil-free system.

Further, the results of the competition experiments with a CCR3/2 chimera (see FIG. 1 and Example 6) indicate that chimeras comprising sequences derived from other chemokine receptors and GPCRs may be useful in screening assays designed to identify inhibitors of chemokine binding to the extracellular cognate receptor of the chimera.

III. Equivalents of the Chimeras of the Present Invention

Those of ordinary skill in the art will recognize and/or be able to ascertain and/or prepare, using no more than routine experimentation, many equivalents of the polypeptides of the present invention described herein, as well as polynucleotides encoding the polypeptides of the present invention. Such equivalents, some of which are described herein below, are encompassed by the claims.

III.A. Nucleic Acid Equivalents

Nucleic acid equivalents can share a degree of homology with one or more other polynucleotides, such as those encoding the chimeras of the present invention. The term "homology" refers to a degree of complementarity. There may be partial homology or complete homology, wherein complete homology is equivalent to identity. A partially complementary sequence that at least partially inhibits an identical sequence from hybridizing to a target nucleic acid is referred to as the functional term "substantially homologous". The inhibition of hybridization of the completely complementary sequence to the target sequence may be examined using a hybridization assay (for example, Southern or Northern blot, solution hybridization, and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding may be tested by the use of a second target sequence which lacks even a partial degree of complementarity (for example, less than about 30% identity). In the absence of non-specific binding, the probe will not hybridize to the second non-complementary target sequence.

Those having skill in the art will know how to determine percent identity between/among sequences using, for example, algorithms such as those used in the GAP computer program (Needleman & Wunsch, (1970) *J. Mol. Biol.* 48(3):443-53) or based on the CLUSTALW computer program (Thompson et al., (1994) *Nucleic Acid Res.* 2(22): 4673-4680), or FASTDB, (Brutlag et al., 1990, *Comp. App. Biosci.* 6:237-245), as known in the art. Although the FASTDB algorithm typically does not consider internal non-matching deletions or additions in sequences, i.e., gaps, in its calculation, this can be corrected manually to avoid an overestimation of the percent identity. GAP and CLUSTALW, however, do take sequence gaps into account in their identity calculations.

Also available to those of ordinary skill in the art are the BLAST and BLAST 2.0 algorithms (Altschul et al., (1977) *Nuc. Acids Res.* 25:3389-3402 and Altschul et al., (1990) *J. Mol. Biol.* 215:403-410). The BLASTN program for nucleic acid sequences uses as defaults a wordlength (W) of 11, an expectation (E) of 10, M=5, N=4, and a comparison of both strands.

III.B. Polypeptide Equivalents

Polypeptide equivalents of the chimeric polypeptides of the present invention are also encompassed by the present invention. For example, a polypeptide that shares a degree (but less than 100%) of identity or similarity with a chimera of the present invention is referred to as an equivalent.

For amino acid sequences, percent similarity and identity can be determined, for example, by employing the BLASTP program. The BLASTP program uses as defaults a wordlength (W) of 3, and an expectation (E) of 10. The BLOSUM62 scoring matrix (Henikoff & Henikoff, (1989) *Proc. Natl. Acad. Sci. U.S.A.* 89:10915) uses alignments (B) of 50, expectation (E) of 10, M=5, N=4, and a comparison of both strands.

A polypeptide equivalent can be, for example, a structural equivalent. A structural equivalent is a polypeptide that retains an equivalent structure either at the local level or at the global level, or both, to a reference polypeptide, but does not share 100% sequence identity or similarity. For example, a polypeptide into which one or more conservative substitutions have been introduced may have an amino acid sequence that is different from that of a reference sequence, while still retaining an overall equivalent structure, at the global and/or local level. Such polypeptides are referred to as structural equivalents of the reference polypeptide.

III.C. Biological Equivalents

Biological equivalents of the polypeptides of the present invention form yet another aspect of the present invention. A biological equivalent is a polypeptide that exhibits the same biological activity, although not necessarily to the same degree, as a reference polypeptide (e.g., a chimeric polypeptide of the present invention). A biological equivalent can comprise more, fewer or different amino acids that those found in the reference polypeptide.

IV. Polynucleotides Encoding Polypeptides of the Present Invention

Nucleic acids of the present invention, including those encoding a wild-type chemokine receptor or a chimeric chemokine receptor of the present invention, can be cloned, synthesized, recombinantly altered, or combinations thereof. Standard recombinant DNA and molecular cloning techniques used to isolate nucleic acids are well known in the art. Exemplary, non-limiting methods are described, for example, by Sambrook et al., *Molecular Cloning: A Laboratory Manual*, (3$^{rd}$ ed.) Cold Spring Harbor Laboratory Press, Cold Spring Harbor, N.Y., (2001); by Silhavy et al., *Experiments with Gene Fusions*, Cold Spring Harbor Laboratory Press, Cold Spring Harbor, N.Y., (1984); by *Current Protocols in Molecular Biology*, (Ausubel et al., eds.), Greene Publishing Associates and Wiley-Interscience, New York (2002); and by Glover, (ed.) (1985) *DNA Cloning: A Practical Approach*, MRL Press, Ltd., Oxford, U.K, all of which are incorporated herein by reference. Site-specific mutagenesis can be used to create base pair changes, deletions, or small insertions are also known in the art (see, e.g., Adelman et al., (1983) *DNA* 2:183; Sambrook et al., *Molecular Cloning: A Laboratory Manual*, (3$^{rd}$ ed.) Cold Spring Harbor Laboratory Press, Cold Spring Harbor, N.Y., (2001)).

Sequences disclosed or detected by the methods of the present invention can be detected, subcloned, sequenced, and further evaluated by any technique known in the art using any method usually applied to the detection and/or characterization of a specific DNA sequence including but not limited to dideoxy sequencing, PCR, oligomer restriction (Saiki et al., (1985) *Bio/Technology* 3:1008-1012, incorporated herein by reference), allele-specific oligonucleotide (ASO) probe analysis (Conner et al., (1983) *Proc. Natl. Acad. Sci. U.S.A.* 80:278, incorporated herein by reference), and oligonucleotide ligation assays (OLAs) (Landgren et. al., (1988) *Science* 241:1007, incorporated herein by reference). Molecular techniques for DNA analysis have been reviewed (Landgren et. al., (1988) *Science* 242:229-237, incorporated herein by reference) and can be employed in the present invention.

In one aspect, the present invention relates to vectors comprising the polynucleotides of the present invention (such as a vector encoding a chimera of the present invention), host cells, and the production of polypeptides by recombinant techniques. The vector can be, for example, a phage, plasmid, viral, or retroviral vector. Retroviral vectors can be replication competent or replication defective. In the latter case, viral propagation generally will occur only in complementing host cells.

A polynucleotide can be joined with a vector comprising a selectable marker for propagation in a host. Generally, a plasmid vector can be introduced in a precipitate, such as a calcium phosphate precipitate, or in a complex with a charged lipid. If the vector is a virus, it can be packaged in vitro using an appropriate packaging cell line and then transduced into host cells.

The polynucleotide insert can be operatively linked to an appropriate promoter, such as the phage λ PL promoter, the *E. coli* lac, trp, phoA and tac promoters, the SV40 early and late promoters and promoters of retroviral LTRs, to name a few. Other suitable promoters will be known to those of ordinary skill in the art. The expression constructs can further comprise sites for transcription initiation, termination, and, in the transcribed region, a ribosome binding site for translation. The coding portion of the transcripts expressed by the constructs can include a translation initiating codon at the beginning and a termination codon (UAA, UGA or UAG) appropriately positioned at the end of the polypeptide to be translated.

An expression vector can comprise at least one selectable marker. Such markers include dihydrofolate reductase, G418 or neomycin resistance for eukaryotic cell culture and tetracycline, kanamycin or ampicillin resistance genes for culturing in *E. coli* and other bacteria.

Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Examples of vectors that can be employed in a bacterial system include pQE70, pQE60 and pQE-9, (available from QIAGEN, Inc., Chatsworth, Calif., USA); pBluescript vectors, Phagescript vectors, pNH8A, pNH16a, pNH18A, pNH46A (available from Stratagene Cloning Systems, Inc., La Jolla, Calif., USA); and ptrc99a, pKK223-3, pKK233-3, pDR540, pRIT5 (available from Pharmacia, Piscataway, N.J., USA).

Examples of eukaryotic vectors that can be employed include pWLNEO, pSV2CAT, pOG44, pXT1 and pSG available from Stratagene; and pSVK3, pBPV, pMSG and pSVL available from Pharmacia (Piscataway, N.J., USA).

Examples of expression vectors that can be employed in a yeast system include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif., USA). Other suitable vectors will be readily apparent to one of ordinary skill in the art.

Introduction of the construct into the host cell can be mediated by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology*, ($2^{nd}$ ed.) Appleton & Lange, Norwalk, Conn. (1994). It is specifically contemplated that the polypeptides of the present invention can be expressed by a host cell lacking a recombinant vector.

In addition to encompassing host cells containing the vector constructs discussed herein, the present invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with a polynucleotide of the present invention, and which activates, alters, and/or amplifies endogenous polynucleotides. For example, techniques known in the art can be used to operably associate a heterologous control region (e.g., promoter and/or enhancer) and endogenous polynucleotide sequences via homologous recombination, resulting in the formation of a new transcription unit (see, e.g., U.S. Pat. No. 5,641,670; U.S. Pat. No. 5,733,761; PCT Publication No. WO 96/29411; PCT Publication No. WO 94/12650; Koller et al., (1989) *Proc. Natl. Acad. Sci. USA* 86:8932-8935; and Zijlstra et al., (1989) *Nature* 342:435-438, all of which are incorporated herein by reference).

A nucleic acid molecule encoding a native chemokine receptor or a chimeric chemokine receptor of the present invention can be identified and isolated using standard methods, such as those described by Sambrook et al. (1989). For example, reverse-transcriptase PCR (RT-PCR) can be employed to isolate and/or clone cDNAs of interest. In this method, oligo-dT can be employed as a primer in a reverse transcriptase reaction to prepare first-strand cDNAs from isolated RNA that contains RNA sequences of interest, e.g., RNA isolated from human tissue. RNA can then be isolated by methods known to those of ordinary skill in the art, e.g., using TRIZOL reagent (GIBCO-BRL/Life Technologies, Gaithersburg, Md.). Transcribed first-strand cDNAs are then amplified in PCR reactions.

The products of each PCR reaction can then be separated via an agarose gel, gel-purified and cloned directly into a suitable vector, such as a known plasmid vector. The resultant plasmids are subjected to restriction endonuclease and dideoxy sequencing of double-stranded plasmid DNAs. When the accuracy of the cloned sequence is ascertained, the plasmid can be introduced into a suitable expression system, such as a bacterial expression system, as described herein.

V. Polypeptides of the Present Invention

The generation of a chimeric chemokine receptor forms an aspect of the instant invention. In some embodiments, a chimeric chemokine receptor can comprise a CCR2 polypeptide or a portion of a CCR2 polypeptide, which can be joined to a candidate polypeptide or a suitable region of the candidate polypeptide, for example a CCR3 polypeptide. The fusion can be made such that either the CCR2 or the CCR3 forms the N terminus of the chimera, with the provision that the chemokine receptor segment employed as the N terminus comprises the extracellular region as well as at least the complete TM region of the chemokine receptor. The C terminal segment of the chimeric receptor can comprise all or a portion of the intracellular region of a chemokine receptor that is different from the receptor used to form the N terminus of the chimeric chemokine receptor.

The application of site-directed mutagenesis and the assembly of chemokine receptors that comprise domains from two or more different chemokine receptors (i.e., chimeric receptors) has been employed as a strategy for gaining a better understanding of the structure-function relationship in GPCRs (see, e.g., Jackson, (1991) *Pharmacol. Ther.* 50(3):425-42; Peiper et al., (1997) *Method Enzymol.* 288: 56-70). Some representative strategies to assemble chimeric polypeptides, such as chimeric chemokine receptors, include overlap polymerase chain reaction (overlap PCR), ligation-PCR, and PCR mutagenesis in which unique restriction sites are introduced at desired points of ligation (Peiper et al., (1997) *Method Enzymol.* 288: 56-70). In one aspect of the present invention, as described herein, PCR mutagenesis with the introduction of unique restriction sites at points of desired ligation was employed.

Although these various techniques have been employed in the art to join domains from different chemokines, the generated chimeras did not comprise a contiguous sequence comprising the extracellular sequence through at least the seventh TM sequence of one chemokine receptor joined with all or a portion of a intracellular region of a second chemokine receptor.

Recombinant expression of a chimeric polypeptide of the present invention, or a fragment thereof, requires the construction of an expression vector comprising a polynucleotide that encodes such a polypeptide. Once a polynucleotide encoding a chimeric polypeptide, or portion thereof has been obtained, a vector for the production of the polypeptide can be produced by recombinant DNA technology using techniques known in the art. Methods for preparing a protein by expressing a polynucleotide containing a chimeric polypeptide-encoding nucleotide sequence are described herein.

The polypeptides of the present invention, including the chimeric chemokine receptors, can be prepared in a variety of ways. The suitability of each method described herein or known to those of ordinary skill in the art will be clear to those of ordinary skill in the art upon consideration of the present disclosure. Several methods of producing a polypeptide of the present invention are described in the paragraphs that follow.

The polypeptides of the present invention, including both wild-type chemokine receptors and chimeras, as well as fragments thereof, can be chemically synthesized in whole or part using techniques that are known in the art (see, e.g., Creighton, *Proteins: Structures and Molecular Principles*, (2$^{nd}$ ed.) W.H. Freeman & Co., New York, (1993), incorporated herein by reference).

Additionally, methods known to those of ordinary skill in the art can be employed to construct expression vectors comprising a chimeric polypeptide-coding sequence and appropriate transcriptional and translational control signals. These methods include in vitro recombinant DNA techniques, as described herein, synthetic techniques and in vivo recombination/genetic recombination (see, e.g., the techniques described in Sambrook et al., *Molecular Cloning: A Laboratory Manual*, (3$^{rd}$ ed.) Cold Spring Harbor Laboratory Press, Cold Spring Harbor, N.Y., USA (2001) and *Current Protocols in Molecular Biology*, (Ausubel et al., eds.), Greene Publishing Associates and Wiley-Interscience, New York (2002), both of which are incorporated herein by reference. The present invention thus encompasses replicable vectors comprising a nucleotide sequence encoding a chimeric chemokine receptor of the present invention, which can be operably linked to a promoter.

An expression vector formed pursuant to the present invention can be transferred to a host cell by conventional techniques (e.g., precitiation or electroporation) and the transfected cells are then cultured by conventional techniques to produce a polypeptide of the present invention. Thus, the present invention comprises host cells comprising a vector comprising a polynucleotide encoding a chimeric chemokine receptor of the present invention, which can be operably linked to a promoter.

A variety of host-expression vector systems can be employed to express a chimeric chemokine receptor of the present invention. Such host-expression systems represent vehicles by which a coding sequence of interest can be produced and subsequently purified, but also represent cells that may, when transformed or transfected with the appropriate nucleotide coding sequences, express a chimeric chemokine receptor of the present invention in situ. Suitable cells include but are not limited to microorganisms such as bacteria (e.g., *E. coli, B. subtilis*) transformed with recombinant bacteriophage DNA, plasmid DNA or cosmid DNA expression vectors containing a chimeric chemokine receptor coding sequence; yeast (e.g., *Saccharomyces, Pichia*) transformed with recombinant yeast expression vectors containing a chimeric chemokine receptor coding sequence; insect cell systems infected with recombinant virus expression vectors (e.g., baculovirus) containing a chimeric chemokine receptor coding sequence; plant cell systems infected with recombinant virus expression vectors (e.g., cauliflower mosaic virus, (CaMV); tobacco mosaic virus, (TMV)) or transformed with recombinant plasmid expression vectors (e.g., Ti plasmid) containing a chimeric chemokine receptor coding sequence; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Under some conditions it might be desirable that bacterial cells such as *Escherichia coli*, or eukaryotic cells are used for the expression of a recombinant chimeric polypeptide. For example, mammalian cells such as Chinese hamster ovary cells (CHO), in conjunction with a vector such as the major intermediate early gene promoter element from human cytomegalovirus is an effective expression system (Foecking et al., (1986) *Gene* 45:101; Cockett et al., (1990) *Bio/Technology* 8:2).

In bacterial systems, a number of expression vectors can be advantageously employed, depending upon the use intended for the chimeric polypeptide being expressed. For example, when a large quantity of such a protein is to be produced, for example for the generation of a pharmaceutical composition comprising a chimeric polypeptide (such as a CCR3/CCR2 or CCR2/CCR3 chimeric polypeptide, as described herein), vectors that direct the expression of high levels of fusion protein products that are readily purified can be desirable. Such vectors include, but are not limited to, the *E. coli* expression vector pUR278 (Ruther et al., (1983) *EMBO J.* 2:1791), in which a chimeric chemokine receptor coding sequence can be ligated individually into the vector in frame with the lac Z coding region so that a fusion protein is produced; pIN vectors (Inouye & Inouye, (1985) *Nucleic Acids Res.* 13:3101-3109; Van Heeke & Schuster, (1989) *J. Biol. Chem.* 24:5503-5509); and the like. pGEX vectors can also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or Factor Xa protease cleavage sites so that the cloned target gene product can be released from the GST moiety.

In an insect system, Autographa californica nuclear polyhedrosis virus (AcNPV) can be used as a vector to express foreign genes. The virus grows in *Spodoptera frugiperda* cells. A chimeric polypeptide coding sequence may be cloned individually into non-essential regions (for example the polyhedrin gene) of the virus and placed under control of an AcNPV promoter (for example the polyhedrin promoter).

In mammalian host cells, a number of viral-based expression systems can be employed. In cases where an adenovirus is used as an expression vector, a chimeric polypeptide coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the chimeric polypeptide in infected hosts. (see, e.g., Logan & Shenk, (1984) *Proc. Natl. Acad. Sci. U.S.A.* 81:355-359). Specific initiation signals may also be required for efficient translation of inserted chimeric chemokine receptor coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., (1987) *Method Enzymol.* 153:51-544).

In addition, a host cell strain can be chosen that modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO, VERY, BHK, Hela, COS, MDCK, 293, 3T3, W138, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is often desirable. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express a chimeric chemokine receptor. Such engineered cell lines may be particularly useful in screening and evaluation of compounds that interact directly or indirectly with a chimeric chemokine receptor.

A number of selection systems can be used in the process of expressing a chimeric chemokine receptor of the present invention. Such systems can indicate a successful transformation event. For example, the herpes simplex virus thymidine kinase (Wigler et al., (1977) *Cell* 11:223), hypoxanthine-guanine phosphoribosyltransferase (Szybalska & Szybalski, (1992) *Proc. Natl. Acad. Sci. U.S.A.* 48:202), and adenine phosphoribosyltransferase (Lowy et al., (1980) *Cell* 22:817) genes can be employed in tk-, hgprt- or aprt-cells, respectively. Also, anti-metabolite resistance can be used as the basis of selection for the following genes: dhfr, which confers resistance to methotrexate (Wigler et al., (1980) *Proc. Natl. Acad. Sci. U.S.A.* 77:357; O'Hare et al., (1981) *Proc. Natl. Acad. Sci. U.S.A.* 78:1527); gpt, which confers resistance to mycophenylic acid (Mulligan & Berg, (1981) *Proc. Natl. Acad. Sci. U.S.A.* 78:2072); neo, which confers resistance to the aminoglycoside G-418 (*Clinical Pharmacy* 12:488-505; Wu & Wu, (1991) *Biotherapy* 3:87-95; Tolstoshev, (1993) *Ann. Rev. Pharmacol. Toxicol.* 32:573-596; Mulligan, (1993) *Science* 260:926-932; and Morgan & Anderson, (1993) *Ann. Rev. Biochem.* 62:191-217; *TIB TECH* 11(5):155-215, May, 1993); and hygro, which confers resistance to hygromycin (Santerre et al., (1984) *Gene* 30:147). Methods known in the art of recombinant DNA technology can be applied to select the desired recombinant clone, and such methods are described, for example, in *Current Protocols in Molecular Biology*, (Ausubel et al., eds.), Greene Publishing Associates and Wiley-Interscience, New York (2002); Kriegler, *Gene Transfer and Expression. A Laboratory Manual*, Stockton Press, New York, N.Y., USA (1990); *Current Protocols in Human Genetics*, (Dracopoli et al., eds.), John Wiley & Sons, New York, N.Y., USA (1994), Chapters 12 and 13; and Colberre-Garapin et al., (1981) *J. Mol. Biol.* 150:1.

The expression levels of a chimeric chemokine receptor can be increased by vector amplification (for a review, see Bebbington & Hentschel, in *DNA Cloning*, vol. 3, Academic Press, New York (1987)). When a marker in the vector system expressing a chimeric polypeptide is amplifiable, an increase in the level of inhibitor present in culture of host cell will increase the number of copies of the marker gene. Since the amplified region is associated with the chimeric polypeptide gene, production of the chimeric polypeptide will also increase (Crouse et al., (1983) *Mol. Cell. Biol.* 3:257).

Depending on the host/vector system utilized, any of a number of suitable transcription and translation elements, including constitutive and inducible promoters, can be used in the expression vector. As noted, for example, when cloning in bacterial systems, inducible promoters such as pL of bacteriophage λ, plac, ptrp, ptac (ptrp-lac hybrid promoter) and the like can be employed. When cloning in insect cell systems, promoters such as the baculovirus polyhedrin promoter can be employed. When cloning in mammalian cell systems, promoters derived from the genome of mammalian cells (e.g., metallothionein promoter) or from mammalian viruses (e.g., the adenovirus late promoter or the vaccinia virus 7.5K promoter) can be employed. When generating cell lines that contain multiple copies of the tyrosine kinase domain DNA, SV40-, BPV- and EBV-based vectors can be used with an appropriate selectable marker. Representative methods of producing a polypeptide of the present invention will be apparent to those of ordinary skill in the art, upon consideration of the present disclosure, and are also described herein.

Once a chimeric polypeptide of the present invention has been produced by an animal, chemically synthesized, or recombinantly expressed, it can be purified by any method known in the art for purification of a protein, for example, by chromatography (e.g., anion or cation exchange chromatography, phosphocellulose chromatography, hydrophobic interaction chromatography, affinity chromatography, hydroxylapatite chromatography, lectin chromatography, ion exchange, sizing column chromatography, high performance liquid chromatography ("HPLC"), etc.), centrifugation, differential solubility, or by any other standard technique for the purification of proteins. In addition, a chimeric polypeptide of the present invention or fragments thereof can be joined to heterologous polypeptide sequences described herein or otherwise known in the art, to facilitate purification.

In some embodiments, a chimeric chemokine receptor of the present invention can be purified according to standard procedures of the art, including ammonium sulfate precipitation, ethanol precipitation, acid extraction, affinity chromatography, gel electrophoresis and the like (see generally *Protein Purification: Principles and Practice* ($3^{rd}$ ed.), Springer-Verlag, New York (1994)).

Polypeptides of the present invention, including their secreted forms, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

As noted herein above, the polypeptides of the present invention need not be expressed recombinantly and can be chemically synthesized using techniques known in the art (e.g., see Creighton, *Proteins: Structures and Molecular Principles*, ($2^{nd}$ ed.) W.H. Freeman & Co., New York, (1993), and Hunkapiller et al., (1984) *Nature* 310:105-111, both of which are incorporated herein by reference). For example, a polypeptide comprising a fragment of a polypeptide sequence of the present invention can be synthesized by employing a peptide synthesizer.

If desired, nonclassical amino acids or chemical amino acid analogs can be introduced as a substitution or addition into the polypeptide sequence. Representative non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, an incorporated amino acid can be D (dextrorotary) or L (levorotary).

The present invention encompasses chimeric chemokine receptors that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Chemical modifications can be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. The polypeptides can also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the present invention are chemically modified derivatives of the polypeptides of the present invention that can provide additional advantages such as increased solubility, stability and circulating time of the polypeptide, or decreased immunogenicity (see U.S. Pat. No. 4,179,337, incorporated herein by reference). The chemical moieties for derivitization can be selected from water soluble polymers such as polyethylene glycol, ethylene glycol/propylene glycol copolymers, carboxymethylcellulose, dextran, polyvinyl alcohol and the like. The polypeptides can be modified at random positions within the molecule, or at predetermined positions within the molecule and can include one, two, three or more attached chemical moieties.

Polyethylene glycol molecules (or other chemical moieties) can be attached to the protein with consideration for the effect on functional or antigenic domains of the protein. There are a number of attachment methods available to those skilled in the art (see, e.g., EP 0 401 384 (coupling PEG to G-CSF) and Malik et al., (1992) *Exp. Hematol.* 20:1028-1035 (reporting PEGylation of GM-CSF using tresyl chloride), which are incorporated herein by reference). For example, polyethylene glycol can be covalently bound through amino acid residues via a reactive group, such as, a free amino or carboxyl group. Reactive groups are those to which an activated polyethylene glycol molecule can be bound. The amino acid residues having a free amino group can include lysine residues and the N-terminal amino acid residues; those having a free carboxyl group can include aspartic acid residues, glutamic acid residues and the C-terminal amino acid residue. Sulfhydryl groups can also be used as a reactive group for attaching the polyethylene glycol molecules. For therapeutic purposes attachment at an amino group, such as attachment at the N-terminus or lysine group, can be desirable.

One may specifically desire proteins chemically modified at the N-terminus. Using polyethylene glycol as an illustration of the present composition, one can select from a variety of polyethylene glycol molecules (by molecular weight, branching, etc.), the proportion of polyethylene glycol molecules to protein (polypeptide) molecules in the reaction mix, the type of PEGylation reaction to be performed, and the method of obtaining the selected N-terminally PEGylated protein. The method of obtaining the N-terminally PEGylated preparation (i.e., separating this moiety from other monoPEGylated moieties if necessary) can be by purification of the N-terminally PEGylated material from a population of PEGylated protein molecules. Selective proteins chemically modified at the N-terminus modification can be formed by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues can comprise functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and that can assist in targeting specific tissues in the body including, for example, diseased tissue. Exemplary materials that can be reacted with the additional functional groups include, for example, proteins, including antibodies, carbohydrates, peptides, glycopeptides, glycolipids, lectins, and nucleosides.

Moreover, the present invention also encompasses derivitization of the polypeptides of the present invention, for example, with a lipid (including cationic, anionic, polymerized, charged, synthetic, saturated, unsaturated, and any combination of the above, etc.) and/or a stabilizing agent.

VI. Representative Applications of a Chimeric Polypeptide of the Present Invention A chimeric chemokine receptor of the present invention can be employed in a variety of applications. A representative, but non-limiting, list of applications for a chimeric chemokine receptor of the present invention includes the use of these chemokine receptors in candidate ligand screening assays, pharmaceutical compositions, and signalling assays. Other applications include diagnostic and therapeutic methods.

As discussed in more detail below, a chimeric polypeptide of the present invention (e.g., a CCR3/2 or a CCR2/3 chimera) can be employed in an application either alone or in combination with other compositions.

Further discussion of some representative applications of chimeric polypeptides of the present invention follows.

VI.A. Screening Assays

In one aspect of the present invention, the chemokine receptor chimeras of the present invention can be employed in various screening assays. For example, a chimeric chemokine receptor of the present invention can be employed in an assay designed to identify compounds that inhibit or enhance binding of a cognate chemokine to a chemokine receptor that forms an element of the chimeric chemokine receptor (e.g., the extracellular N terminal segment or the intracellular C terminal segment).

In one embodiment of a ligand binding assay that can be carried out using a chimeric chemokine receptor of the present invention, a labled chemokine (e.g., $^{125}I$ RANTES and/or $^{125}I$ MIP-1) and an unlabled test compound are provided. Initially, a reference level of chemokine binding is determined, against which subsequent chemokine binding experiements is gauged. Cells expressing a chimeric chemokine receptor of the present invention can be washed with PBS and resuspended, after which labled chemokine and unlabeled test compound can be contacted with the cells. Structures other than cells can be employed, as long as the chimeric chemokine receptor is present. After an incubation period, the cells can be washed to remove unbound chemokine. The amount of labeled chemokine associated with the chimera can be determined by quantitating the amount of label associated with the chimera. When a radiolabel is employed, the quantitation can comprise assessing the amount of radioactivity associated with the chimera. A measurement of the effect of the test compound on chemokine binding can be made by comparing chemokine binding in the presence and absence of the test compound; a lower degree of chemokine binding indicates a degree of inhibition due to the presence of the test compound, while a higher degree of chemokine binding indicates enhanced binding of the chemokine due to the presence of the test compound. Additionally, competetive ligand binding assays can also be performed. Such assays can incorporate a ligand known to bind to a segment of the chemokine receptor and a test compound. Methods for performing and interpreting the results of a competitive ligand binding assay are known to those of ordinary skill in the art. Generally, chemokine binding to the target cells, such as eosinophils, can be carried out using known methodology (see, e.g., Van Riper, (1993) *J. Exp. Med.* 177:851-856). Binding can be assessed with respect to both the extracellular segment of a chimeric chemokine receptor and the intracellular segment of a chimeric chemokine receptor.

The chimeric chemokine receptors of the present invention can also be employed in intracellular signalling assays. More particularly, the chimeras can be employed to determine a degree of intracellular signalling that is induced by a test compound. Intracellular signalling assays can be of any form, although often phosphorylation or dephosphorylation of a known intracellular signalling molecule is employed and offers a convenient approach to quantitatively determining signalling levels.

In one example of an intracellular signalling assay, the hydrolysis of GTP to GDP can be assayed by standard methodology. GTP hydrolysis is an aspect of G protein-mediated signalling activity. GTP associates with G proteins and hydrolysis of GTP to GDP, in addition to the exchange of GTP for GDP. This latter process relies on a receptor, such as a chimeric chemokine receptor of the present invention.

In one embodiment of an intracellular signalling assay, labeled GTP can be employed and hydrolysis of GTP to GDP can be employed as a gauge of induced signalling. In an example of such an assay, a baseline (control) level of G protein-dependent GTP hydrolysis can be determined for a given system. A test compound can be contacted with a chimera of the present invention, and a degree of GTP hydrolysis determined. The two levels (i.e., in the presence and absence of test compound) can then be compared and the effect of the test compound on signalling can be assessed. Various labels can be employed, such as radiolabeled GTP. In a related aspect, exhange of GTP for GDP is can also be monitored.

Another signalling assay that can be employed involves monitoring the levels of a secondary messenger, such as calcium or diacylglycerol, for example. With respect to cytosolic calcium levels, a signalling event is typically associated with a transient increase in cytosolic calcium levels. Assays to determine such an increase are known in the art and can be employed to assay the effect of a test compound on intracellular signalling. An example of an system for measuring increases in cytosolic calcium levels is provided in Van Riper, (1993) *J. Exp. Med.* 177:851-856 and can be employed in the context of the present invention.

In one example of a method that can be employed in the present invention, a reference level of intracellular calcium can be measured. A chimeric chemokine receptor of the present invention, which can be disposed in a cell or other structure, is then contacted with a test compound. The level of intracellular calcium can then be determined by any convenient method and the levels compared. When a chimeric chemokine receptor of the present invention is disposed in a cell, under appropriate assay conditions a system such as FACS can be employed to assess intracellular calcium levels. An additional step of normalizing any observed fluorescence can also be performed. See, e.g., Van Riper, (1993) *J. Exp. Med.* 177:851-856 and/or Dahinden et al., (1994) *J. Exp. Med.* 179:751-756.

A chemotaxis assay can also be employed in a screening method of the present invention. Such assays are generally premised on the fact that it is known that a ligand/chemokine receptor binding event can induce the migration of cells. Suitable assays are described, for example, in Nelson et al., (1975) *J. Immunol.* 115:1650; Matsushima et al., (1989) *J. Exp. Med.* 169:1485; Jose et al., (1994) *J. Exp. Med.* 179:881-887; Kavanaugh et al., (1991) *J. Immunol.* 146: 4149-4156. In one embodiment of a chemotaxis assay, the knowledge that a ligand/chemokine receptor binding event induces leukocyte migration can also be employed.

In one particular chemotaxis assay, a cell expressing a chimeric chemokine receptor of the present invention is contacted with a test compound. The chemotactic effect of the test compound can be assayed by examining the migration, if any, of the cell following the contacting. The use of equipment adapted for chemotactic analysis, such as a TRANSWELL insert (Costar, Cambridge, Mass.), can facilitate the assay, with migrating cells localizing in the area below the insert and non-migrating cells localizing in the upper chamber of the insert.

Thus, receptor activation (i.e., intracellular signalling) can be determined by techniques described herein or otherwise known in the art. For example, receptor activation can be determined by detecting the phosphorylation (e.g., tyrosine or serine/threonine) of the receptor or its substrate by immunoprecipitation followed by western blot analysis. A representative example of a signalling assay is presented in Example 6 herein below.

VI.B. Pharmaceutical Compositions

A chimeric chemokine receptor of the present invention, with or without a therapeutic agent conjugated to it, administered alone or in combination with a cytotoxic factor, a cytokine or other biologically active moiety, including a small molecule, can be used as a therapeutic.

A chimeric chemokine receptor can be conjugated to a therapeutic moiety such as a cytotoxin, e.g., a cytostatic or cytocidal agent, a therapeutic agent or a radioactive metal ion, e.g., an alpha-emitter, such as, $^{213}$Bi. The terms "cytotoxin" and "cytotoxic agent" include any agent that is detrimental to cells. Examples of cytotoxins and cytotoxic agents include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Representative therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In addition to a role as a therapeutic agent, the present invention also encompasses chimeras of the present invention conjugated to a diagnostic agent for use in diagnostic operations. The chimeras can be used diagnostically, for example, to monitor the signalling or ligand binding, for example to determine the efficacy of a given treatment regimen. Detection can optionally be facilitated by coupling the chimera to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the chimera or indirectly, through an intermediate (such as, for example, a linker known in the art) using techniques known in the art. Examples of suitable enzymes for conucation to a chimera include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

The pharmaceutical compositions of the present invention can comprise a therapeutically effective amount of a chimera of the present invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. The formulation should suit the mode of administration.

In one embodiment, a composition is formulated in accordance with routine procedures as a pharmaceutical composition adapted for intravenous administration to human beings. Typically, compositions for intravenous administration are solutions in sterile isotonic aqueous buffer. Where necessary, a composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a composition is to be administered by infusion, it can be dispensed with an infusion bottle containing sterile pharmaceutical grade water or saline. Where a composition is administered by injection, an ampule of sterile water for injection or saline can be provided so that the ingredients may be mixed prior to administration.

The compounds of the present invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the present invention which will be effective in the treatment, inhibition and prevention of a disease or disorder associated with aberrant expression and/or activity of a polypeptide of the present invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

A pharmaceutical composition can be administered in conjunction with a pharmaceutically acceptable carrier, diluent, or excipient, to achieve any of the above-described therapeutic uses and effects. Such pharmaceutical compositions can comprise agonists, antagonists, activators or inhibitors. The compositions can be administered alone, or in combination with at least one other agent or reagent, such as a stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients, the pharmaceutical compositions can contain pharmaceutically acceptable/ physiologically suitable carriers or excipients comprising auxiliaries which facilitate processing of the active compounds into preparations that can be used pharmaceutically. Further details on techniques for formulation and administration are provided in *Remington's Pharmaceutical Sciences*, (Gennaro, ed.)20$^{th}$ ed., Mack Publishing, Easton, Pa., (2000).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents that increase the solubility of the compounds to allow for the preparation of highly concentrated solutions.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

A pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, combined with a buffer prior to use. After the pharmaceutical compositions have been prepared, they can be placed in an appropriate container and labeled for treatment of an indicated condition. For administration of a modulator, such labeling can include guidance on the amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, for example, using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient (e.g., a modulator of the present invention) that ameliorates, reduces, diminishes, or eliminates the symptoms or condition. Therapeutic efficacy and toxicity can be determined by standard pharmaceutical procedures in cell cultures or in experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions that exhibit large therapeutic indices are preferred. The data obtained from cell culture assays and animal studies are used in determining a range of dosages for human use. A representative dosage contained in a pharmaceutical composition is within a range of circulating concentrations that include the $ED_{50}$ with little or no toxicity. The dosage varies within this range depending upon the dosage form employed, the sensitivity of the patient, and the route of administration.

The practitioner, who will consider the factors related to an individual requiring treatment, will determine the exact dosage. Dosage and administration are adjusted to provide sufficient levels of the active component, or to maintain the desired effect. Factors which may be taken into account include the severity of the individual's disease state; the general health of the patient; the age, weight, and gender of the patient; diet; time and frequency of administration; drug combination(s); reaction sensitivities; and tolerance/response to therapy. As a general guide, long-acting pharmaceutical compositions may be administered every 3 to 4 days, every week, or once every two weeks, depending on half-life and clearance rate of the particular formulation. Variations in these dosage levels can be adjusted using standard empirical routines for optimization, as is well understood in the art.

As a guide, normal dosage amounts may vary from 0.1 to 100,000 micrograms (μg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors or activators. Similarly, the delivery of polynucleotides or polypeptides will be specific to particular cells, conditions, locations, and the like.

The present invention also provides a pharmaceutical pack or kit comprising one or more containers filled with one or more of the ingredients of the pharmaceutical compositions of the present invention. Optionally a notice can be associated with such container(s) in the form prescribed by a governmental agency regulating the manufacture, use or sale of pharmaceuticals or biological products, which notice reflects approval by the agency of manufacture, use or sale for human administration. Such a notice can also provide guidance on how to use the pack or kit.

VI.C. Kits for Diagnosis, Therapy and Research Applications

In one aspect of the present invention, various kits are provided. Depending on configuration, the kits of the present invention can be employed in diagnostic, therapeutic and research applications.

In one embodiment, a kit comprises a chimeric chemokine receptor of the present invention. The polypeptide can be supplied in a sterile buffer or it can be expressed in a cell line, which itself can form a component of a kit. A kit can also comprise buffers, known ligands, reagents for detecting intracellular signalling and other components. When a kit is adapted for a diagnostic application, the kit can also comprise printed material providing guidance in making a determination as to the presence, absence or likelihood of acquiring a given condition.

For example, it is known that the malfunction of one or more GPCRs (i.e., chemokine receptors) can contribute to diseases such as Alzheimer's, Parkinson, diabetes, dwarfism, color blindness, retinal pigmentosa or asthma. GPCRs (i.e., chemokine receptors) are also involved in depression, schizophrenia, sleeplessness, hypertension, anxiety, stress, renal failure and in several other cardiovascular, metabolic, neural, oncology and immune disorders (Horn & Vriend, (1998) *J. Mol. Med.* 76:464-468). They have also been shown to play a role in HIV infection (Feng et al., (1996) *Science* 272:872-877). Thus, these and other conditions can be treated and/or diagnoses by employing a kit of the present invention. In one embodiment, a kit can be employed as a research tool to study the association of the recited conditions with a chemokine receptor and in other embodiments a kit can be employed as a therapeutic and/or diagnostic tool adapted to identify and/or treat a condition, such as those recited above.

EXAMPLES

The following Examples have been included to illustrate representative modes of the present invention. Certain aspects of the following Examples are described in terms of techniques and procedures found or contemplated by the present inventors to work well in the practice of the invention. These Examples are demonstrated through the use of standard laboratory practices of the inventors. In light of the present disclosure and the general level of skill in the art, those of ordinary skill in the art will appreciate that the following Examples are intended to be exemplary only and that numerous changes, modifications and alterations can be employed without departing from the spirit and scope of the invention.

Example 1

Cloning Wildtype CCR3 from Human Monocytes

The sequences used to generate PCR primers for cloning the endogenous CCR3 receptor of human eosinophils was based upon nucleic acid sequences of Combadiere et al. (Combadiere et al., (1995) *J. Biol. Chem.* 270 (27) 16491-16494; Accession No. U28694). The PCR primers listed below; however were used to clone CCR3 from a human monocyte cDNA library and not from eosinophils. The CCR3 receptor was cloned in overlapping halves that were then joined by PCR overlap ligation reaction as described by Peiper et al. (Peiper et al., (1997) *Method Enzymol.* 288:56-70). The primers used were as follows:

```
5' CCR3 (EcoRI site in lowercase):
5' CGgaattcATGACAACCTCACTAGATACA 3'   (SEQ ID NO:7)

3' CCR3 midway:
5' GGACAATGGCCACCTACC 3'              (SEQ ID NO:8)

5' CCR3 midway:
5' GCATGTGTAAGCTCCTCTC 3'             (SEQ ID NO:9)

3' CCR3 (XbaI site in lowercase):
5' GCtctagaCTAAAACACAATAGAGAGTTCC     (SEQ ID NO:10)
```

Figure 2A:
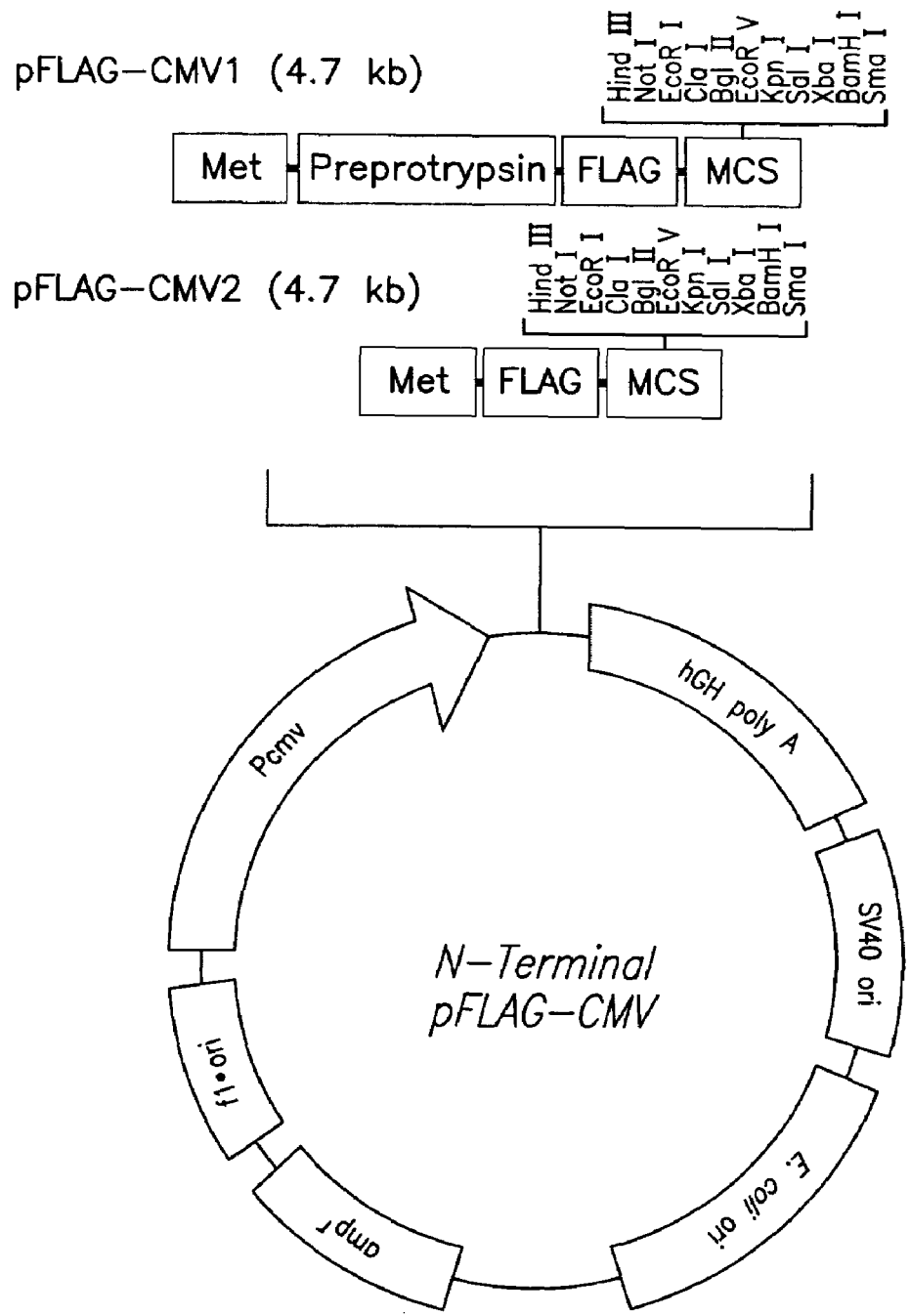
FIG. 2A is diagram depicting a pFLAG-CMV1 vector used to clone/express wild-type human CCR3.

The 5' and 3' PCR products were purified and joined as indicated above to yield a full-length CCR3 open reading frame with unique EcoRI and XbaI restriction sites at the 5' and 3' ends respectively (Ref: DMP 1953-177). The full-length open reading frame of wild-type human CCR3 obtained from human monocytes was digested with EcoRI and XbaI restriction sites and cloned into the vector pcDNA3(His) (Ref: DMP 1953-191). Subsequently, a HindIII site (in lowercase) (aagcttATG) (SEQ ID NO:25) was added at the start (ATG) codon of CCR3 and the insert open reading frame (HindIII-XbaI) was cloned in-frame into the pFLAG CMV-1 vector obtained from Sigma Chemical Company (St. Louis, Mo.) so as to add a preprotrypsin signal sequence to the 5' end of the open-reading frame. The full annotated sequence of the open reading frame within the pFLAG-CMV-1 vector is provided in FIGS. 2A and 2B. The MCS (multiple cloning site) of the vector represents an area where cDNA constructs can be inserted by using any single or any combination of the restriction sites shown. In this example, the 5' cloning site was HindIII and the 3' cloning site was XbaI, as indicated in FIGS. 2A and 2B.

Example 2

Cloning Wild-type CCR2B from Human Monocytes

The sequences used to obtain PCR primers for the purpose of cloning the human CCR2 isoform B (CCR2B) receptor were based upon the 1994 publication of Charo et al. (Charo et al., (1994) *Proc. Natl. Acad. Sci. U.S.A.* 91(7) 2752-2756 GenBank Accession No. U03905). The sequence of the primer used to amplify CCR2B at its 5' end was CGGggtaccATGCTGTCCACATCTCGTTCT (SEQ ID NO:11; an introduced KpnI restriction site is indicated by lowercase letters). The sequence of the primer used to amplify CCR2B at its 3' end was CGGggtaccTCCTCGTTT-TATAAAACCAGCC (SEQ ID NO:12; an introduced KpnI restriction site is indicated by lowercase letters). The full-length CCR2B cDNA was amplified from a human monocyte cDNA library. The resulting PCR product was digested with KpnI and cloned into the KpnI site located within the multiple cloning site (MCS) of the pFLAG CMV-1 (FIG. 2A).

Example 3

Assembling A Chimeric CCR3/2 Receptor cDNA Clone

As noted above, cDNAs for human chemokine receptors CCR3 and CCR2B were cloned from a monocyte cDNA library. Overlapping PCR products consisting of the human CCR3 gene from the N-terminus through the seventh transmembrane domain and the human CCR2B gene from the seventh transmembrane domain through the C-terminus were spliced together as described below.

Using pFLAG-CMV1/CCR3 as a template, the following primers were used to amplify a partial CCR3 cDNA encompassing the START codon (in bold) through the seventh transmembrane domain:

```
5' primer:
CCCAaagcttATGACAACCTCACTAGATAC          (SEQ ID NO:13)
(HindIII site in smallcase)

3' primer:
GCaatattTCCGGAACCTCTCTCCAAC             (SEQ ID NO:14)
(blunt-end SspI site in smallcase)
```

Using pFLAG-CMV1/CCR2B as a template, the following primers were used to amplify a partial CCR2B cDNA encompassing the seventh transmembrane domain through the STOP codon (reverse sequence in bold):

```
5' primer:
GGGatatctCTCGGTGTTCTTCCGAAAG            (SEQ ID NO:15)
(blunt-end EcoRV site in smallcase)

3' primer:
CGggatccTCTAGATTATAAACC                 (SEQ ID NO:16)
(BamHI site in smallcase)
```

Figure 3A:
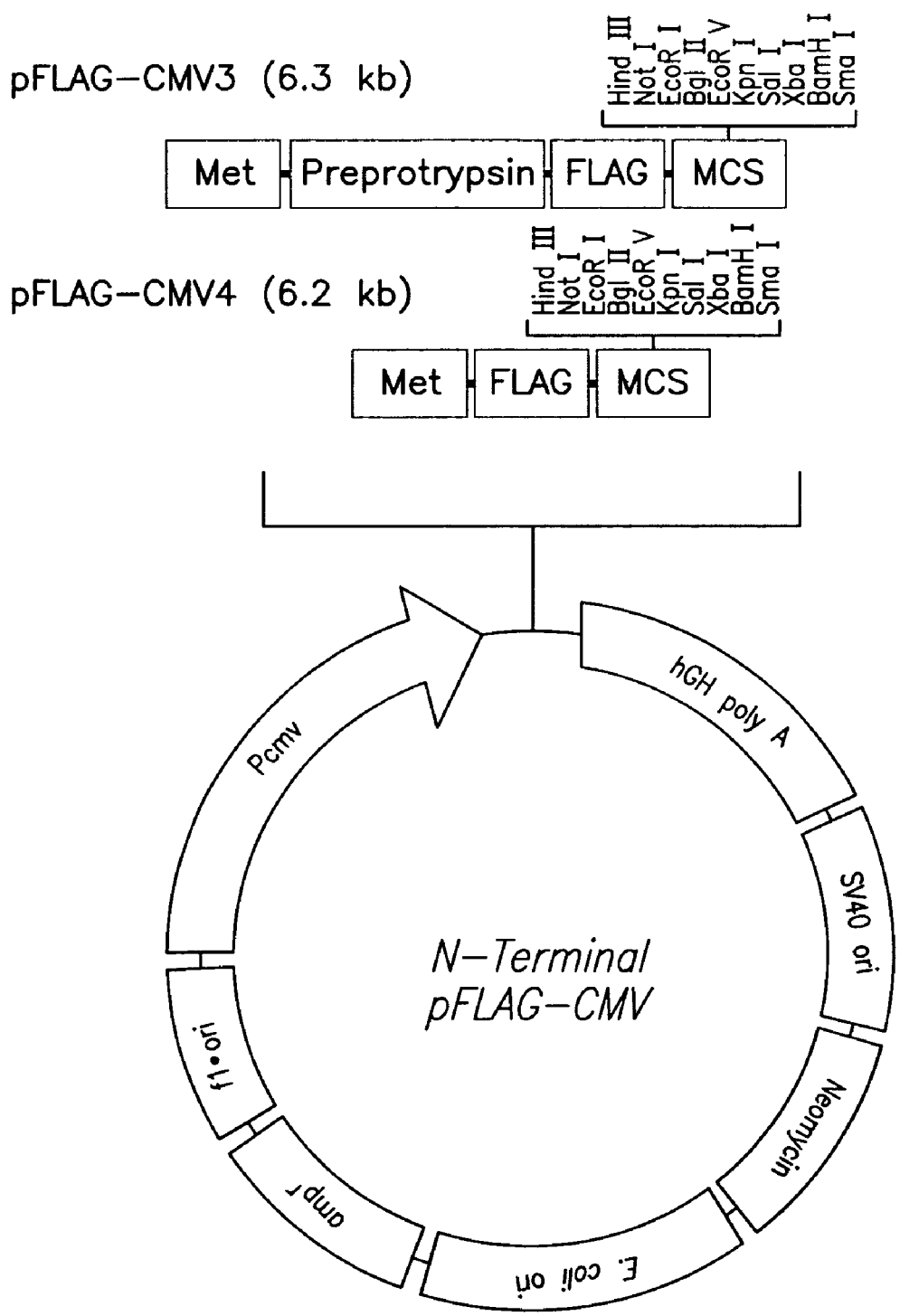
FIG. 3A is a diagram depicting a pFLAG-CMV3 vector used to clone the chimeric CCR3/2 insert.

The 5' partial CCR3 product was digested with HindIII and SspI and the 3' partial CCR2B product was digested with EcoRV and BamHI and each digested product was subsequently gel purified. These partial products were ligated into a pFLAG-CMV-3 vector (FIG. 3A) which had previously been digested with BamHI and HindIII. The two blunt-end regions (EcoRV and SspI) come together and complete the assembly of the intact CCR3/2 chimeric molecule containing seven transmembrane regions and a cytoplasmic tail in the pFLAG-CMV-3 vector.

This chimeric chemokine receptor, which was cloned into the pFLAG-CMV3 vector, differs substantially from the sequences of both human CCR3 and CCR2 at both the nucleic acid and amino acid level. At the amino acid level, the location of the C-terminal splice between human CCR3 and human CCR2 occurs such that amino acids 1-310 of the 355 amino acid CCR3 sequence are retained and joined with resiues 316-360 of the CCR2B amino acid sequence, with a tyrosine residue common to both and forming a junction site. Thus in the chimeric molecule, about 87% of the CCR3/2 amino acid composition is derived from CCR3 and about 13% of the amino acid sequence is derived from CCR2B. The total length of the CCR3/2 chimeric molecule described herein is 356 amino acids which differs both from the 355 amino acids found in CCR3 and the 360 amino acids found in CCR2 isoform B.

At the nucleic acid level, the location of the C-terminal splice between human CCR3 and human CCR2 occurs such that nucleotides 1-929 (nucleotide position 930 is synthetic, occuring in neither CCR2 nor CCR3) of the 1065 nucleotide open reading frame (ORF) of CCR3 is retained. Thus, in the chimeric molecule, about 87% of the nucleotide sequence is derived from CCR3 and about 13% of the nucleotide sequence is derived from CCR2B. Nucleotides 931-1068 (about 13%) of the chimeric molecule open reading frame derive from CCR2B. FIG. 3B depicts an alignment of CCR2B, CCR3 and the CCR2B/CCR3 chimeric protein. In the figure, black lines indicate identity, while gray lines indicate similarity. The terms "similarity and "identity" are defined herein.

Example 4

Preparation and Expansion of Cells Expressing Chimeric CCR3/2

Chinese Hamster Ovary cells (CHO-K1, American Type Culture Collection, Manassas, Va.) were grown in Ham's F10 media (Life Technologies, Grand Island, N.Y.) supplemented with 10% FBS (HyClone, Logan, Utah), 2 mM glutamine and penicillin G/streptomycin (Life Technologies, Gaithersburg, Md.). Transfections were conducted using LIPOFECTAMINE™ reagent (Life Technologies, Grand Island, N.Y.). CHO-K1 (also referred to herein as simply "CHO cells") were seeded onto 100-mm tissue culture dishes 24 hours before transfection. Cells were then washed with OPTI-MEM™ reduced serum medium (Life Technologies, Grand Island, N.Y.), incubated with transfection mixture (10 μg of pCMV3-FLAG-CCR3/2 vector DNA and 50 μl of LIPOFECTAMINE™ reagent) for 6 hours at 37° C. in a $CO_2$ incubator, and washed once with PBS before being replaced with Ham's F10 growth medium. Cells were washed 24 hours post-transfection before fresh medium was added. After 24 additional hours, G418 (Life Technologies, Grand Island, N.Y.) was added to a final concentration of 600 μg/ml. After 13 days in culture, colonies that survived selection (i.e. had retained the transfection construct) were picked for expansion and assessment of their levels of CCR3/2 expression. Colonies were initially transferred to single wells of a 96 well plate and then transferred to duplicate wells of a 24 well plate when confluent. From confluent 24 well plates, cells were expanded directly onto 60 mm and subsequently 100 mm plates. Duplicate wells of each clone were frozen back prior to expansion and testing for expression of the chimeric receptor. CHO cells are not expected to express any CCR3, thus any detected CCR3 should actually be from the CCR3/2 chimeric receptor that was transfected into the cells.

Example 5

Analysis of CCR3/2 Cell Surface Expression

Figure 4:
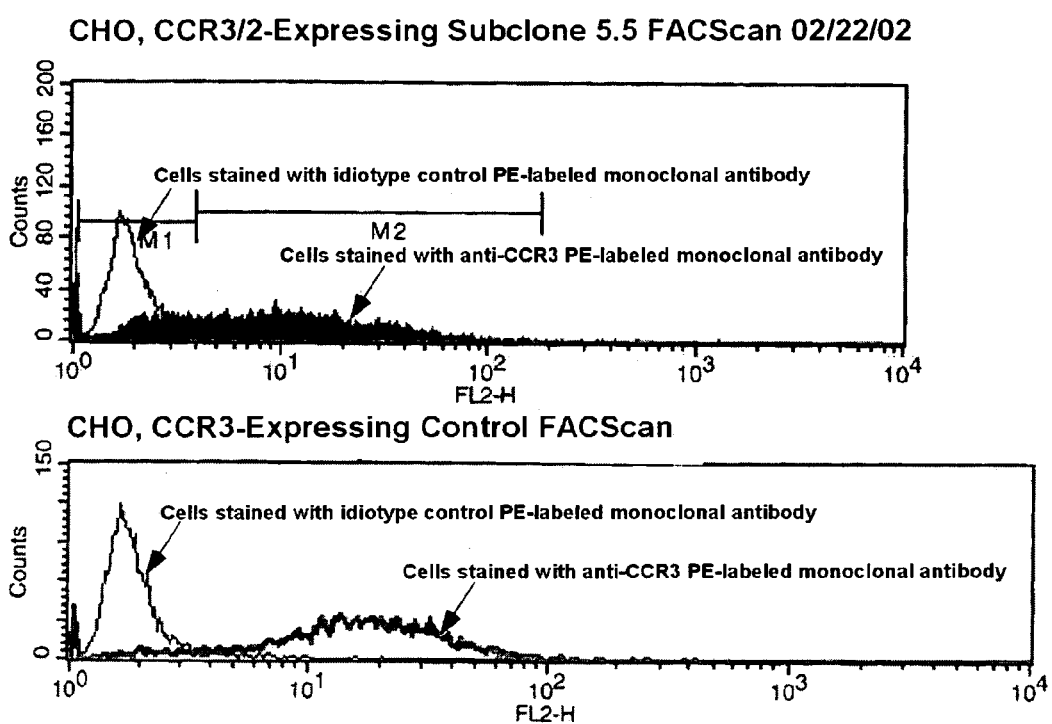
FIG. 4 is a plot depicting the results of a FACS analysis of CHO CCR3/2 line 5.5 with respect to control CHO CCR3 expressing lines.

Previous experience has demonstrated that only cells demonstrating high levels of chemokine receptor expression perform adequately in ligand binding assays. Screening for high levels of expression by FACS analysis has proven a reliable way to assess expression levels of cell surface molecules of interest in transfected cells. After expansion, each of the 24 transfected cultures was washed with $Ca^{2+}$ and $Mg^{2+}$-free PBS and dislodged from the plates by incubation in $Ca^{2+}$ and $Mg^{2+}$-free PBS containing 2 mm EDTA. Dislodged cells were resuspended at $5\times10^6$ cells/ml in $Ca^{2+}$ and $Mg^{2+}$-free PBS and incubated with 10 µg/ml of phycoerthryin (PE)-labeled rat monoclonal antibody directed against human CCR3 (R&D Systems, Minneapolis, Minn., Cat.#FAB 155P) or against an isotype matched PE-labeled rat IgG antibody control (R&D Systems, Minneapolis, Minn., Cat.#IC005P) as a control for non-specific background staining. A Becton-Dickinson FACScan was used to screen for highly expressing cells by comparing the fluorescence levels of control-labeled cells (CHO/CCR3/2 test cell lines incubated with a non-specific phycoerythrin (PE)-labeled idiotype control antibody as a test for non-specific sticking) and comparing these results with the amount of fluorescent staining detected when a specific PE-labeled anti-human CCR3 antibody was used to label the same test cells (FIG. 4, upper panel). Data obtained for a CHO clone expressing recombinant human CCR3 stained with PE-labeled anti-human CCR3 was also compared (FIG. 4, lower panel).

Of the 24 original transfected cell lines, two (clones 5 and 12) showed high levels of CCR3/2 expression and these were subsequently subcloned and re-screened by the same procedure. The results presented in FIG. 4 demonstrate significant detection of CCR3/2 by a PE-labeled anti-human CCR3 monoclonal antibody to label receptor in recombinant CHO cells. Subclones 5.5 and 5.12 showed consistently high levels of expression and a decision was made to expand and freeze both cell lines back while focusing on line 5.5 for ongoing ligand binding screens. Subclone 5.5 has been passaged over 30 times with no apparent lost in CCR3/2 expression levels.

Example 6

Testing the Ability of CCR3- or CCR3/2-Expressing Cells to Bind Eotaxin

CCR3 is normally found on eosinophils and other cells and has been demonstrated to specifically bind eotaxin (Ponath et al., (1996) *J. Clin. Invest.* 97:604). In order to compare the ability of cells expressing chimeric human CCR3/2 molecules to that of cells expressing endogenous human CCR3 to bind eotaxin, a binding assay was performed. Depending upon the questions being asked, the cells in question were either human or mouse eosinophils, CHO-K1 cells expressing recombinant CCR3 or CCR3/2, parental CHO-K1 cells or other cell types. All assay steps were conducted at room temperature. Multiscreen assay plates (#MABVN1250, Millipore Inc., Marlborough, Mass.) were incubated with 100 µl/well of blocking solution (7.5 µg/ml protamine in PBS) to block non-specific binding. After 20 minutes, the blocking solution was removed and replaced with 100 µl of binding buffer, (RPMI 1640 (Life Technologies, Grand Island, N.Y.) containing 0.1% bovine serum albumin and 20 mM HEPES buffer) and incubated for at least an additional 10 minutes.

When ready to use plate(s), the following procedure was employed. Remove the binding buffer and add the following to the well types indicated:

to TOTAL binding wells add 50 µl of binding buffer;

to NON-SPECIFIC binding wells add 50 µl of unlabeled human eotaxin to 100 nM and 1000 nM final concentration (recombinant human eotaxin—#320-EO/CF, R&D Systems, Minneapolis, Minn.) in 50 µl binding buffer;

to TEST wells add 50 µl of compound diluted in binding buffer (final concentration <0.5% DMSO);

to the PLATE control wells add 100 µl of binding buffer;

to ALL wells but PLATE wells add 50 µl of cells to a concentration of 3.0×10e5 cells/well; and to ALL wells add 50 µl of $^{125}$I-labeled human eotaxin to 0.15 nM final concentration ($^{125}$I-labeled eotaxin, #NEX-314 Perkin Elmer Life Sciences Inc.).

Tap the plate to mix and incubate at RT for 30 to 60 minutes. Place the plate on a vacuum manifold, apply vacuum, and wash the plate three times with 200 µl of wash buffer (2.4% NaCl in binding buffer) for each wash. Remove the plastic skirt from the plate and allow the plate to air dry. Punch out the wells and count gamma emissions for each punch.

Figure 5A:
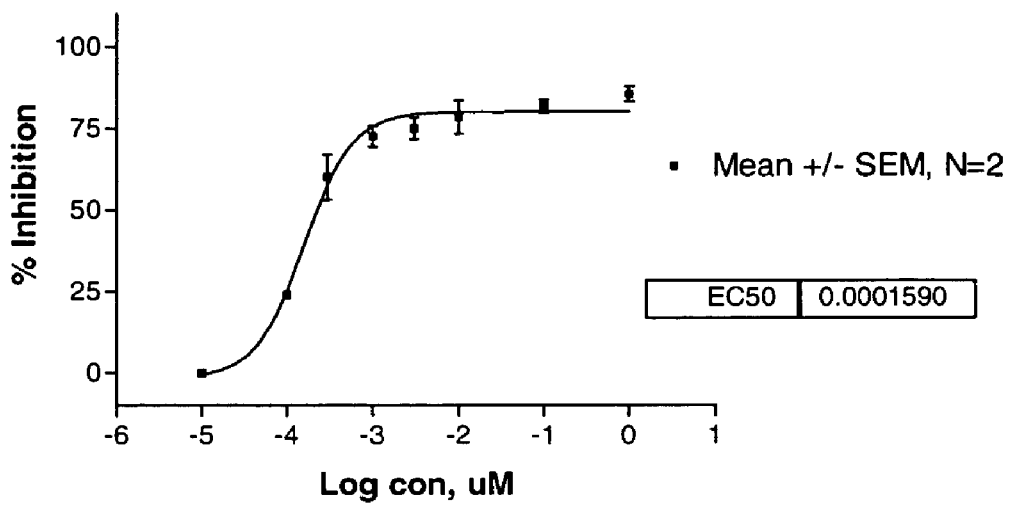
FIG. 5A is a plot depicting a comparison of drug inhibition curves on human eosinophils.
Figure 5B:
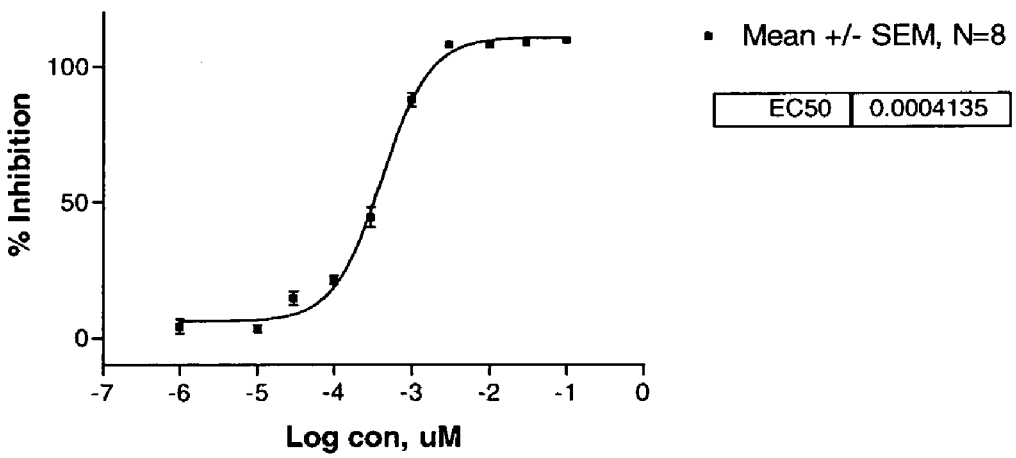
FIG. 5B is a plot depicting a comparison of drug inhibition curves on CHO CCR3/2 clone 5.5.

Binding data were analyzed using Microsoft EXCEL and then graphed using GRAPHPAD PRISMT™. The data indicate high levels of specific eotaxin binding on CHO cells expressing human CCR3/2 (FIG. 1) and further, that drug inhibition curves generated by competing labeled (hot) eotaxin with Compound 1 (N-{(1R,2S)-3-[(3S)-3-(4-fluorobenzyl)-1-piperidinyl]-2-hydroxy-1-methylpropyl}-N'-[3-(1-methyl-1H-tetraazol-5-yl)phenyl]urea; see U.S. Patent Application No. 60/410,198) are comparable, regardless of whether native human eosinophils or CHO CCR3/2 clone 5.5 is used (FIGS. 5A and 5B). Compound 1 has the structure

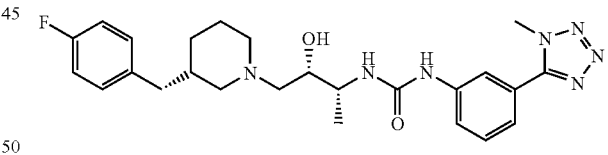

These data indicate that CHO CCR3/2 clone may be a suitable substitute for human eosinophils in the search for compounds that can inhibit binding of eotaxin to CCR3.

Example 7

Signalling Assays

Figure 6:
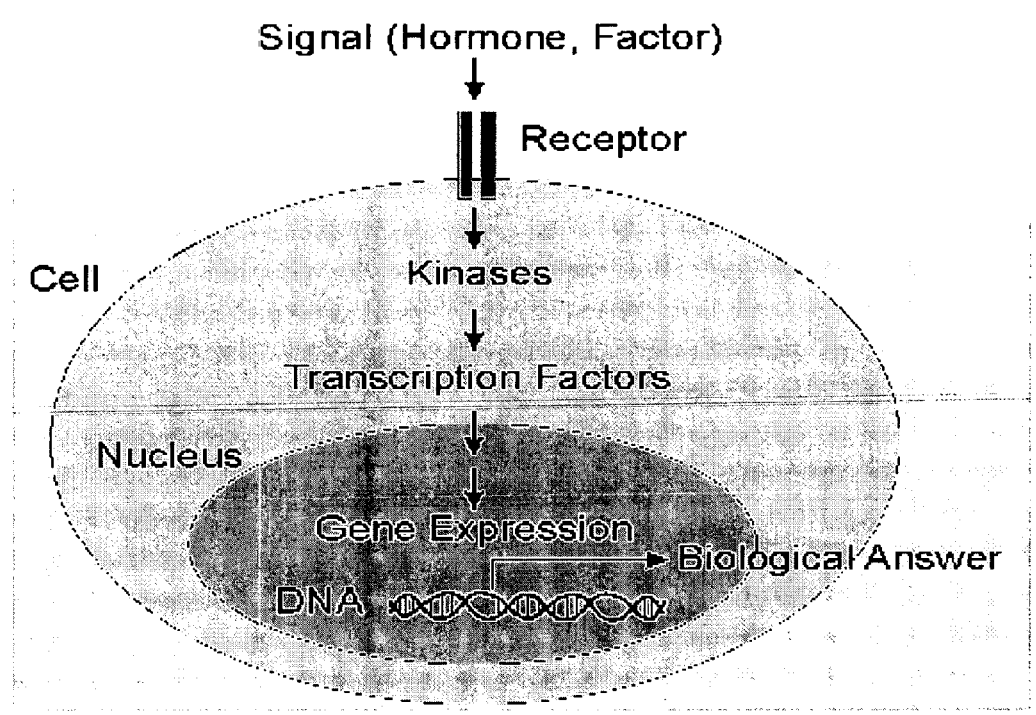
FIG. 6 is a schematic diagram depicting signalling via kinase pathways in a cell.

It has been demonstrated that a CCR3/2 chimera is capable of binding to eotaxin in a manner very similar to that exhibited by the wild-type intact receptor in eosinophils. In FIG. 6, a generic signal transduction pathway is illustrated. For illustrative purposes only, in the present Example, the signalling agent is considered to be eotaxin and the receptor is either CCR3 or CCR3/2. Other chimeric chemokine receptors form elements of the present invention and the recitation of the eotaxin/CCR/3/2 pair in the present example is only for purposes of illustration. Additional chemokine/receptor pairs will be known to those of ordinary skill in the art upon consideration of the present disclosure.

Part of the downstream signalling cascade involves the activity of kinases (proteins that add phosphate groups to specific residues in cellular proteins, thereby causing them to take on new activities and cellular roles). In the present Example, the phosphorylation of Erk (a member of a protein kinase signalling cascade) is considered to be an indication that binding of eotaxin at the cell surface is recognized by the cell signalling machinery that lies within the cytoplasm and nucleus. It would therefore be useful to demonstrate that not only does eotaxin bind to CCR3/2, but that it is able to transmit a signal generated in response to the binding event to the interior of the cell.

Thus, the present invention further provides that a chimeric chemokine receptor (e.g., the chimeric CCR3/2 receptor) when expressed in cells is capable of downstream signalling when binding to its cognate ligand (e.g., eotaxin). Such downstream signalling involves the MAP kinase pathway, more specifically, the phosphorylation of Erk1 and Erk2 subsequent to binding of eotaxin by either CCR3 or CCR3/2.

Figure 7A:
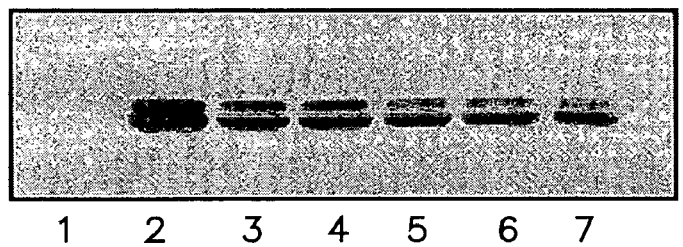
FIG. 7A is a photograph depicting western blot chemiluminescent detection of erk phosphorylation in human eosinophils exposed to human eotaxin.
Figure 7B:
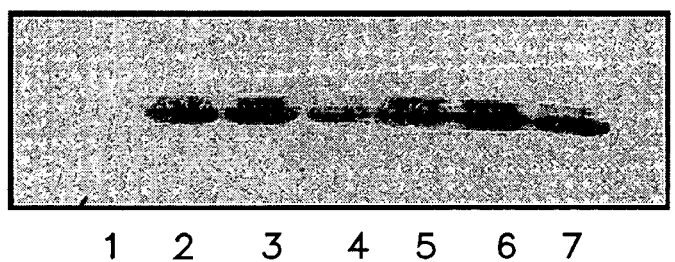
FIG. 7B is a photograph depicting western blot chemiluminescent detection of erk phosphorylation in CHO CCR3/2 Clone 5.5 cells exposed to human eotaxin.

Analysis of cell stimulation for phospho-ERK analysis by western blotting was done as previously described (Scherle et al., (1998) *J. Immunol.* 161(10):5681-86) with the exception that cells were specifically stimulated by exposure to eotaxin (nanomolar exposures to eotaxin listed on the bottoms of FIGS. 7A and 7B) instead of the more generic stimulant lipopolysaccharide as described in Sherle et al. (Scherle et al., (1998) *J. Immunol.* 161(10):5681-86).

The overall result of these studies indicates that the chimeric CCR3/2 receptor not only binds eotaxin with high affinity (as in native human eosinophils) but is able to transmit a signal (in this case Erk phosphorylation) to the interior of the cell in a similar manner as is observed for the wild-type receptor on human eosinophils. Such chimeric receptor cells should be able to replace wild-type receptor expressing cells in ligand and drug binding studies designed to address many physiochemical and biological issues surrounding the development of specific receptor drug inhibitor.

Example 8

Assembling a Chimeric CCR2/3 Receptor cDNA Clone

As noted above, cDNAs for human chemokine receptors CCR2B and CCR3 were cloned from a monocyte cDNA library. Overlapping PCR products consisting of the human CCR2B gene from the N-terminus through the seventh transmembrane domain and the human CCR3 gene from the seventh transmembrane domain through the C-terminus were spliced together as described below.

Using pFLAG-CMV1/CCR2B as a template the following primers were used to amplify a partial CCR2B cDNA encompassing the START codon (in bold) through the seventh transmembrane domain:

```
5' primer:
CCCaagcttATGCTGTCCACATCTCG         (SEQ ID NO:17)
(HindIII site in small case)
```

```
3' primer:
CCgatatcTTCTGAACTTCTCCCCAACG       (SEQ ID NO:18)
(EcoRV site in small case)
```

Using pFLAG-CMV1/CCR3 as a template, the following primers were used to amplify a partial CCR3 cDNA encompassing the seventh transmembrane domain through the STOP codon (reverse sequence in bold):

```
5' primer:
CGaatattTGCGCCACTTCTTCCACAGG       (SEQ ID NO:19)
(SspI site in lower case)
```

```
3' primer:
CGggatccTCTAGACTAAAACAC            (SEQ ID NO:20)
(BamHI site in lower case)
```

The 5' partial CCR2B product was digested with HindIII and EcoRV and the 3' partial CCR3 product was digested with SspI and BamHI. Each product was subsequently gel-purified. The partial cDNA products were ligated into a pFLAG-CMV-3 vector (FIG. 2A).

Figure 8A-2:
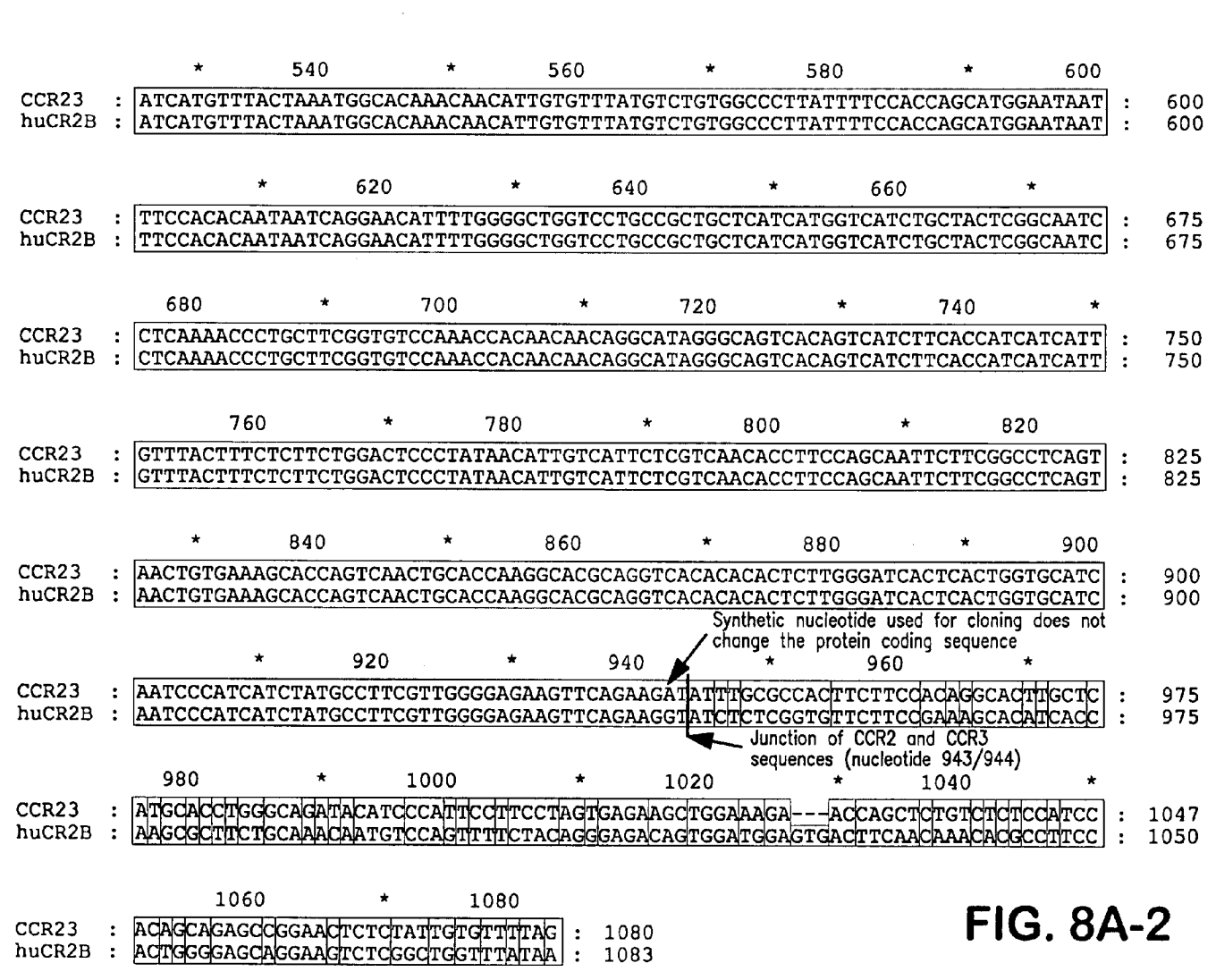

The two blunt-end regions (EcoRV and SspI) come together to re-create the existing codon for tyrosine (Y) at the indicated junction, as depicted in FIGS. 8A and 8B. This completed the assembly of the intact CCR2/3 chimeric molecule containing 7 transmembrane regions and a cytoplasmic tail in the pFLAG-CMV-3 vector.

This chimeric chemokine receptor differs from the sequences of both human CCR2B and CCR3 at the nucleic acid level as indicated below and in FIG. 8A. In the case of the nucleotide comparison, the switch from CCR2 to CCR3 occurs at nucleotide 943 of 1083 meaning that about 87% of the molecule is derived from CCR2 isoform B.

With respect to the amino acid sequence, CCR2B residues 1-314 comprise the N terminus, with the junction site occuring at amino acid 315 of the 360 residue CCR2B amino acid sequence. A tyrosine residue, which is common to CCR2B and CCR3 is the junction site. Thus, about 87.5% of the CCR2/3 chimeric protein is derived from the CCR2 isoform B polypeptide.

Nucleotide number 942 is synthetic occuring in neither CCR2B nor CCR3. This nucleotide was changed to accommodate the use of an EcoRV in the 3' end of the N-terminal partial cDNA product and was done so without changing the protein sequence involved (i.e. AGG, endogenous sequence and AGA, synthetic sequence in bold, both code for the amino acid arginine, R).

REFERENCES

The references cited in the specification are incorporated herein by reference to the extent that they supplement, explain, provide a background for or teach methodology, techniques and/or compositions employed herein. All cited patents, including patent applications, and publications referred to in this application are herein expressly incorporated by reference. Also expressly incorporated herein by reference are the contents of all citations of GenBank accession numbers, LocusID, and other computer database listings, as well as the contents of the Sequence Listing associated herewith.

It will be understood that various details of the invention may be changed without departing from the scope of the invention. Furthermore, the foregoing description is for the purpose of illustration only.

What is claimed is:

1. An isolated polynucleotide encoding a chimeric chemokine receptor comprising the amino acid sequence set forth in SEQ ID NO:24.

2. The polynucleotide of claim 1, wherein the polynucleotide sequence is that set forth in SEQ ID NO:23.

3. A host cell comprising the polynucleotide of claim 1.

4. An isolated polynucleotide that is fully complementary to the polynucleotide of claim 1.

5. A DNA vector comprising the polynucleotide of claim 1.

6. A method for producing a chimeric chemokine receptor comprising:
   (a) growing the host cell of claim 3 in a suitable nutrient medium to produce the chimeric chemokine receptor; and
   (b) isolating the chimeric chemokine receptor from the cell.

* * * * *